United States Patent
Liu et al.

(10) Patent No.: US 9,925,247 B2
(45) Date of Patent: Mar. 27, 2018

(54) IL-15-BASED MOLECULES AND METHODS OF USE THEREOF

(71) Applicant: Altor BioScience Corporation, Miramar, FL (US)

(72) Inventors: Bai Liu, Cooper City, FL (US); Peter Rhode, Miami, FL (US); Wenxin Xu, Pembroke Pines, FL (US); Hing C. Wong, Weston, FL (US)

(73) Assignee: Altor Bioscience Corporation, Miramar, FL (US)

( * ) Notice: Subject to any disclaimer, the term of this patent is extended or adjusted under 35 U.S.C. 154(b) by 0 days.

(21) Appl. No.: 14/755,989

(22) Filed: Jun. 30, 2015

(65) Prior Publication Data

US 2015/0374790 A1   Dec. 31, 2015

Related U.S. Application Data

(60) Provisional application No. 62/018,899, filed on Jun. 30, 2014.

(51) Int. Cl.

| | |
|---|---|
| *A61K 38/20* | (2006.01) |
| *A61K 39/395* | (2006.01) |
| *C07K 16/28* | (2006.01) |
| *C07K 16/32* | (2006.01) |
| *C07K 14/54* | (2006.01) |
| *C07K 14/715* | (2006.01) |
| *A61K 47/48* | (2006.01) |

(52) U.S. Cl.
CPC .... *A61K 38/2086* (2013.01); *A61K 39/39558* (2013.01); *C07K 14/5443* (2013.01); *C07K 14/7155* (2013.01); *C07K 16/2818* (2013.01); *C07K 16/2827* (2013.01); *C07K 16/2887* (2013.01); *C07K 16/32* (2013.01); *C07K 2317/732* (2013.01); *C07K 2319/30* (2013.01)

(58) Field of Classification Search
None
See application file for complete search history.

(56) References Cited

U.S. PATENT DOCUMENTS

| | | |
|---|---|---|
| 2014/0099254 A1 | 4/2014 | Chang et al. |
| 2014/0134128 A1 | 5/2014 | Wong et al. |

FOREIGN PATENT DOCUMENTS

| | | |
|---|---|---|
| WO | WO-2014/028776 A1 | 2/2014 |

OTHER PUBLICATIONS

Tai et al, Journal of Control Release, 2010, vol. 146, No. 3; pp. 264-275.*
Terawaki et al, International Immunology, 2007; vol. 19, No. 7, pp. 881-890.*

* cited by examiner

*Primary Examiner* — Bridget E Bunner
*Assistant Examiner* — Fozia Hamud
(74) *Attorney, Agent, or Firm* — Mintz Levin Cohn Ferris Glovsky and Popeo, P.C.; Peter F. Corless

(57) ABSTRACT

The invention features combination therapies using an IL-15-based superagonist complex and an antibody to effectively treat subjects with cancer and infectious diseases.

25 Claims, 31 Drawing Sheets

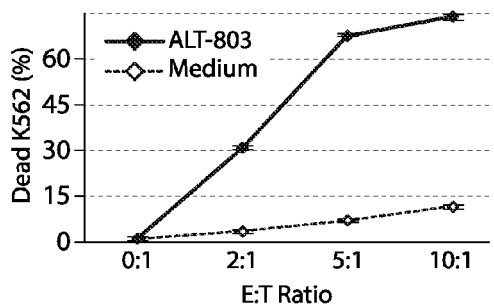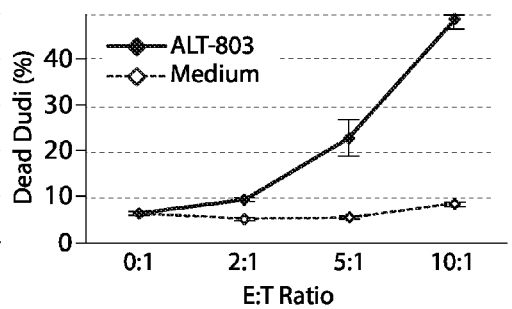
Fig. 6A    Fig. 6B
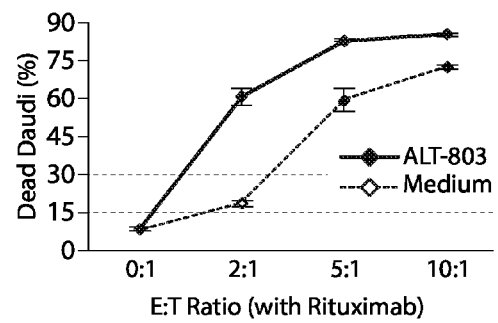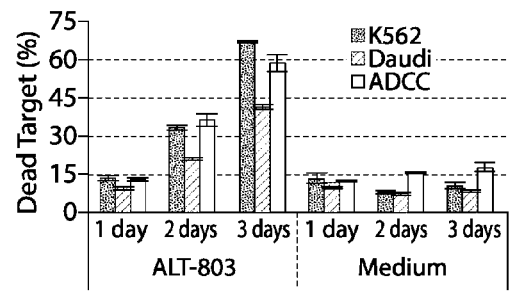
Fig. 6C    Fig. 6D

SEQUENCE LISTING

```
<160> NUMBER OF SEQ ID NOS: 6

<210> SEQ ID NO 1
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggagacag acacactcct gttatgggta ctgctgctct gggttccagg ttccaccggt      60
aactgggtga atgtaataag tgatttgaaa aaaattgaag atcttattca atctatgcat     120
attgatgcta ctttatatac ggaaagtgat gttcacccca gttgcaaagt aacagcaatg     180
aagtgctttc tcttggagtt acaagttatt tcacttgagt ccggagatgc aagtattcat     240
gatacagtag aaaatctgat catcctagca aacgacagtt tgtcttctaa tgggaatgta     300
acagaatctg gatgcaaaga atgtgaggaa ctggaggaaa aaaatattaa agaattttg      360 cagagttttg tacatattgt ccaaatgttc atcaacactt cttaa                    405

<210> SEQ ID NO 2
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
            20                  25                  30

Glu Asp Leu Ile Gln Ser Met His Ile Asp Ala Thr Leu Tyr Thr Glu
        35                  40                  45

Ser Asp Val His Pro Ser Cys Lys Val Thr Ala Met Lys Cys Phe Leu
    50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asp Ser Leu Ser Ser
                85                  90                  95

Asn Gly Asn Val Thr Glu Ser Gly Cys Lys Glu Cys Glu Glu Leu Glu
            100                 105                 110

Glu Lys Asn Ile Lys Glu Phe Leu Gln Ser Phe Val His Ile Val Gln
        115                 120                 125

Met Phe Ile Asn Thr Ser
    130
```

<210> SEQ ID NO 3
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 4
<211> LENGTH: 951
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atggacagac ttacttcttc attcctgctc ctgattgtcc ctgcgtacgt cttgtccatc        60
acgtgccctc cccccatgtc cgtggaacac gcagacatct gggtcaagag ctacagcttg       120
tactccaggg agcggtacat ttgtaactct ggtttcaagc gtaaagccgg cacgtccagc       180
ctgacggagt gcgtgttgaa caaggccacg aatgtcgccc actggacaac ccccagtctc       240
aaatgtatta gagagcccaa atcttgtgac aaaactcaca catgcccacc gtgcccagca       300
cctgaactcc tggggggacc gtcagtcttc ctcttccccc caaaacccaa ggacaccctc       360
atgatctccc ggaccccctga ggtcacatgc gtggtggtgg acgtgagcca cgaagaccct       420
gaggtcaagt tcaactggta cgtggacggc gtggaggtgc ataatgccaa gacaaagccg       480
cgggaggagc agtacaacag cacgtaccgt gtggtcagcg tcctcaccgt cctgcaccag       540
gactggctga atggcaagga gtacaagtgc aaggtctcca acaaagccct cccagccccc       600
atcgagaaaa ccatctccaa agccaaaggg cagccccgag aaccacaggt gtacaccctg       660
cccccatccc gggatgagct gaccaagaac caggtcagcc tgacctgcct ggtcaaaggc       720
ttctatccca gcgacatcgc cgtggagtgg gagagcaatg ggcagccgga gaacaactac       780
aagaccacgc ctcccgtgct ggactccgac ggctccttct tcctctacag caagctcacc       840
gtggacaaga gcaggtggca gcaggggaac gtcttctcat gctccgtgat gcatgaggct       900
ctgcacaacc actacacgca gaagagcctc tccctgtctc cgggtaaata a                951
```

<210> SEQ ID NO 5

<211> LENGTH: 316
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Asp Arg Leu Thr Ser Ser Phe Leu Leu Leu Ile Val Pro Ala Tyr
1               5                   10                  15

Val Leu Ser Ile Thr Cys Pro Pro Met Ser Val Glu His Ala Asp
            20                  25                  30

Ile Trp Val Lys Ser Tyr Ser Leu Tyr Ser Arg Glu Arg Tyr Ile Cys
            35                  40                  45

Asn Ser Gly Phe Lys Arg Lys Ala Gly Thr Ser Ser Leu Thr Glu Cys
        50                  55                  60

Val Leu Asn Lys Ala Thr Asn Val Ala His Trp Thr Thr Pro Ser Leu
65                  70                  75                  80

Lys Cys Ile Arg Glu Pro Lys Ser Cys Asp Lys Thr His Thr Cys Pro
                85                  90                  95

Pro Cys Pro Ala Pro Glu Leu Leu Gly Gly Pro Ser Val Phe Leu Phe
            100                 105                 110

Pro Pro Lys Pro Lys Asp Thr Leu Met Ile Ser Arg Thr Pro Glu Val
        115                 120                 125

Thr Cys Val Val Val Asp Val Ser His Glu Asp Pro Glu Val Lys Phe
130                 135                 140

Asn Trp Tyr Val Asp Gly Val Glu Val His Asn Ala Lys Thr Lys Pro
145                 150                 155                 160

Arg Glu Glu Gln Tyr Asn Ser Thr Tyr Arg Val Val Ser Val Leu Thr
                165                 170                 175

Val Leu His Gln Asp Trp Leu Asn Gly Lys Glu Tyr Lys Cys Lys Val
            180                 185                 190

Ser Asn Lys Ala Leu Pro Ala Pro Ile Glu Lys Thr Ile Ser Lys Ala
        195                 200                 205

Lys Gly Gln Pro Arg Glu Pro Gln Val Tyr Thr Leu Pro Pro Ser Arg
210                 215                 220

Asp Glu Leu Thr Lys Asn Gln Val Ser Leu Thr Cys Leu Val Lys Gly
225                 230                 235                 240

Phe Tyr Pro Ser Asp Ile Ala Val Glu Trp Glu Ser Asn Gly Gln Pro
                245                 250                 255

Glu Asn Asn Tyr Lys Thr Thr Pro Pro Val Leu Asp Ser Asp Gly Ser
            260                 265                 270

Phe Phe Leu Tyr Ser Lys Leu Thr Val Asp Lys Ser Arg Trp Gln Gln
        275                 280                 285

Gly Asn Val Phe Ser Cys Ser Val Met His Glu Ala Leu His Asn His
    290                 295                 300

Tyr Thr Gln Lys Ser Leu Ser Leu Ser Pro Gly Lys
305                 310                 315
```

<210> SEQ ID NO 6
<211> LENGTH: 297
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
                20                  25                  30
Phe Lys Arg Lys Ala Gly Thr Ser Ser Leu Thr Glu Cys Val Leu Asn
            35                  40                  45
Lys Ala Thr Asn Val Ala His Trp Thr Thr Pro Ser Leu Lys Cys Ile
        50                  55                  60
Arg Glu Pro Lys Ser Cys Asp Lys Thr His Thr Cys Pro Pro Cys Pro
65                  70                  75                  80
Ala Pro Glu Leu Leu Gly Gly Pro Ser Val Phe Leu Phe Pro Pro Lys
                85                  90                  95
Pro Lys Asp Thr Leu Met Ile Ser Arg Thr Pro Glu Val Thr Cys Val
            100                 105                 110
Val Val Asp Val Ser His Glu Asp Pro Glu Val Lys Phe Asn Trp Tyr
        115                 120                 125
Val Asp Gly Val Glu Val His Asn Ala Lys Thr Lys Pro Arg Glu Glu
        130                 135                 140
Gln Tyr Asn Ser Thr Tyr Arg Val Val Ser Val Leu Thr Val Leu His
145                 150                 155                 160
Gln Asp Trp Leu Asn Gly Lys Glu Tyr Lys Cys Lys Val Ser Asn Lys
                165                 170                 175
Ala Leu Pro Ala Pro Ile Glu Lys Thr Ile Ser Lys Ala Lys Gly Gln
            180                 185                 190
Pro Arg Glu Pro Gln Val Tyr Thr Leu Pro Pro Ser Arg Asp Glu Leu
        195                 200                 205
Thr Lys Asn Gln Val Ser Leu Thr Cys Leu Val Lys Gly Phe Tyr Pro
        210                 215                 220
Ser Asp Ile Ala Val Glu Trp Glu Ser Asn Gly Gln Pro Glu Asn Asn
225                 230                 235                 240
Tyr Lys Thr Thr Pro Pro Val Leu Asp Ser Asp Gly Ser Phe Phe Leu
                245                 250                 255
Tyr Ser Lys Leu Thr Val Asp Lys Ser Arg Trp Gln Gln Gly Asn Val
            260                 265                 270
Phe Ser Cys Ser Val Met His Glu Ala Leu His Asn His Tyr Thr Gln
        275                 280                 285
Lys Ser Leu Ser Leu Ser Pro Gly Lys
290                 295
```

IL-15-BASED MOLECULES AND METHODS OF USE THEREOF

RELATED APPLICATIONS

This application claims the benefit of priority under 35 U.S.C. § 119(e) to U.S. Provisional Application No. 62/018,899, filed Jun. 30, 2014, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 22, 2015, is named 48277-526001WO_SL.txt and is 10,341 bytes in size.

FIELD OF THE INVENTION

This invention relates generally to the field of therapies for treatment of cancer and infectious agents.

BACKGROUND OF THE INVENTION

Prior to the invention described herein, there was a pressing need to develop new strategies to augment and/or direct immune activity against cancer and infected cells.

SUMMARY OF THE INVENTION

The invention is based, at least in part, on the surprising discovery that an antibody in combination with ALT-803, a complex of an interleukin-15 (IL-15) superagonist mutant and a dimeric IL-15 receptor α/Fc fusion protein, is useful for enhancing an immune response against a neoplasia (e.g., a glioblastoma, prostate cancer, hematological cancer, B-cell neoplasms, multiple myeloma, B-cell lymphoma, Hodgkin's lymphoma, acute myeloid leukemia, chronic lymphocytic leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, colorectal cancer, ovarian cancer, non-small cell lung carcinoma, B cell non-Hodgkin lymphoma, and squamous cell head and neck carcinoma) or an infection (e.g., a viral infection with human immunodeficiency virus).

Methods for treating a neoplasia or an infection in a subject are carried out by administering to the subject an effective amount of an antibody (or antibody-like molecule) and an effective amount of a pharmaceutical composition comprising an IL-15N72D:IL-15RαSu/Fc complex (ALT-803), wherein the ALT-803 comprises a dimeric IL-15RαSu/Fc and two IL-15N72D molecules. In one aspect, the IL-15N72D molecule comprises SEQ ID NO: 3. An exemplary IL-15RαSu/Fc comprises SEQ ID NO: 6.

The subject is preferably a mammal in need of such treatment, e.g., a subject that has been diagnosed with a neoplasia or an infection or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Suitable neoplasias for treatment with the methods described herein include a glioblastoma, prostate cancer, acute myeloid leukemia, B-cell neoplasm, multiple myeloma, B-cell lymphoma, non-Hodgkin's lymphoma, chronic lymphocytic leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, colorectal cancer, and ovarian cancer. An exemplary infection for treatment using the methods described herein is infection with human immunodeficiency virus (HIV). The methods described herein are also useful to treat bacterial infections (e.g., gram positive or gram negative bacteria) (Oleksiewicz et al. 2012. Arch Biochem Biophys. 526:124-31).

Preferably, administration of the compositions described herein also prevents future recurrence of neoplasia or infection after treatment of the disease.

Additionally, the methods of the invention are useful for effective treatment of autoimmune diseases, in which inhibition or reduction of cells associated with the autoimmune responses provides clinical benefit to patients. Such cells include leucocytes, particularly B- or T-cells and such autoimmune diseases include rheumatoid arthritis, juvenile idiopathic arthritis, psoriasis, Crohn's disease, ulcerative colitis, multiple sclerosis, ankylosing spondylitis, type 1 diabetes and systemic lupus erythematosus (Chan et al. 2010. Nat Rev Immunol. 10:301-16).

Exemplary effective doses of ALT-803 include between 0.1 μg/kg and 100 mg/kg body weight, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, or 900 μg/kg body weight or 1, 2, 3, 4, 5, 6, 7, 8, 9, 10, 20, 30, 40, 50, 60, 70, 80, 90, or 100 mg/kg body weight.

In some cases, the ALT-803 is administered daily, e.g., every 24 hours. Or, the ALT-803 is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

Exemplary effective daily doses of ALT-803 include between 0.1 μg/kg and 100 μg/kg body weight, e.g., 0.1, 0.3, 0.5, 1, 5, 10, 15, 20, 25, 30, 35, 40, 45, 50, 55, 60, 65, 70, 75, 80, 85, 90, 95, or 99 μg/kg body weight.

Alternatively, the ALT-803 is administered about once per week, e.g., about once every 7 days. Or, the ALT-803 is administered twice per week, three times per week, four times per week, five times per week, six times per week, or seven times per week. Exemplary effective weekly doses of ALT-803 include between 0.0001 mg/kg and 4 mg/kg body weight, e.g., 0.001, 0.003, 0.005, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, or 4 mg/kg body weight. For example, an effective weekly dose of ALT-803 is between 0.1 μg/kg body weight and 400 μg/kg body weight. Alternatively, ALT-803 is administered at a fixed dose or based on body surface area (i.e., per m²).

In some cases, subjects receive two 6-week cycles consisting of 4 weekly ALT-803 intravenous doses followed by a 2-week rest period. Ultimately, the attending physician or veterinarian decides the appropriate amount and dosage regimen.

The compositions described herein are administered systemically, intravenously, subcutaneously, intramuscularly, intravesically, or by instillation. The antibody and ALT-803 may be administered simultaneously or sequentially.

Preferably, the antibody (Ab) is a tumor-specific antibody, an immune checkpoint inhibitor, or an antiviral antibody. Preferred antibodies are composed of heavy and light chain immunoglobulin (Ig) proteins, which may include rodent, human, chimeric and humanized forms. Additionally, the method described herein could utilize antibody-like molecules, such as molecules comprising an antigen binding domain (e.g., single chain antibody, Fab, Fv, T-cell receptor binding domain, ligand binding domain or receptor binding domain). In some cases, these domains are preferably linked to an Fc domain. The Ig may be of any of the known isotypes (e.g., IgA, IgD, IgE, IgG, IgG1, IgG2, IgG3, IgG4, IgG2a, IgG2b, and IgM). In some applications described herein using diseased targeted Abs (or antibody-like molecules), the Ab (or antibody-like molecule) contains a heavy chain or Fc domain capable of interacting with Fc receptors to mediate antibody-dependent cell-mediated cytotoxicity (ADCC) and/or antibody dependent cellular phagocytosis (ADCP). In other cases, antibodies conjugated to effector molecules may be used. In other applications such use of immune checkpoint blocker, the preferred Ab (or antibody-like molecule) contains a heavy chain or Fc domain (e.g., IgG4 Fc) that is incapable of effectively mediating ADCC or ADCP.

In certain embodiments, the antigen for the antibody comprises a cell surface receptor or ligand. In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

Preferably, the tumor-specific antibody is capable of binding to an antigen on a tumor cell. Tumor-specific antibodies approved for treatment of patients with cancer include rituximab, ofatumumab, and obinutuzumab (anti-CD20 Abs); trastuzumab and pertuzumab (anti-HER2 Abs); cetuximab and panitumumab (anti-EGFR Abs); and alemtuzumab (anti-CD52 Ab). Similarly, antibody-effector molecule conjugates specific to CD20 ($^{90}$Y-labeled ibritumomab tiuxetan, $^{131}$I-labeled tositumomab), HER2 (ado-trastuzumab emtansine), CD30 (brentuximab vedotin) and CD33 (gemtuzumab ozogamicin) have been approved for cancer therapy (Sliwkowski M X, Mellman I. 2013 Science 341: 1192).

Additionally, preferred antibodies of the invention may include various other tumor-specific antibodies known in the art. The antibodies and their respective targets for treatment of cancer include but are not limited to nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti-CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxorubicin immunoconjugate (anti-Lewis-Y antigen), CC49 (anti-TAG-72), cedelizumab (anti-CD4), Ch.14.18 (anti-GD2), ch-TNT (anti-DNA associated antigens), citatuzumab bogatox (anti-EpCAM), cixutumumab (anti-IGF-1 receptor), clivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HER3), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-SAC), epitumomab cituxetan (anti-episialin), epratuzumab (anti-CD22), ertumaxomab (anti-HER2/neu, CD3), etaracizumab (anti-integrin αvβ3), faralimomab (anti-Interferon receptor), farletuzumab (anti-folate receptor 1), FBTA05 (anti-CD20), ficlatuzumab (anti-HGF), figitumumab (anti-IGF-1 receptor), flanvotumab (anti-TYRP1(glycoprotein 75)), fresolimumab (anti-TGF β), futuximab (anti-EGFR), galiximab (anti-CD80), ganitumab (anti-IGF-I), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), IMAB362 (anti-CLDN18.2), IMC-CS4 (anti-CSF1R), IMC-TR1 (TGFβRII), imgatuzumab (anti-EGFR), inclacumab (anti-selectin P), indatuximab ravtansine (anti-SDC1), inotuzumab ozogamicin (anti-CD22), intetumumab (anti-CD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (anti-PDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor α-chain), milatuzumab (anti-CD74), minretumomab (anti-TAG-72), mitumomab (anti-GD3 ganglioside), mogamulizumab (anti-CCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-R α), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MUC1), parsatuzumab (anti-EGFL7), pascolizumab (anti-IL-4), patritumab (anti-HER3), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-FAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vantictumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (anti-integrin α5β1), vorsetuzumab mafodotin (anti-CD70), votumumab (anti-tumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAP1), and GDC-0199 (anti-Bcl-2).

Other antibodies or tumor target binding proteins useful in the invention (e.g. TCR domains) include, but are not limited to, those that bind the following antigens (the cancer indications represent non-limiting examples): aminopeptidase N (CD13), annexin A1, B7-H3 (CD276, various cancers), CAl25 (ovarian cancers), CA15-3 (carcinomas), CA19-9 (carcinomas), L6 (carcinomas), Lewis Y (carcinomas), Lewis X (carcinomas), alpha fetoprotein (carcinomas), CA242 (colorectal cancers), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma, B-cell neoplasmas, autoimmune diseases), CD21 (B-cell lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (metastatic melanoma, sarcoma), CD52 (leukemia), CD56 (small cell lung cancers, ovarian cancer, Merkel cell carcinoma, and the liquid tumor, multiple myeloma), CD66e (carcinomas), CD70 (metastatic renal cell carcinoma and non-Hodgkin lymphoma), CD74 (multiple myeloma), CD80 (lymphoma), CD98 (carcinomas), CD123 (leukemia), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (CEA, CD66e) (breast, colorectal and lung cancers), DLL4 (A-like-4), EGFR (various cancers), CTLA4 (melanoma), CXCR4 (CD 184, heme-oncology, solid tumors), Endoglin (CD 105, solid tumors), EPCAM (epithelial cell adhesion molecule, bladder, head, neck, colon, NHL prostate, and ovarian cancers), ERBB2 (lung, breast, prostate cancers), FCGR1 (autoimmune diseases), FOLR (folate receptor, ovarian cancers), FGFR (carcinomas), GD2 ganglioside (carcinomas), G-28 (a cell surface antigen glycolipid, melanoma), GD3 idiotype (carcinomas), heat shock proteins (carcinomas), HER1 (lung, stomach cancers), HER2 (breast, lung and ovarian cancers), HLA-DR10 (NHL), HLA-DRB (NHL, B cell leukemia), human chorionic gonadotropin (carcinomas), IGF1R (solid tumors, blood cancers), IL-2 receptor (T-cell leukemia and lymphomas), IL-6R (multiple myeloma, RA, Castleman's disease, IL6 dependent tumors), integrins (αvβ3, α5β1, α6β4, α11β3, α5β5, αvβ5, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 (breast, ovarian, cervix, bronchus and gastrointestinal cancer), MUC16 (CA125) (ovarian cancers), CEA (colorectal cancer), gp100 (melanoma), MARTI (melanoma), MPG (melanoma), MS4A1 (membrane-spanning 4-domains subfamily A, small cell lung cancers, NHL), nucleolin, Neu oncogene product (carcinomas), P21 (carcinomas), nectin-4 (carcinomas), paratope of anti-(N-glycolylneuraminic acid, breast, melanoma cancers), PLAP-like testicular alkaline phosphatase (ovarian, testicular cancers), PSMA (prostate tumors), PSA (prostate), ROB04, TAG 72 (tumour associated glycoprotein 72, AML, gastric, colorectal, ovarian cancers), T cell transmembrane protein (cancers), Tie (CD202b), tissue factor, TNFRSF10B (tumor necrosis factor receptor superfamily member 10B, carcinomas), TNFRSF13B (tumor necrosis factor receptor superfamily member 13B, multiple myeloma, NHL, other cancers, RA and SLE), TPBG (trophoblast glycoprotein, renal cell carcinoma), TRAIL-R1 (tumor necrosis apoptosis inducing ligand receptor 1, lymphoma, NHL, colorectal, lung cancers), VCAM-1 (CD106, Melanoma), VEGF, VEGF-A, VEGF-2 (CD309) (various cancers). Some other tumor associated antigen targets have been reviewed (Gerber, et al, mAbs 2009 1:247-253; Novellino et al, Cancer Immunol Immunother. 2005 54:187-207, Franke, et al, Cancer Biother Radiopharm. 2000, 15:459-76, Guo, et al., Adv Cancer Res. 2013; 119: 421-475, Parmiani et al. J Immunol. 2007 178:1975-9). Examples of these antigens include Cluster of Differentiations (CD4, CD5, CD6, CD7, CD8, CD9, CD10, CD1 1a, CD1 1b, CD1 1c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), annexin A1, nucleolin, endoglin (CD105), ROB04, amino-peptidase N, -like-4 (DLL4), VEGFR-2 (CD309), CXCR4 (CD184), Tie2, B7-H3, WT1, MUC1, LMP2, HPV E6 E7, EGFRvIII, HER-2/neu, idiotype, MAGE A3, p53 nonmutant, NY-ESO-1, GD2, CEA, MelanA/MART1, Ras mutant, gp100, p53 mutant, proteinase3 (PR1), bcr-abl, tyrosinase, survivin, hTERT, sarcoma translocation breakpoints, EphA2, PAP, ML-IAP, AFP, EpCAM, ERG (TMPRSS2 ETS fusion gene), NA17, PAX3, ALK, androgen receptor, cyclin B 1, polysialic acid, MYCN, RhoC, TRP-2, GD3, fucosyl GM1, mesothelin, PSCA, MAGE A1, sLe(a), CYPIB I, PLAC1, GM3, BORIS, Tn, GloboH, ETV6-AML, NY-BR-1, RGSS, SART3, STn, carbonic anhydrase IX, PAXS, OY-TES1, sperm protein 17, LCK, HMWMAA, AKAP-4, SSX2, XAGE 1, B7H3, legumain, Tie 2, Page4, VEGFR2, MAD-CT-1, FAP, PDGFR-13, MAD-CT-2, and Fos-related antigen 1.

Additionally, preferred antibodies of the invention include those specific to antigens and epitope targets associated with infected cells that are known in the art. Such targets include but are not limited those derived from the following infectious agents are of interest: HIV virus (particularly antigens derived from the HIV envelope spike and/or gp120 and gp41 epitopes), Human papilloma virus (HPV), *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, -influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M arginini, Acholeplasma laidlawii, M. salivarium* and *M. pneumoniae.*

In other embodiments, the antibody (or antibody-like molecule) is specific to an immune checkpoint molecule or its ligand and acts as an inhibitor of immune checkpoint suppressive activity or as an agonist of immune checkpoint stimulatory activity. Such immune checkpoint molecules and ligands include PD1, PDL1, PDL2, CTLA4, CD28, CD80, CD86, B7-H3, B7-H4, B7-H5, ICOS-L, ICOS, BTLA, CD137L, CD137, HVEM, KIR, 4-1BB, OX40L, CD70, CD27, OX40, GITR, IDO, TIM3, GAL9, VISTA, CD155, TIGIT, LIGHT, LAIR-1, Siglecs and A2aR (Pardoll D M. 2012. Nature Rev Cancer 12:252-264, Thaventhiran T, et al. 2012. J Clin Cell Immunol S12:004). Additionally, preferred antibodies of the invention may include ipilimumab and tremelimumab (anti-CTLA4). nivolumab, pembrolizumab, pidilizumab, TSR-042, ANB011, AMP-514 and AMP-224 (a ligand-Fc fusion) (anti-PD1), MPDL3280A, MEDI4736, MEDI0680, and BMS-9365569 (anti-PDL1), MEDI6469 (anti-OX40 agonist), BMS-986016, IMP701, IMP731, and IMP321 (anti-LAG3).

In one aspect, the addition of ALT-803 to antibody treatment in vitro or in vivo increases cytotoxicity of immune cells against diseased or disease-associated cells. In some cases, ALT-803 is capable of stimulating immune cells to augment ADCC or ADCP activity against tumor, infected or autoimmune disease-associated cells mediated by a disease-specific antibody (or antibody-like molecule). In one embodiment, treatment of immune cells with ALT-803 increases ADCC or ADCP activity against diseased of disease-associated cells mediated by a disease target-specific antibody by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In a preferred embodiment, immune cells are treated with ALT-803 and used to kill tumor cells via ADCC or ADCP mediated a tumor-specific antibody, wherein the level of tumor cell death is at least 5% greater, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than that seen with immune cells that were not treated with ALT-803. In preferred embodiments, tumor-specific ADCC or ADCP in the subject is augmented by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following the ALT-803 and antibody administration. In particular embodiments, NK cell-based ADCC activity is augmented by ALT-803 treatment.

In other cases, ALT-803 stimulates $CD4^+$ and $CD8^+$ T cells to kill diseased or disease-associated cells, e.g., tumor cells or infected cells. Preferably, ALT-803 treatment stimulates immune cell cytolytic activity and immune checkpoint blockers treatment inhibits immunosuppressive responses, such that in combination these treatments provide highly effective and/or durable activity against the tumor or infected cells. In some embodiments, ALT-803 increases serum levels of interferon gamma (IFN-γ) and/or IL-6, stimulates NK and T cell proliferation and upregulated NK and T cell expression of activation markers including CD25, CD69, perforin and granzyme. Induction of these markers may enhance the responsiveness or cytolytic activity of the immune cells against diseased cells. For example, the methods described herein stimulate NK cells to kill tumor or infected cells.

In other embodiments, ALT-803 induces the activity and/or level of other innate immune cells including neutrophils or monocytic cells. Such cells are known to mediate ADCC and ADCP of therapeutic antibodies against diseased cells, e.g., tumor cells or infected cells (Golay, et al. Blood. 2013 122:3482-91, Richards, et al, Mol Cancer Ther 2008 7:2517-27). Preferably, combination therapy of ALT-803 and antibodies provides improve clinical responses in patients with cancer or infections through a mechanism that is mediated, at least in part, by innate immune cells. For example, the methods described herein stimulate neutrophils or monocytic cells to kill tumor or infected cells.

Preferably, the methods described herein result in a reduced/decreased number of tumor or infected cells compared to the number of tumor or infected cells prior to administration of the compositions herein. Alternatively, the methods described herein result in a decreased disease progression of the neoplasia or infection. Preferably, the methods described herein result in prolonged survival of a subject compared to untreated subjects.

In some cases, methods for treating a neoplasia or an infection in a subject are carried out by administering to the subject an effective amount of *Bacillus* Calmette-Guerin (BCG) and an effective amount of a pharmaceutical composition comprising ALT-803, wherein the ALT-803 comprises a dimeric IL-15RαSu/Fc and two IL-15N72D molecules. For example, subjects receive BCG plus ALT-803 weekly via a urinary catheter in the bladder for 6 consecutive weeks.

Also provided is a kit for the treatment of a neoplasia, the kit comprising an effective amount of ALT-803, an antibody, and directions for the use of the kit for the treatment of a neoplasia.

A kit for the treatment of an infection comprises an effective amount of ALT-803, an antibody, and directions for the use of the kit for the treatment of an infection.

In certain aspects of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt), and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15Rβγ C receptors compared to the native IL-15 polypeptide. Alternatively, the IL-15 variant functions as an IL-15 antagonist as demonstrated by e.g., decreased binding activity for the IL-15Rβγ C receptors compared to the native IL-15 polypeptide.

Methods for killing a target cell are carried out by contacting a plurality of cells with an antibody and ALT-803, wherein the plurality of cells further include immune cells bearing the IL-15R chains recognized by the IL-15 domain, or immune cells bearing Fc receptor chains recognized by the Fc domain, and the target cells bearing an antigen recognized by an the antibody (e.g., an anti-CD20 antibody), and killing the target cells. For example, the target cells are tumor cells or infected (e.g., virally infected) cells.

A method for killing diseased cells expressing a target antigen is carried out by treating immune cells with an effective amount of an IL-15N72D:IL-15RαSu/Fc complex (ALT-803), mixing the ALT-803-treated immune cells with an antibody specific to a target antigen and diseased cells expressing said target antigen, and killing the diseased cells via ADCC or ADCP mediated by the ALT-803-treated immune cells and target antigen-specific antibody. In one aspect, the level of diseased cell killing is increased by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% compared to that mediated by immune cells that were not treated with ALT-803.

The invention also provides methods for preventing or treating disease in a patient in which the diseased cells express a disease associated antigen, the method including the steps of: contacting a plurality of cells with an antibody and ALT-803, and damaging or killing the disease cells sufficient to prevent or treat the disease in the patient. In preferred embodiments, combination therapy with ALT-803 and an antibody can decrease disease progression and/or prolong patient survival.

The invention provides methods of stimulating immune responses in a mammal by administering to the mammal an effective amount of an antibody and an effective amount of ALT-803.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, or small compound. An exemplary therapeutic agent is ALT-803.

By "ALT-803" is meant a complex comprising IL-15N72D noncovalently associated with a dimeric IL-15RαSu/Fc fusion protein and having immune stimulating activity. In one embodiment, the IL-15N72D and/or IL-15RαSu/Fc fusion protein comprises one, two, three, four or more amino acid variations relative to a reference sequence. An exemplary IL-15N72D amino acid sequence is provided below.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. F(ab')2, Fab', Fab, Fv) capable of binding the epitope, antigen or antigenic fragment of interest.

By "binding to" a molecule is meant having a physicochemical affinity for that molecule.

"Detect" refers to identifying the presence, absence or amount of the analyte to be detected.

By "disease" is meant any condition or disorder that damages or interferes with the normal function of a cell, tissue, or organ. Examples of diseases include neoplasias and infections.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, gastric and esophageal cancer, head and neck cancer, rectal cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In particular embodiments, the neoplasia is multiple myeloma, beta-cell lymphoma, urothelial/bladder carcinoma or melanoma. As used herein, "obtaining" as in "obtaining an agent" includes synthesizing, purchasing, or otherwise acquiring the agent.

By "reduces" is meant a negative alteration of at least 5%, 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100.mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline. The subject is preferably a mammal in need of such treatment, e.g., a subject that has been diagnosed with B cell lymphoma or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

Treatment of patients with neoplasia may include any of the following: Adjuvant therapy (also called adjunct therapy or adjunctive therapy) to destroy residual tumor cells that may be present after the known tumor is removed by the initial therapy (e.g. surgery), thereby preventing possible cancer reoccurrence; neoadjuvant therapy given prior to the surgical procedure to shrink the cancer; induction therapy to cause a remission, typically for acute leukemia; consolidation therapy (also called intensification therapy) given once a remission is achieved to sustain the remission; maintenance therapy given in lower or less frequent doses to assist in prolonging a remission; first line therapy (also called standard therapy); second (or 3rd, 4th, etc.) line therapy (also called salvage therapy) is given if a disease has not responded or reoccurred after first line therapy; and palliative therapy (also called supportive therapy) to address symptom management without expecting to significantly reduce the cancer.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of excludes any element, step, or ingredient not specified in the claim. The transitional phrase" consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1E and FIG. 1F represent the CD4/CD8 ratios determined from the results obtained in FIG. 1C and FIG. 1D, respectively.

FIG. 6A-FIG. 6D are a series of line graphs and a bar chart demonstrating cytotoxicity of human PBMCs against Daudi human B-cell lymphoma and K562 human myelogenous leukemia cells induced by ALT-803. Human PBMCs were used as effector cells and Celltrace Violet-labeled Daudi and K562 cells were used as target cells. The human PBMCs were mixed with K562 cells (FIG. 6A), Daudi cells (FIG. 6B) or Daudi cells with Rituximab (anti-CD20 Ab) at 10 nM (FIG. 6C) at the indicated E:T ratio in RPMI-10 with or without ALT-803 at 10 nM. The cell mixtures were incubated at 37° C. for 3 days and the viability of Daudi and K562 target cells was assessed by analysis of propidium iodide staining of violet-labeled target cells on a FACSVerse flow cytometer. Human PBMCs were mixed with violet-labeled K562 or Daudi cells at 10:1 ratio or with Daudi cells plus Rituximab (ADCC) at 2:1 ratio in RPMI-10 with or without ALT-803 at 10 nM. Following 1 to 3 days of incubation at 37° C., the % cytotoxicity of the target cells was determined (FIG. 6D).

Figure 14A:
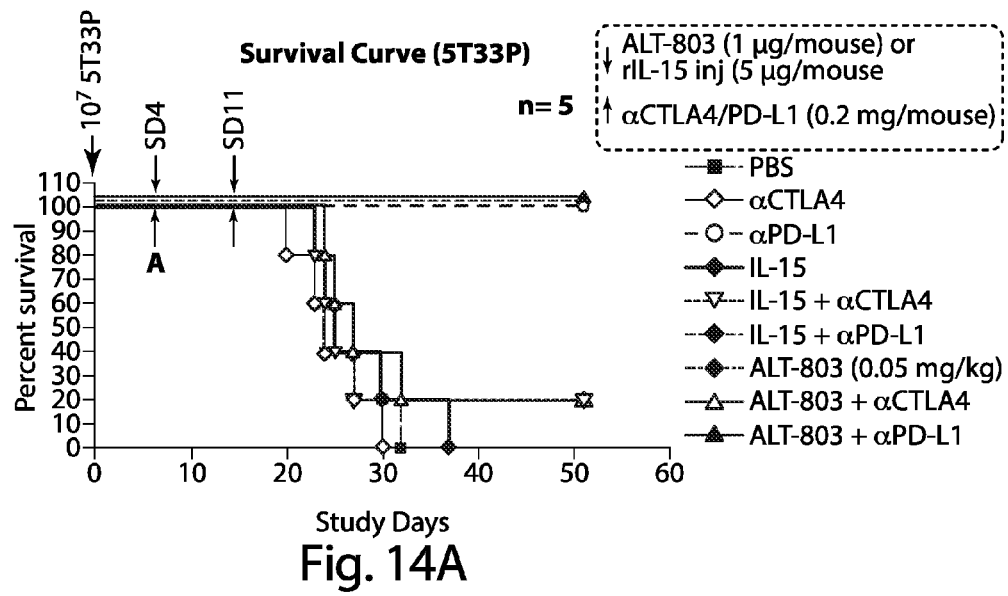
Figure 14B:
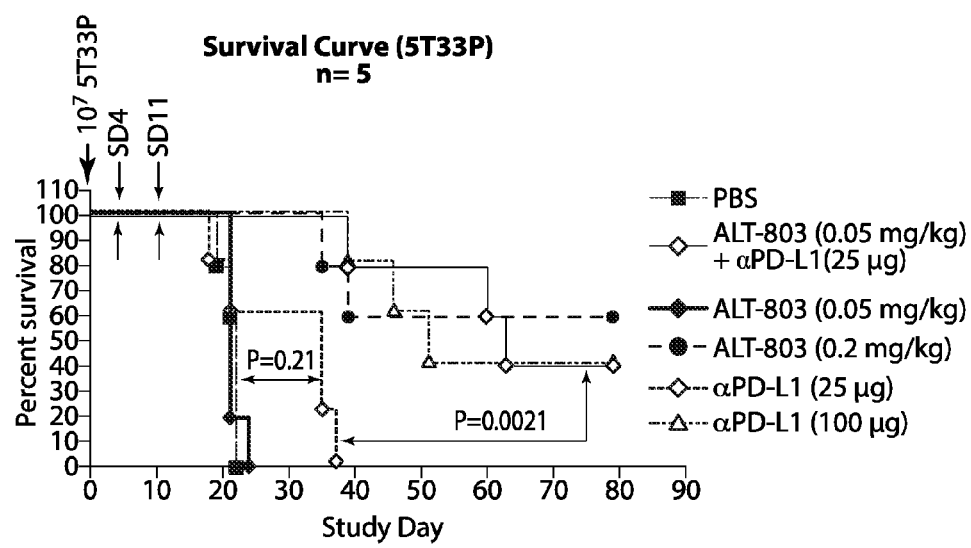

FIG. 14A and FIG. 14B are a series of line graphs demonstrating the prolonged survival of mice bearing 5T33P myeloma tumors following ALT-803 plus anti-PD-L1 Ab therapy. In FIG. 14A, C57BL/6 mice bearing 5T33P myeloma tumors were treated with PBS, ALT-803, IL-15 monotherapies and combination therapies with anti-CTLA4 Ab and anti-PD-L1 Ab (0.2 mg/mouse) as indicated in the figure. The survival of the mice was monitored and Kaplan-Meier survival curves were plotted. In FIG. 14B, C57BL/6 mice bearing 5T33P myeloma tumors were treated with PBS, suboptimal ALT-803 (0.05 mg/kg), suboptimal anti-PD-L1 Ab (5 µg) or combination ALT-803+anti-PD-L1 Ab as indicated in the figure. The survival of the mice was monitored and Kaplan-Meier survival curves were plotted.

Figure 15A:
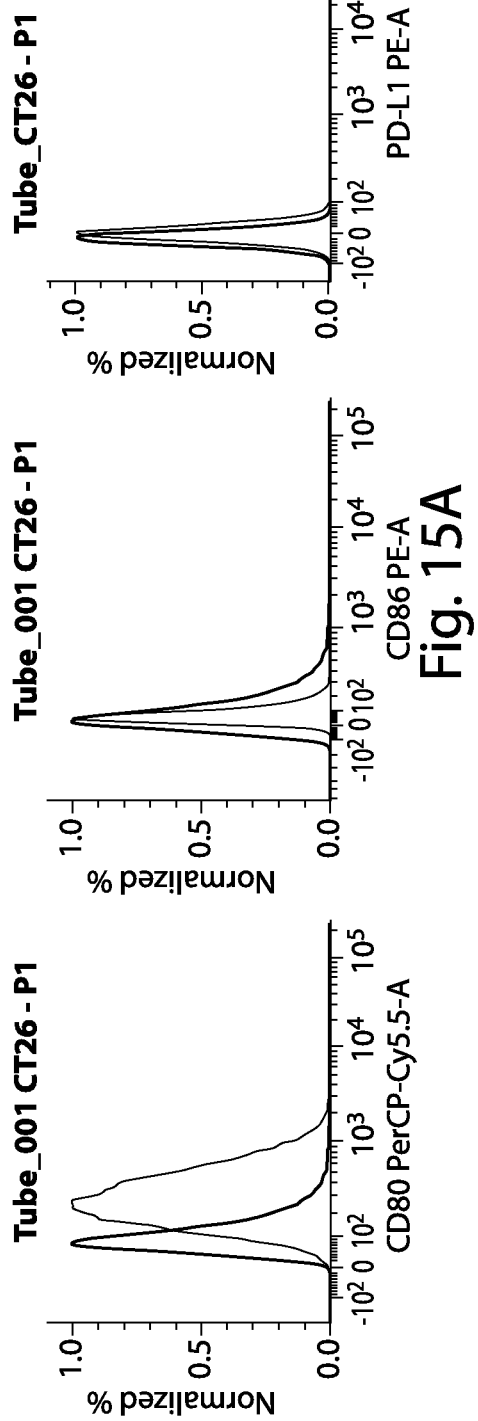
Figure 15B:
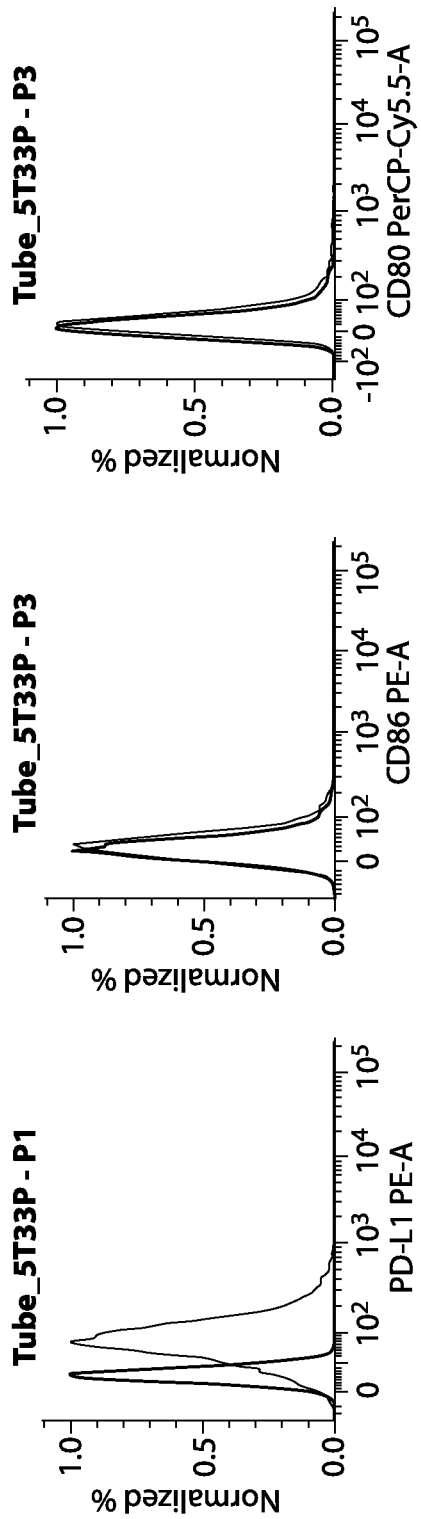
Figure 16A:
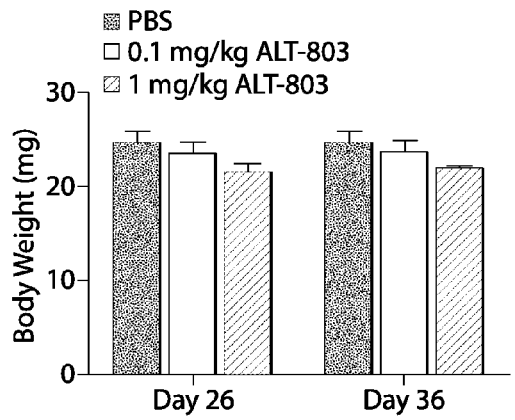
Figure 16B:
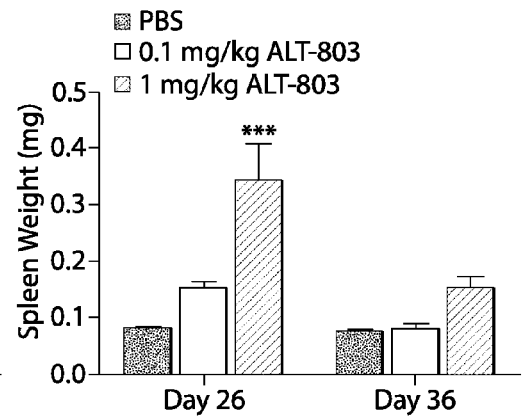
Figure 16C:
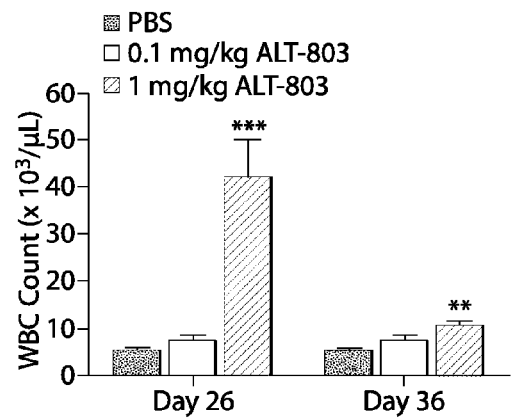
Figure 16D:
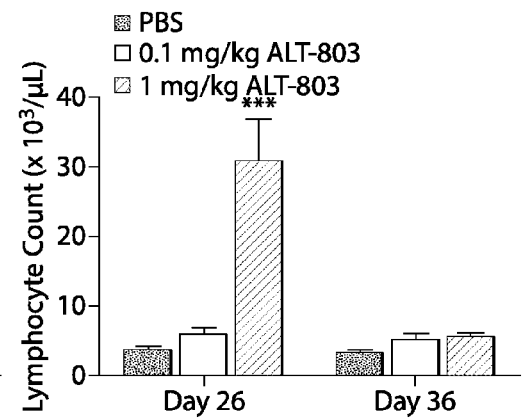
Figure 16E:
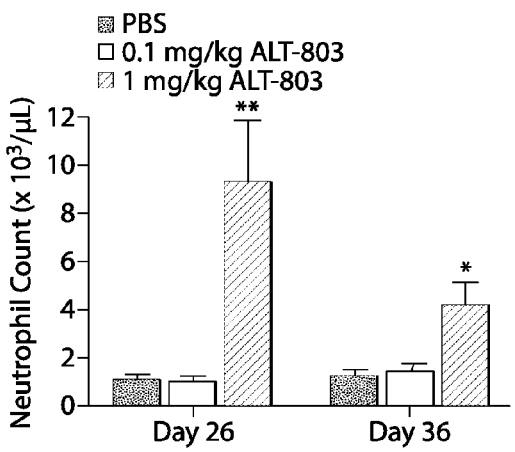
Figure 16F:
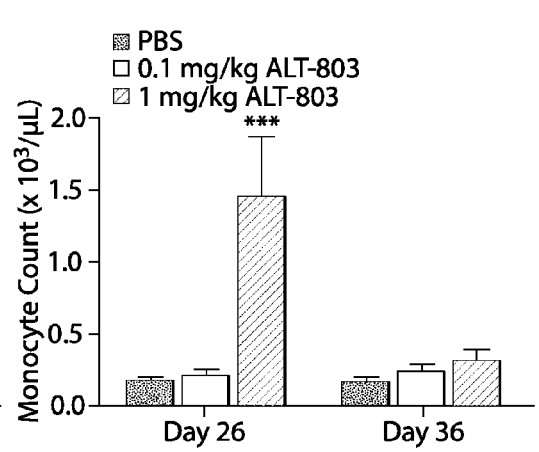

FIG. 15A and FIG. 15B are a series of graphs showing the expression of ligands for PD1 and CTLA4 on the surface of tumor cells. CT26 (FIG. 15A) and 5T33P (FIG. 15B) tumor cells were stained with antibodies to PD-L1, CD86 and CD80 (red line) or isotype controls (black line) and then analyzed by follow cytometry.

FIG. 16A, FIG. 16B, FIG. 16C, FIG. 16D, FIG. 16E, and FIG. 16F are a series of bar graphs showing changes in mice observed following multidose treatment with ALT-803 and post-treatment recovery.

Figure 17:
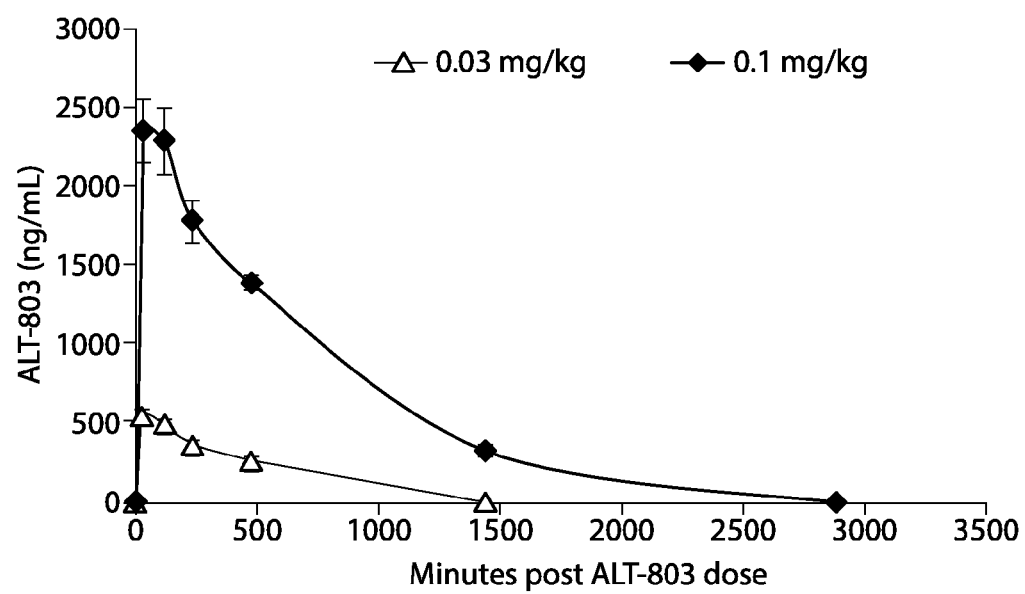
Figure 18A:
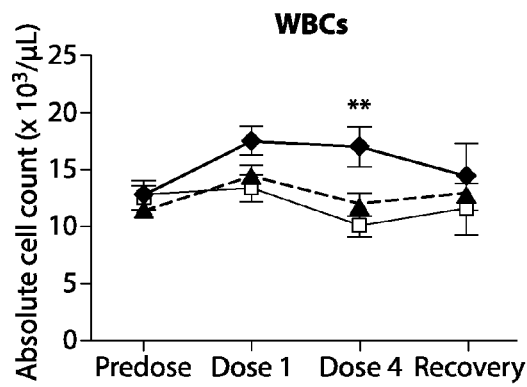
Figure 18B:
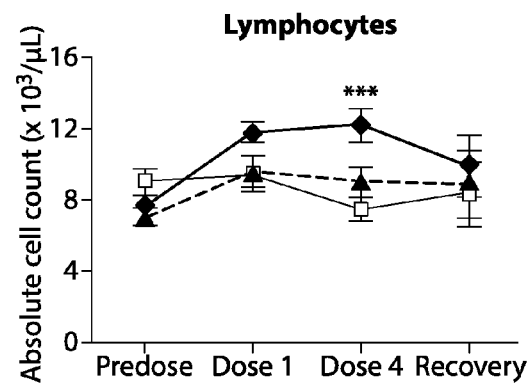
Figure 18C:
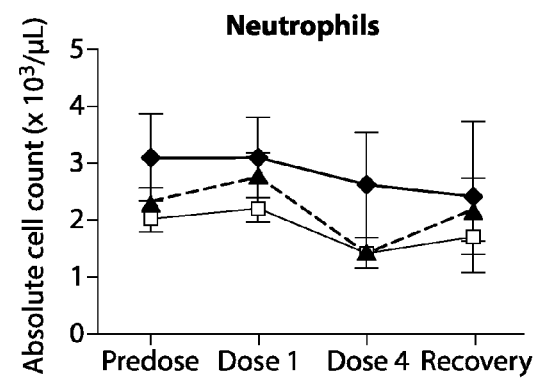
Figure 18D:
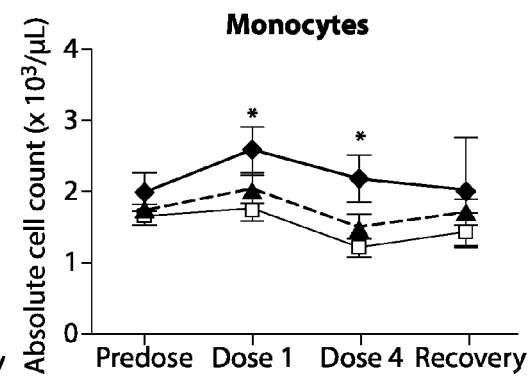
Figure 18E:
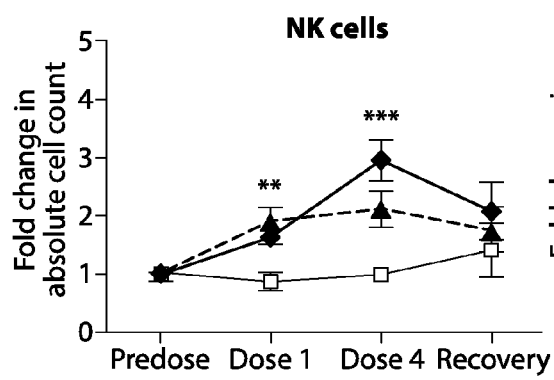
Figure 18F:
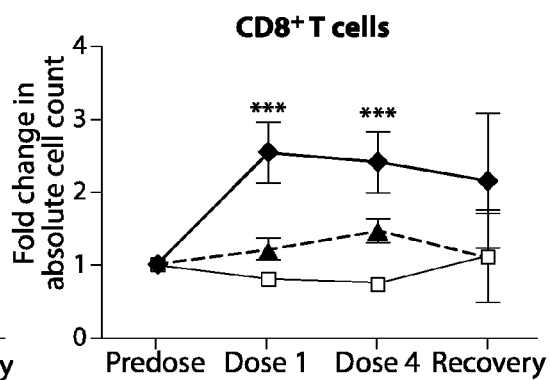
Figure 18G:
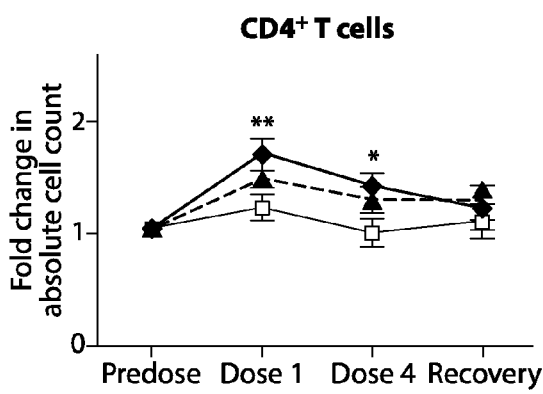
Figure 18H:
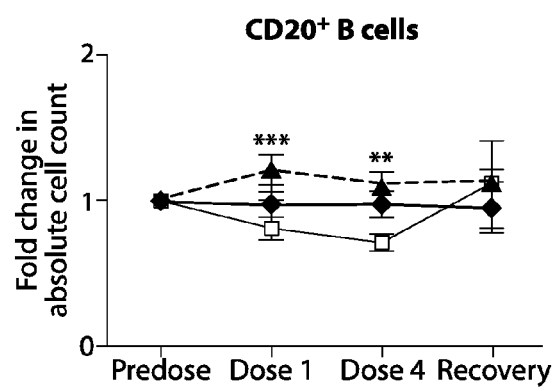

FIG. 17 is a line graph showing the pharmacokinetic profile of ALT-803 in cynomolgus monkeys.

FIG. 18A-FIG. 18H are a series of line graphs showing changes in immune cell counts following multidose ALT-803 treatment and post-treatment recovery in cynomolgus monkeys.

Figure 19A:
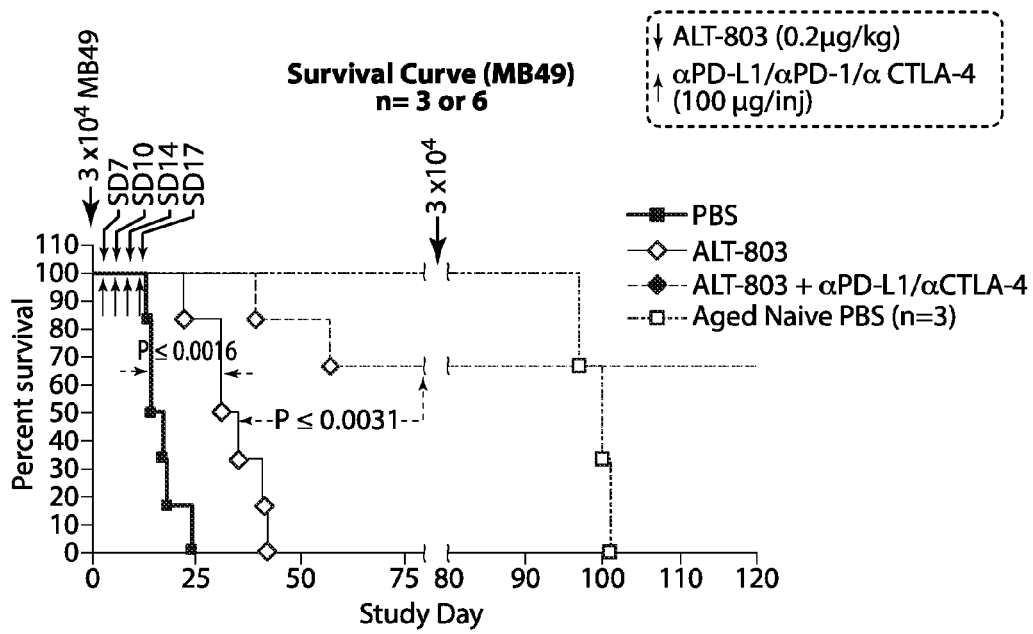
Figure 19B:
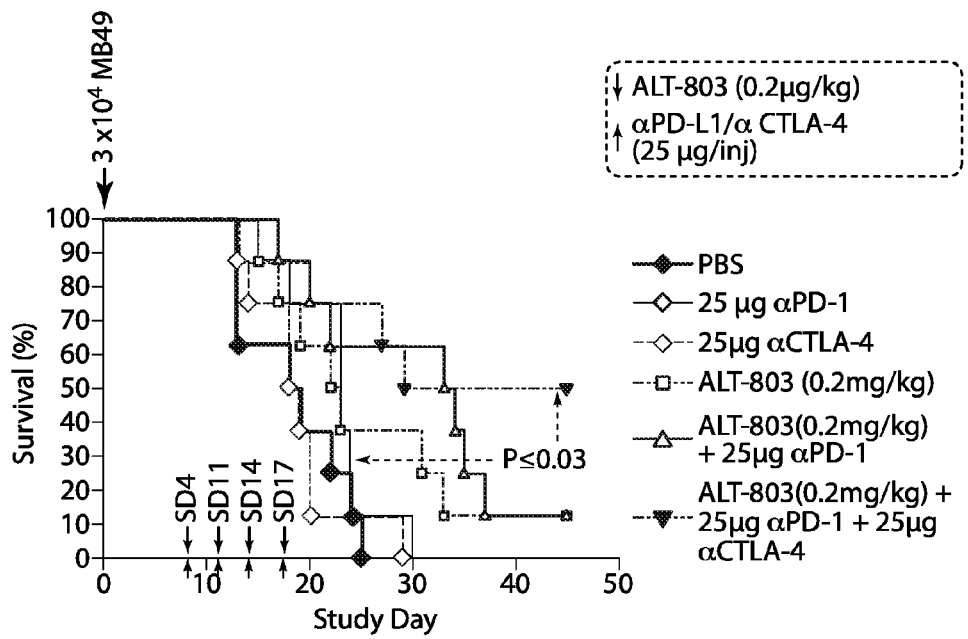

FIG. 19A and FIG. 19B is a series of line graphs showing prolonged survival of mice bearing orthotopic MB49luc bladder tumors following ALT-803 plus checkpoint blockade therapy. In FIG. 19A, C57BL/6 mice bearing orthotopic MB49luc bladder tumors were treated with PBS, ALT-803, and ALT-803 combination therapies with anti-CTLA4 Ab and anti-PD-L1 Ab as indicated in the figure. The survival of the mice was monitored and Kaplan-Meier survival curves were plotted. After 80 days, surviving mice of the ALT-803+anti-PD-L1/anti-CTLA4-Ab group and treatment naïve age-matched mice were re-challenged with intravesicular administration of MB49luc tumor cells. Mouse survival was further monitored. In FIG. 19B, C57BL/6 mice bearing MB49luc bladder tumors were treated with PBS, ALT-803, anti-PD-1 Ab, anti-CTLA-4 Ab or combination therapy as indicated in the figure. The survival of the mice was monitored and Kaplan-Meier survival curves were plotted.

Figure 20:
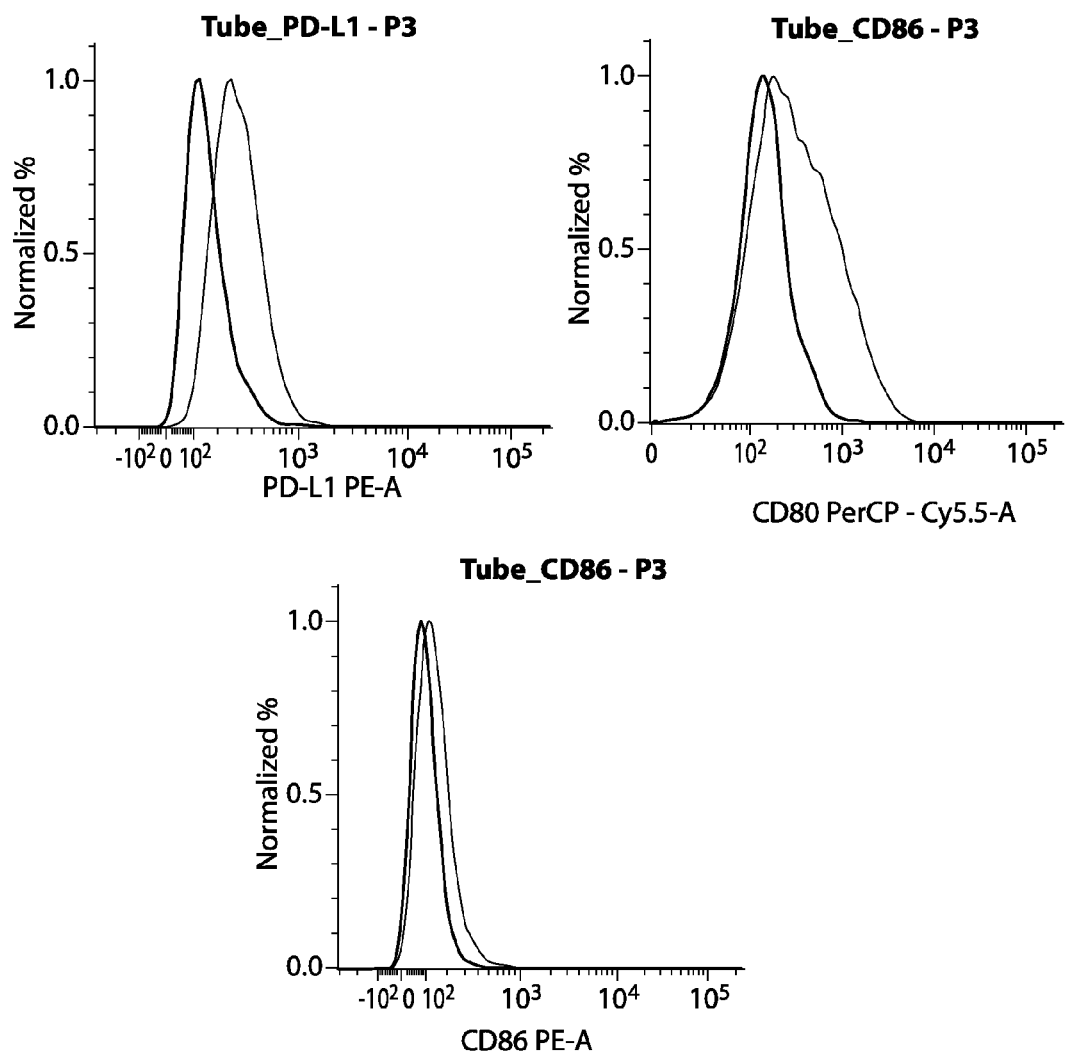

FIG. 20 is a series of flow cytometry graphs showing the expression of ligands for PD1 and CTLA4 on the surface of MB49luc tumor cells. MB49luc tumor cells were stained with antibodies to PD-L1, CD86 and CD80 (blue line) or isotype controls (black line) and then analyzed by follow cytometry.

Figure 21A:
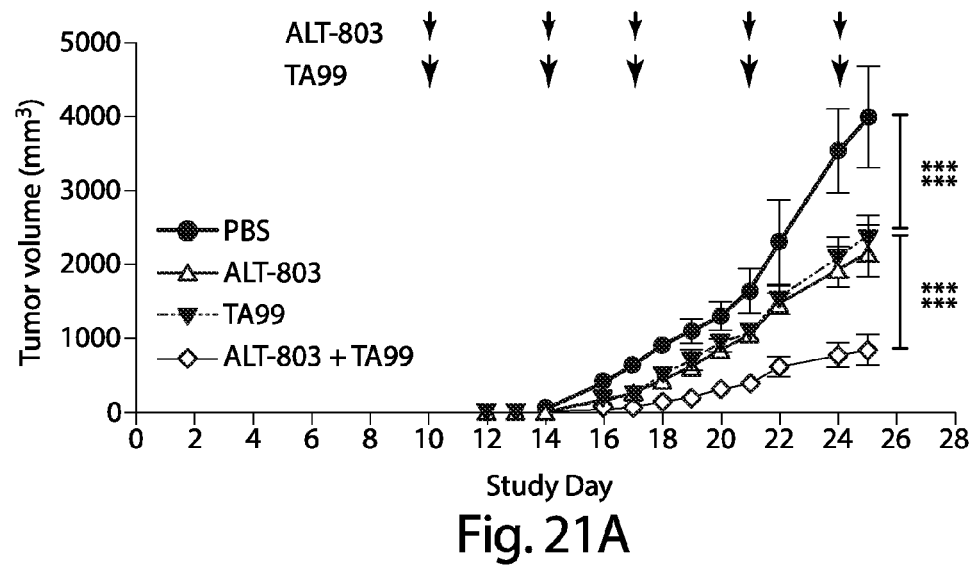
Figure 21B:
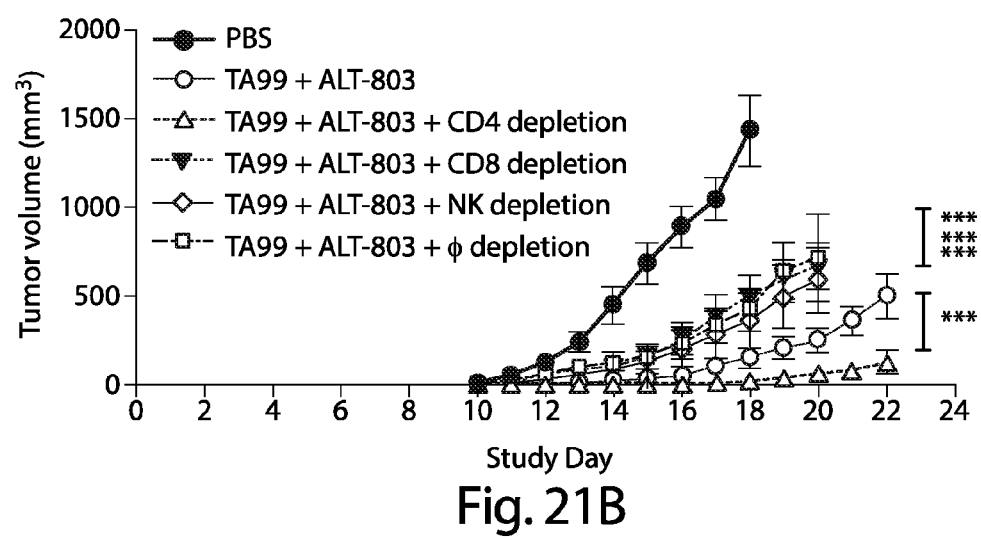
Figure 21C:
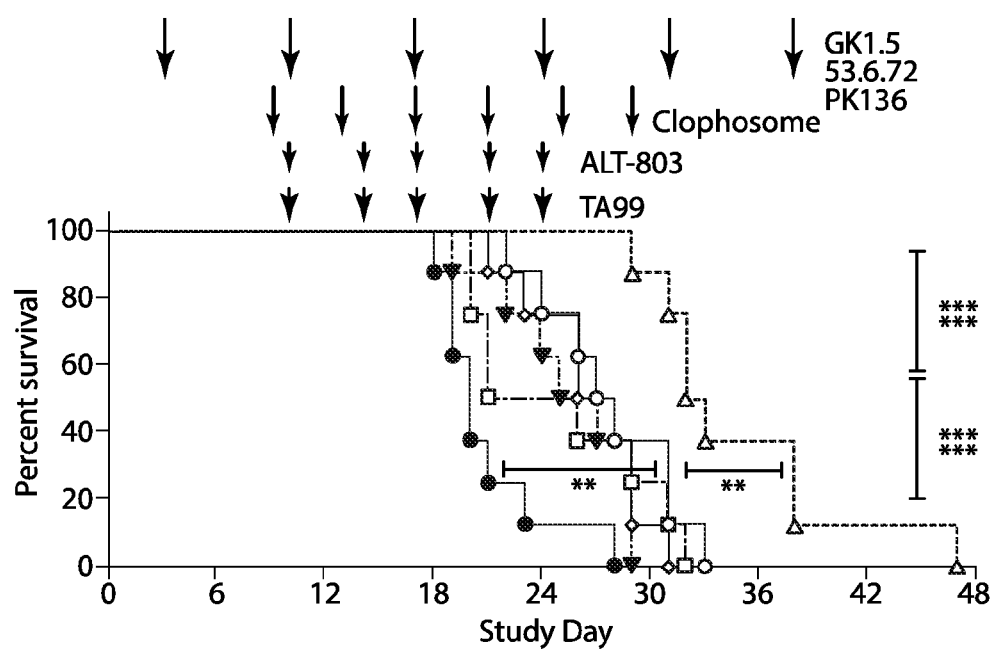

FIG. 21A-FIG. 21C is a series of line graphs showing the combinatorial effect of ALT-803 and TA99 in syngeneic murine melanoma model. In FIG. 21A, B16F10 melanoma cells ($2 \times 10^5$) were injected subcutaneously into the flank of C57BL/6 mice. Once palpable tumors were formed, mice were randomized and treated intravenously with 0.2 mg/kg ALT-803, 10 mg/kg TA99, a combination of ALT-803+TA99, or PBS control on study day 10, 14, 17, 21 and 24.

FIG. 21B and FIG. 21C show the evaluation of the effector functions of different cell subsets involved in the anti-tumor immunity of combined therapy. Depletion of $CD4^+$ and $CD8^+$ T cells was each accomplished by intraperitoneal injection of rat mAb GK1.5 (anti-CD4) and 53.6.72 (anti-CD8a), respectively. NK cell depletion was achieved by intraperitoneal administration of murine mAb PK136 (anti-NK1.1). For the depletion of macrophages, mice were intraperitoneally injected with clodronate-loaded liposomes (Clophosome). The impact of depletion was assessed using both tumor growth (FIG. 21B) and mice survival (FIG. 21C). The survival curves show the study days when animals died due to tumor metastasis or the tumor reached the threshold size (one dimension>20 mm) for tumor burden. n=8/group. : $p<0.01$; *: $p<0.001$.

FIG. 22A-FIG. 22D is a series of bar charts demonstrating ALT-803-mediated increase immune cells in the spleen and tumor microenvironment. In FIG. 22A-FIG. 22D, mice (n=6) were injected (subcutaneously) with B16F10 melanoma cells ($2 \times 10^5$) on study day 0 (SD0) and treated intravenously with TA99, ALT-803, a combination of ALT-803+TA99 or PBS on SD17. On SD20, the percentages of $CD8^+$ T cells ($CD8a^+$), $CD4^+$ T cells ($CD4^+$), NK cells ($panNK^+$), B cells ($CD19^+$), and macrophages ($F4/80^+$) were quantified in splenocytes (FIG. 22A) and TILs ($7\text{-}AAD^- CD45^+$, FIG. 22B) using flow cytometry. The percentages of $CD8^+CD44^{high}$ memory T cells among the $CD8^+$ T cell population of the spleen (FIG. 22C) and TIL (FIG. 22D) were measured and plotted.

Figure 23A:
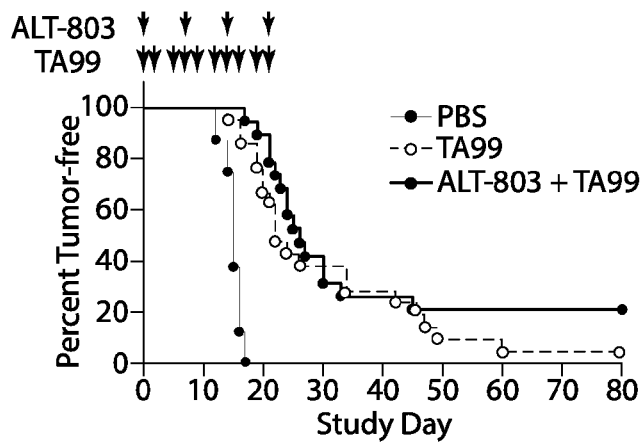
Figure 23B:
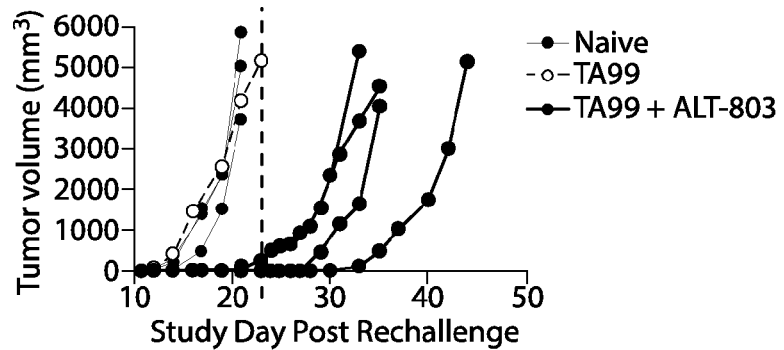
Figure 23C:
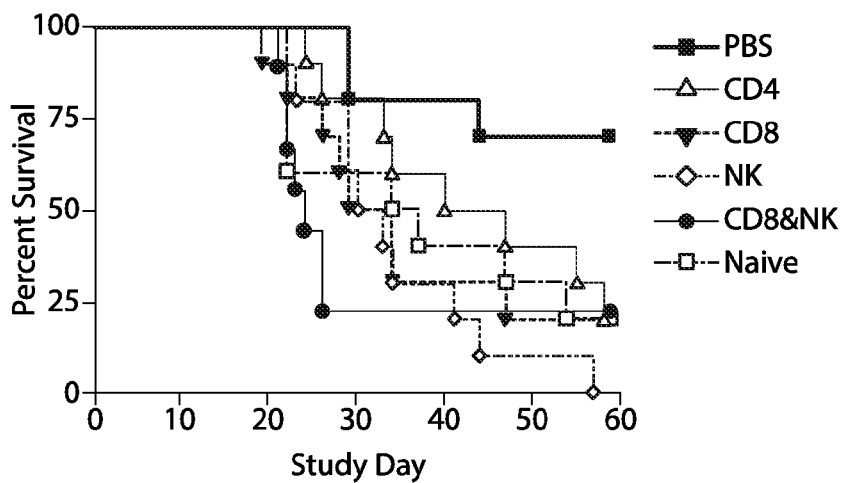

FIG. 23A-FIG. 23C is a series of line graphs demonstrating that ALT-803+TA99 provides immune protection from tumor rechallenge. In FIG. 23A-FIG. 23B, mice (n=20) implanted subcutaneously with B16F10 cells ($2 \times 10^5$) on study day 0 (SD0) were immediately treated intravenously with PBS, TA99, or TA99+ALT-803. After three weeks of treatment and two months of monitoring, naïve and survivor animals were rechallenged contralaterally by subcutaneous injection of B16F10 cells ($2 \times 10^5$). Tumor-free survival (animals maintaining a subcutaneous tumor mass<50 $mm^3$) of animals during initial tumor challenge (FIG. 23A) and tumor growth during rechallenge (FIG. 23B) were measured and plotted. TB=tumor-bearing. *: $p<0.05$; : $p<0.01$; *: $p<0.001$. In FIG. 23C, murine melanoma B16F10 cells ($2 \times 10^5$/mouse) were injected subcutaneously into the flank of C57BL/6 mice on study day −58 (SD-58). The mice were injected with B16F10 cells as in FIG. 23A and treated with ALT-803 (0.2 mg/kg) and TA99 (10 mg/kg) intravenously twice a week for three weeks starting on day 0. To deplete $CD4^+$ T cells, $CD8^+$ T cells, or NK cells, anti-CD4 (GK1.5), anti-CD8 (53-6.72) and/or anti-NK (PK136) were administrated intraperitoneally into the tumor-free mice 46 days post tumor inoculation. In order to assess anti-tumor memory response of the tumor-free mice, B16F10 cells ($2 \times 10^5$/mouse) were subcutaneously injected contralaterally into the tumor free mice 58 days (SD0) post the first tumor inoculation. Treatment naïve mice injected B16F10 cells with served as a control. Survival curve summarizes the study days when animals died due to tumor metastasis or the threshold size (tumor volume>4000 cubic mm). n=10/group.

Figure 24A:
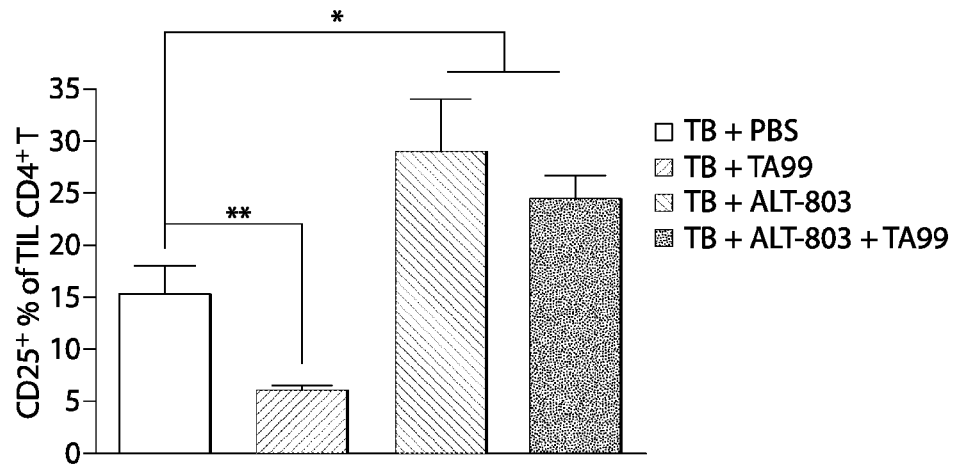
Figure 24B:
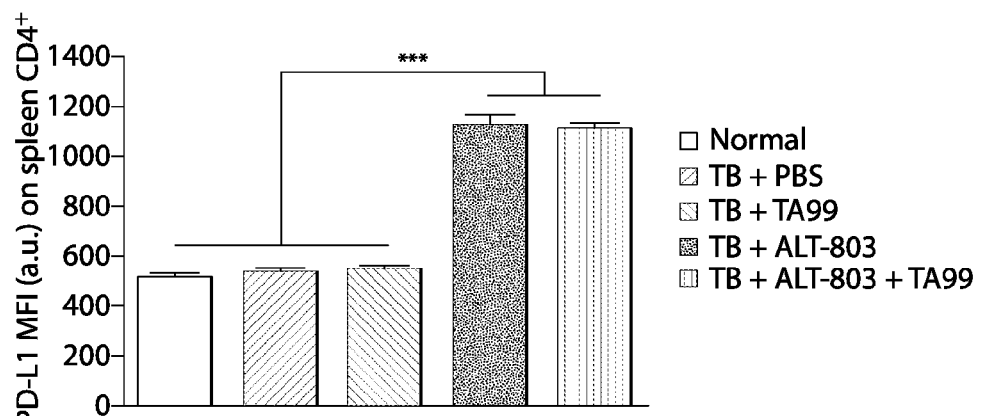
Figure 24C:
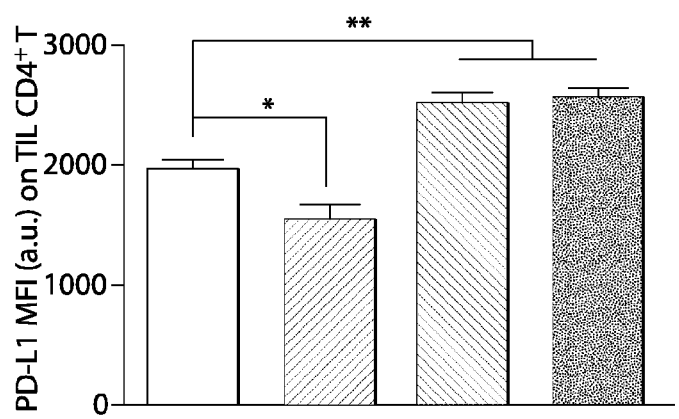
Figure 24D:
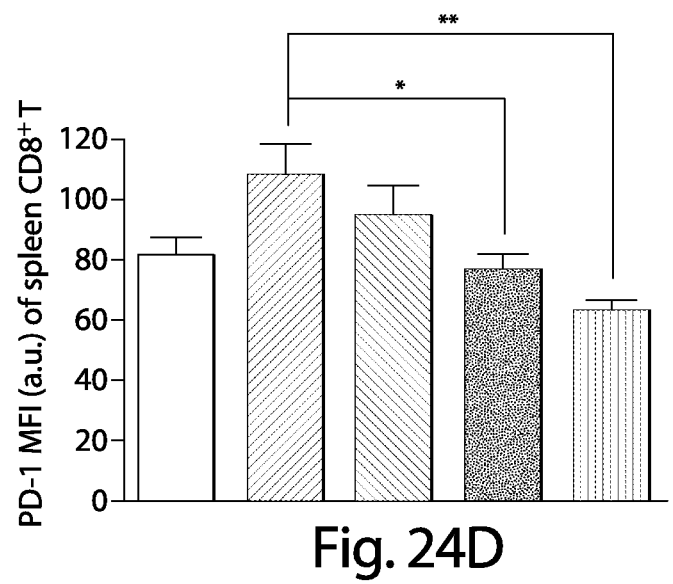
Figure 24E:
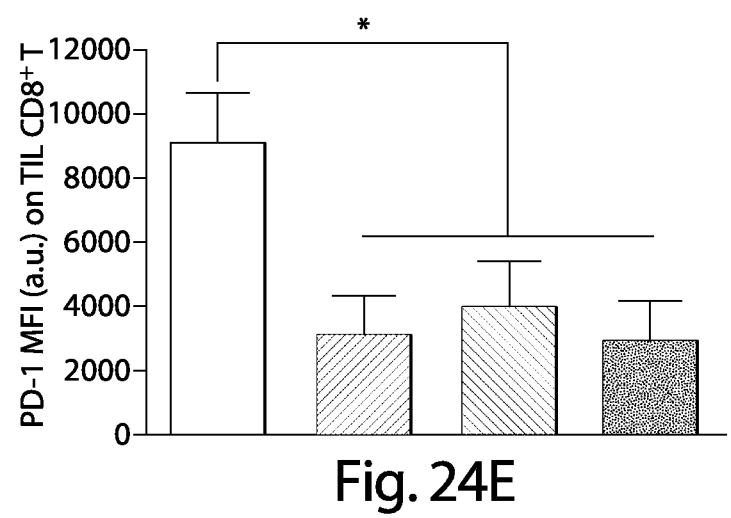

FIG. 24A-FIG. 24E is a series of bar charts showing that ALT-803 activates $CD4^+$ T cells and upregulates their PD-L1 expression, but lowers PD-1 expression on $CD8^+$ T cells. $CD4^+$ T cells ($CD4^+$) from the TIL ($7\text{-}AAD^-CD45^+$) fraction (FIG. 24A) and FIG. 24C) and spleen (FIG. 24B) of tumor-bearing mice (n=6) were stained with anti-CD25 (FIG. 24A) or anti-PD-L1 (FIG. 24B and FIG. 24C) antibodies three days after a single injection of test articles, followed by flow cytometry quantification. CD8$^+$ T cells (CD8$^+$; FIG. 24D and FIG. 24E) from the spleen (FIG. 24D) and TIL (7-AAD$^-$CD45$^+$) fraction (FIG. 24E) of tumor-bearing mice (n=6) were stained with anti-PD-1 (FIG. 24D and FIG. 24E) antibody three days after a single injection of test articles, followed by flow cytometry quantification. Expression of PD-L1 and PD-1 is scored using mean fluorescence intensity (MFI). *: p<0.05; : p<0.01; *: p<0.001.

FIG. 25A-FIG. 25D is a series of bar charts showing that ALT-803 activates NK cells and downregulates PD-1 expression on NK cells. NK cells (panNK$^+$;) from the spleen (FIG. 25A and FIG. 25C) and TIL (7-AAD$^-$CD45$^+$) fraction (FIG. 25B and FIG. 25D) of tumor-bearing mice (n=6) were stained with anti-KLRG1 (FIG. 25A and FIG. 25B) and anti-PD-1 (FIG. 25C and FIG. 25D) antibodies three days after a single injection of test articles, followed by flow cytometry quantification. Expression of KLRG1 and PD-1 is scored using mean fluorescence intensity (MFI). *: p<0.05; : p<0.01; *: p<0.001.

Figure 26A:
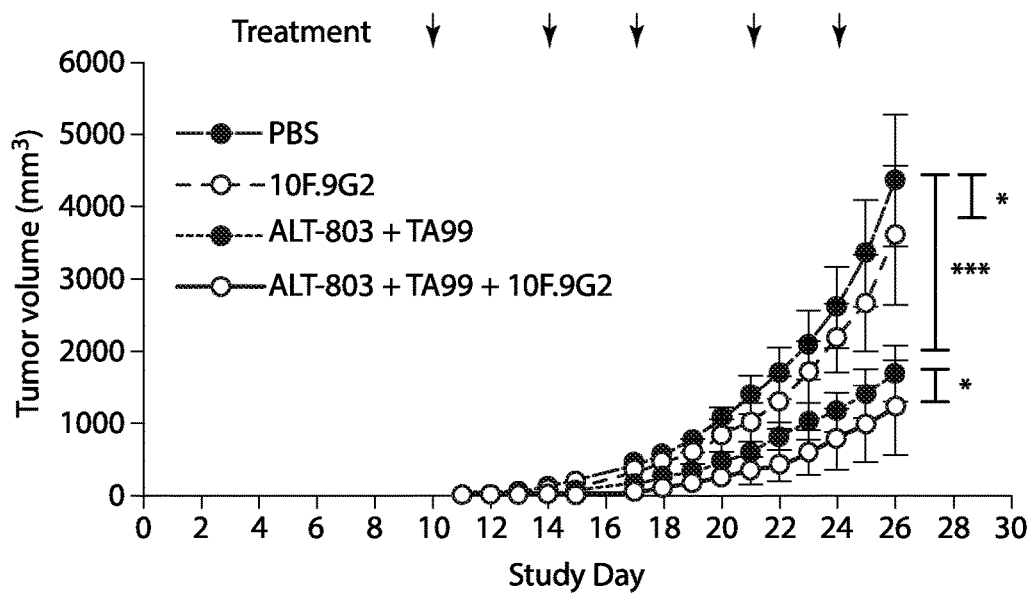
Figure 26B:
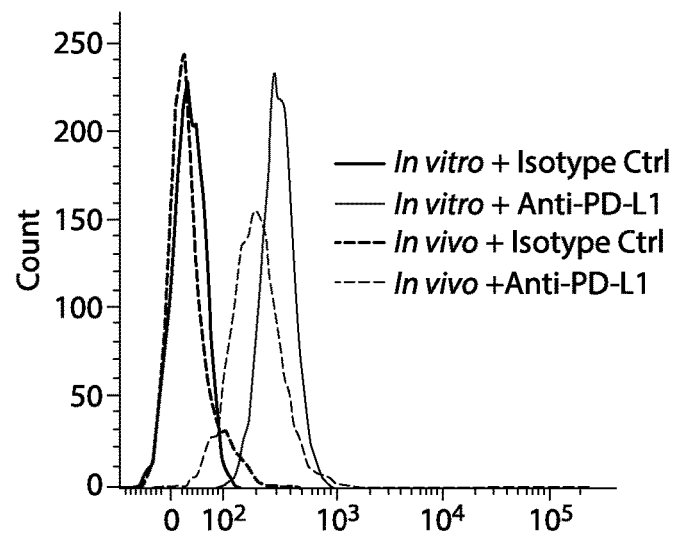

FIG. 26A-FIG. 26B is a series of line graphs showing the combinatorial effect of ALT-803/TA99 and anti-PD-L1 mAb in syngeneic murine melanoma model. In FIG. 26A, B16F10 melanoma cells (2×10$^5$) were injected subcutaneously into the right dorsal flank of C57BL/6 mice. Once palpable tumors were formed, mice were randomized and treated with 0.2 mg/kg ALT-803 (i.v.) and 10 mg/kg TA99 (i.v.), with or without 100 μg/mouse anti-PD-L1 Ab 10F.9G2 (i.p.) on study day 10, 14, 17, 21 and 24. *: p<0.05; ***: p<0.001. FIG. 26B shows in vitro and in vivo expression of PD-L1 on B16F10 cells. B16F10 cells harvested from in vitro culture (solid lines) as well as tumor-bearing mice (dashed lines) were stained with fluorophore-labeled anti-PD-L1 antibody (red) and subjected to flow cytometry. Antibody isotype (black) was included as negative control.

DETAILED DESCRIPTION

The invention is based, at least in part, on the surprising discovery that an antibody in combination with ALT-803, a complex of an interleukin-15 (IL-15) superagonist mutant and a dimeric IL-15 receptor α/Fc fusion protein, is useful for enhancing an immune response against a neoplasia (e.g., a glioblastoma, prostate cancer, hematological cancer, B-cell neoplasms, multiple myeloma, B-cell lymphoma, Hodgkin's lymphoma, acute myeloid leukemia, chronic lymphocytic leukemia, cutaneous T-cell lymphoma, T-cell lymphoma, a solid tumor, urothelial/bladder carcinoma, melanoma, lung cancer, renal cell carcinoma, breast cancer, head and neck cancer, colorectal cancer, and ovarian cancer) or an infection (e.g., an infection with human immunodeficiency virus).

ALT-803

ALT-803 comprises an IL-15 mutant with increased ability to bind IL-2Rβγ and enhanced biological activity (U.S. Pat. No. 8,507,222, incorporated herein by reference). This super agonist mutant of IL-15 was described in a publication (J Immunol 2009 183:3598) and a patent has been issued by the U.S. Patent & Trademark Office on the super agonist and several patents applications are pending (e.g., U.S. Ser. No. 12/151,980 (now U.S. Pat. No. 8,492,118) and Ser. No. 13/238,925 (now U.S. Pat. No. 8,507,222)). This IL-15 super agonist in combination with a soluble IL-15a receptor fusion protein (IL-15RαSu/Fc) results in a protein complex with highly potent IL-15 activity in vitro and in vivo (Han et al., 2011, Cytokine, 56: 804-810; Xu, et al., 2013 Cancer Res. 73:3075-86, Wong, et al., 2013, OncoImmunology 2:e26442). This IL-15 super agonist complex (IL-15N72D: IL-15RαSu/Fc) is referred to as ALT-803. Pharmacokinetic analysis indicated that the complex has a half-life in mice of 25 hours following i.v. administration. ALT-803 exhibits impressive anti-tumor activity against aggressive solid and hematological tumor models in immunocompetent mice. It can be administered as a monotherapy using a twice weekly or weekly i.v. dose regimen or as combinatorial therapy with an antibody. The ALT-803 anti-tumor response is also durable. Tumor-bearing mice that were cured after ALT-803 treatment were also highly resistant to re-challenge with the same tumor cells indicating that ALT-803 induces effective immunological memory responses against the re-introduced tumor cells.

Interleukin-15

Interleukin-15 (IL-15) is an important cytokine for the development, proliferation, and activation of effector NK cells and CD8$^+$ memory T cells. IL-15 binds to the IL-15 receptor α (IL-15Rα) and is presented in trans to the IL-2/IL-15 receptor β-common γ chain (IL-15Rβγ$_c$) complex on effector cells. IL-15 and IL-2 share binding to the IL-15Rβγ$_c$, and signal through STAT3 and STAT5 pathways. However, IL-2 also supports maintenance of CD4$^+$CD25$^+$ FoxP3$^+$ regulatory T (Treg) cells and induces cell death of activated CD8$^+$ T cells. These effects may limit the therapeutic activity of IL-2 against tumors. IL-15 does not share these immunosuppressive activities with IL-2. Additionally, IL-15 is the only cytokine known to provide anti-apoptotic signaling to effector CD8$^+$ T cells. IL-15, either administered alone or as a complex with the IL-15Rα, exhibits potent anti-tumor activities against well-established solid tumors in experimental animal models and, thus, has been identified as one of the most promising immunotherapeutic drugs that could potentially cure cancer.

To facilitate clinical development of an IL-15-based cancer therapeutic, an IL-15 mutant (IL-15N72D) with increased biological activity compared to IL-15 was identified (Zhu et al., J Immunol, 183: 3598-3607, 2009). The pharmacokinetics and biological activity of this IL-15 superagonist (IL-15N72D) was further improved by the creation of IL-15N72D:IL-15RαSu/Fc fusion complex (ALT-803), such that the super agonist complex has at least 25-times the activity of the native cytokine in vivo (Han et al., Cytokine, 56: 804-810, 2011).

Fc Domain

ALT-803 comprises an IL-15N72D:IL-15RαSu/Fc fusion complex. Fusion proteins that combine the Fc regions of IgG with the domains of another protein, such as various cytokines and soluble receptors have been reported (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and C$_{H1}$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15RαSu covalently linked to the Fc portion of the human heavy chain IgG protein have been made (e.g., ALT-803).

The term "Fc" refers to a non-antigen-binding fragment of an antibody. Such an "Fc" can be in monomeric or multimeric form. The original immunoglobulin source of the native Fc is preferably of human origin and may be any of the immunoglobulins, although IgG 1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins.

In some embodiments, the term "Fc variant" refers to a molecule or sequence that is modified from a native Fc, but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) antibody-dependent cell-mediated cytotoxicity (ADCC), or (8) antibody dependent cellular phagocytosis (ADCP). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Fusions Protein Complexes

The invention provides ALT-803, which is a protein complex between IL-15N72D and IL-15RαSu/Fc. In certain embodiments, the ALT-803 polypeptides could serve as a scaffold for fusion to other protein domains. In such fusion protein complexes, a first fusion protein comprises a first biologically active polypeptide covalently linked to interleukin-15 (IL-15) or functional fragment thereof; and the second fusion protein comprises a second biologically active polypeptide covalently linked to soluble interleukin-15 receptor alpha (IL-15Rα) polypeptide or functional fragment thereof, where the IL-15 domain of a first fusion protein binds to the soluble IL-15Rα domain of the second fusion protein to form a soluble fusion protein complex. Fusion protein complexes of the invention also comprise immunoglobulin Fc domain or a functional fragment thereof linked to one or both of the first and second fusion proteins. Preferably, the Fc domains linked to the first and second fusion proteins interact to form a fusion protein complex. Such a complex may be stabilized by disulfide bond formation between the immunoglobulin Fc domains. In certain embodiments, the soluble fusion protein complexes of the invention include an IL-15 polypeptide, IL-15 variant or a functional fragment thereof and a soluble IL-15Rα polypeptide or a functional fragment thereof, wherein one or both of the IL-15 and IL-15Rα polypeptides further include an immunoglobulin Fc domain or a functional fragment thereof.

In a further embodiment, one or both of the first and second biologically active polypeptides comprises an antibody or functional fragment thereof.

In another embodiment, the antigen for the antibody domain comprises a cell surface receptor or ligand.

In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

As used herein, the term "biologically active polypeptide" or "effector molecule" is meant an amino acid sequence such as a protein, polypeptide or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptides or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same.

Covalently linking the effector molecule to the fusion protein complexes of the invention in accordance with the invention provides a number of significant advantages. Fusion protein complexes of the invention can be produced that contain a single effector molecule, including such a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of a the fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins and antibodies disclosed herein, e.g., effector molecule conjugates such as cytokines, chemokines, growth factors, protein toxins, immunoglobulin domains or other bioactive molecules and any peptide linkers, can be organized in nearly any fashion provided that the fusion protein or antibody has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein.

Pharmaceutical Therapeutics

The invention provides pharmaceutical compositions comprising ALT-803 for use as a therapeutic. In one aspect, ALT-803 is administered systemically, for example, formulated in a pharmaceutically-acceptable buffer such as physiological saline. Preferable routes of administration include, for example, instillation into the bladder, subcutaneous, intravenous, intraperitoneal, intramuscular, or intradermal injections that provide continuous, sustained levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia or infection. Generally, amounts will be in the range of those used for other agents used in the treatment of other diseases associated with neoplasia or infection, although in certain instances lower amounts will be needed because of the increased specificity of the compound. A compound is administered at a dosage that enhances an immune response of a subject, or that reduces the proliferation, survival, or invasiveness of a neoplastic cell as determined by a method known to one skilled in the art. Alternatively, the compound is administered at a dosage that reduces infection by a virus or other pathogen of interest.

Formulation of Pharmaceutical Compositions

The administration of ALT-803 for the treatment of a neoplasia or an infection may be by any suitable means that results in a concentration of the therapeutic that, combined with other components, is effective in ameliorating, reducing, or stabilizing a neoplasia or infection. ALT-803 may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, intravesicularly or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice or nonhuman primates, as a skilled artisan recognizes it is routine in the art to modify the dosage for humans compared to animal models. In certain embodiments it is envisioned that the dosage may vary from between about 0.1 μg compound/kg body weight to about 5000 μg compound/kg body weight; or from about 1 μg/kg body weight to about 4000 μg/kg body weight or from about 10 μg/kg body weight to about 3000 μg/kg body weight. In other embodiments this dose may be about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 μg/kg body weight. In other embodiments, it is envisaged that doses may be in the range of about 0.5 μg compound/kg body weight to about 20 μg compound/kg body weight. In other embodiments the doses may be about 0.5, 1, 3, 6, 10, or 20 mg/kg body weight. Of course, this dosage amount may be adjusted upward or downward, as is routinely done in such treatment protocols, depending on the results of the initial clinical trials and the needs of a particular patient.

In particular embodiments, ALT-803 are formulated in an excipient suitable for parenteral administration. In particular embodiments, ALT-803 is administered at 0.5 μg/kg-about 15 μg/kg (e.g., 0.5, 1, 3, 5, 10, or 15 μg/kg).

For the treatment of bladder cancer, ALT-803 is administered by instillation into the bladder. Methods of instillation are known. See, for example, Lawrencia, et al., Gene Ther 8, 760-8 (2001); Nogawa, et al., J Clin Invest 115, 978-85 (2005); Ng, et al., Methods Enzymol 391, 304-13 2005; Tyagi, et al., J Urol 171, 483-9 (2004); Trevisani, et al., J Pharmacol Exp Ther 309, 1167-73 (2004); Trevisani, et al., Nat Neurosci 5, 546-51 (2002)); (Segal, et al., 1975). (Dyson, et al., 2005). (Batista, et al., 2005; Dyson, et al., 2005). In certain embodiments, it is envisioned that the ALT-803 dosage for instillation may vary from between about 5 and 1000 μg/dose. In other embodiments the intravesical doses may be about 25, 50, 100, 200, or 400 μg/dose. In other embodiments, ALT-803 is administered by instillation into the bladder in combination with standard therapies, including mitomycin C or Bacille Calmette-Guerin (BCG).

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition comprising ALT-803 may be administered parenterally by injection, infusion or implantation (subcutaneous, intravenous, intramuscular, intravesicularly, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising ALT-803 for parenteral use may be provided in unit dosage forms (e.g., in single-dose ampoules, syringes or bags), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia or infection, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions comprising ALT-803 may be in a form suitable for sterile injection. To prepare such a composition, the suitable active antineoplastic/anti-infective therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The present invention provides methods of treating neoplastic or infectious disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic or infectious disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic or infectious disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). ALT-803 may be used in the treatment of any other disorders in which an increase in an immune response is desired.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia or infection in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Preferably, ALT-803 is administered in combination with an anti-neoplasia or anti-infectious therapeutic such as an antibody, e.g., a tumor-specific antibody or an immune-checkpoint inhibitor. The antibody and ALT-803 may be administered simultaneously or sequentially. In some embodiments, the antibody treatment is an established therapy for the disease indication and addition of ALT-803 treatment to the antibody regimen improves the therapeutic benefit to the patients. Such improvement could be measured as increased responses on a per patient basis or increased responses in the patient population. Combination therapy could also provide improved responses at lower or less frequent doses of antibody resulting in a better tolerated treatment regimen. As indicated, the combined therapy of ALT-803 and an antibody could provide enhances clinical activity through various mechanisms, including augmented ADCC, ADCP, and/or NK cell, T-cell, neutrophil or monocytic cell levels or immune responses.

If desired, ALT-803 is administered in combination with any conventional therapy, including but not limited to, surgery, radiation therapy, chemotherapy, protein-based therapy or biological therapy. Chemotherapeutic drugs include alkylating agents (e.g., platinum-based drugs, tetrazines, aziridines, nitrosoureas, nitrogen mustards), anti-metabolites (e.g., anti-folates, fluoropyrimidines, deoxynucleoside analogues, thiopurines), anti-microtubule agents (e.g., *vinca* alkaloids, taxanes), topoisomerase inhibitors (e.g., topoisomerase I and II inhibitors), cytotoxic antibiotics (e.g., anthracyclines) and immunomodulatory drugs (e.g., thalidomide and analogs).

Kits or Pharmaceutical Systems

Pharmaceutical compositions comprising ALT-803 may be assembled into kits or pharmaceutical systems for use in treating a neoplasia or infection. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using ALT-803.

Recombinant Protein Expression

In general, preparation of the fusion protein complexes of the invention (e.g., components of ALT-803) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, COS or preferably CHO cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transfection and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein) raised against the polypeptide may be attached to a column and used to isolate the recombinant polypeptide. Lysis and fractionation of polypeptide-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980).

As used herein, biologically active polypeptides or effector molecules of the invention may include factors such as cytokines, chemokines, growth factors, protein toxins, immunoglobulin domains or other bioactive proteins such as enzymes. Also biologically active polypeptides may include conjugates to other compounds such as non-protein toxins, cytotoxic agents, chemotherapeutic agents, detectable labels, radioactive materials and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-1, IL-17, TGF and TNF cytokine families, and to IL-1 through IL-35, IFN-α, IFN-β, IFNγ, TGF-β, TNF-α, and TNFβ.

In an aspect of the invention, the first fusion protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL-2, although fundamental differences have been well characterized (Waldmann, T A, 2006, Nature Rev. Immunol. 6:595-601).

In another aspect of the invention, the first fusion protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rα polypeptide and functions as an IL-15 agonist or antagonist. Preferably, IL-15 variants with agonist activity have super agonist activity. In some embodiments, the IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some embodiments, the sequence of the IL-15 variant has at least one amino acid change, e.g. substitution or deletion, compared to the native IL-15 sequence, such changes resulting in IL-15 agonist or antagonist activity. Preferably the amino acid substitutions/deletions are in the domains of IL-15 that interact with IL-15Rβ and/or γC. More preferably, the amino acid substitutions/deletions do not affect binding to the IL-15Rα polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally suitable amino acid substitutions can be conservative or non-conservative changes and insertions of additional amino acids. Preferably, IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 variants with antagonist activity and N72D substitutions result in IL-15 variants with agonist activity.

Chemokines, similar to cytokines, are defined as any chemical factor or molecule which when exposed to other cells are responsible for any of a number of multiple effects of cellular immunity. Suitable chemokines may include but are not limited to the CXC, CC, C, and CX.sub.3C chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, *pseudomonas* exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; a phosphorescent or chemiluminescent molecules or a label detectable by PET, ultrasound or MRI such as Gd- or paramagnetic metal ion-based contrast agents. See e.g., Moskaug, et al. J. Biol. Chem. 264, 15709 (1989); Pastan, I. et al. Cell 47, 641, 1986; Pastan et al., Recombinant Toxins as Novel Therapeutic Agents, Ann. Rev. Biochem. 61, 331, (1992); "Chimeric Toxins" Olsnes and Phil, Pharmac. Ther., 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

A protein fusion or conjugate complex that includes a covalently linked IL-15 and IL-15Rα domains has several important uses. Cells or tissue susceptible to being damaged or killed can be readily assayed by the methods disclosed herein.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammal. Sequences of these polypeptides and encoding nucleic acids are known in the literature, including human interleukin 15 (IL15) mRNA—GenBank: U14407.1, Mus musculus interleukin 15 (IL15) mRNA—GenBank: U14332.1, human interleukin-15 receptor alpha chain precursor (IL15RA) mRNA—GenBank: U31628.1, Mus musculus interleukin 15 receptor, alpha chain—GenBank: BC095982.1.

In some settings, it can be useful to make the protein fusion or conjugate complexes of the present invention polyvalent, e.g., to increase the valency of the sc-TCR or sc-antibody. In particular, interactions between the IL-15 and IL-15Rα domains of the fusion protein complex provide a means of generating polyvalent complexes. In addition, the polyvalent fusion protein can made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to nanoparticles) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein or antibody, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable nanoparticle to give a multivalent molecule. Exemplary nanoparticles include dendrimers, liposomes, core-shell particles or PLGA-based particles.

In another embodiment of the invention, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 $C_{H2}$-$C_{H3}$, are capable of stably interacting to create the Fc region. Preferred immunoglobulin domains including Fc domains also comprise regions with effector functions, including Fc receptor or complement protein binding activity, and/or with glycosylation sites. In some embodiments, the immunoglobulin domains of the fusion protein complex contain mutations that reduce or augment Fc receptor or complement binding activity or glycosylation, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present proteins (e.g., components of ALT-803). Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See, Sambrook et al., supra and Ausubel et al. supra.

Included in the invention are methods for making a soluble fusion protein complex, the method comprising introducing into a host cell a DNA vector as described herein encoding the first and second fusion proteins, culturing the host cell in media under conditions sufficient to express the fusion proteins in the cell or the media and allow association between IL-15 domain of a first fusion protein and the soluble IL-15Rα domain of a second fusion protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50° C., 6×SSC (sodium chloride/sodium citrate buffer) and 0.1% SDS (sodium dodecyl sulfate) indicate about 60-70% homology, hybridization and wash conditions of 50-65° C., 1×SSC and 0.1% SDS indicate about 82-97% homology, and hybridization and wash conditions of 52° C., 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See, e.g., Means, G. E. and Feeney, R. E. (1974) in *Chemical Modification of Proteins*, Holden-Day. See also, S. S. Wong (1991) in *Chemical of Protein Conjugation and Cross-Linking*, CRC Press. However it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express ALT-803. For example, a construct encoding ALT-803 can be incorporated into a suitable vector using restriction enzymes to make cuts in the vector for insertion of the construct followed by ligation. The vector containing the gene construct is then introduced into a suitable host for expression of the fusion protein. See, generally, Sambrook et al., supra. Selection of suitable vectors can be made empirically based on factors relating to the cloning protocol. For example, the vector should be compatible with, and have the proper replicon for the host that is being employed. The vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See, Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immunoblotting. Other methods for detecting expression of fusion proteins comprising biologically active polypeptides linked to IL-15 or IL-15Rα domains are disclosed in the Examples.

As mentioned generally above, a host cell can be used for preparative purposes to propagate nucleic acid encoding a desired fusion protein. Thus, a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA,* 77:4216 (1980)), 293 cells (Graham et al., *J Gen. Virol.,* 36:59 (1977)) or myeloma cells like SP2 or NSO (Galfre and Milstein, *Meth. Enzymol.,* 73(B):3 (1981)).

Host cells capable of propagating nucleic acid encoding a desired fusion protein comples encompass non-mammalian eukaryotic cells as well, including insect (e.g., Sp. *frugiperda*), yeast (e.g., *S. cerevisiae, S. pombe, P. pastoris., K lactis, H. polymorpha*; as generally reviewed by Fleer, R., *Current Opinion in Biotechnology,* 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream protein sequence.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His⁻ *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of E. coli. Numerous cloning vectors suitable for construction of the expression construct are known in the art (λZAP and pBLUESCRIPT SK-1, Stratagene, La Jolla, Calif., pET, Novagen Inc., Madison, Wis., cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into S. cerevisiae cells by protoplast transformation or electroporation. Electroporation of S. cerevisiae is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion complex. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultrafiltration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

The present fusion protein complexes are suitable for in vitro or in vivo use with a variety of cells that are cancerous or are infected or that may become infected by one or more diseases.

Human interleukin-15 (hIL-15) is trans-presented to immune effector cells by the human IL-15 receptor α chain (hIL-15Rα) expressed on antigen presenting cells. IL-15Rα binds hIL-15 with high affinity (38 pM) primarily through the extracellular sushi domain (IL-15RαSu). As described herein, the IL-15 and IL-15RαSu domains can be used to generate a soluble complex (e.g., ALT-803) or as a scaffold to construct multi-domain fusion complexes.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcomes for a number of different autoimmune indications.

In addition to its dimerization activity, the Fc fragment also provides cytotoxic effector functions through the complement activation and interaction with Fcγ receptors displayed on natural killer (NK) cells, neutrophils, monocyte cells, phagocytes and dendritic cells. In the context of anti-cancer therapeutic antibodies and other antibody domain-Fc fusion proteins, these activities likely play an important role in efficacy observed in animal tumor models and in cancer patients. However these cytotoxic effector responses may not be sufficient in a number of therapeutic applications. Thus, there has been considerable interest in improving and expanding on the effector activity of the Fc domain and developing other means of increasing the activity or recruitment of cytolytic immune responses, including NK cells and T cells at the disease site via immunotherapeutic molecules.

In an effort to develop human-derived immunostimulatory therapeutic, human IL-15 (hIL-15) and IL-15 receptor domains were used. hIL-15 is a member of the small four α-helix bundle family of cytokines that associates with the hIL-15 receptor α-chain (hIL-15Rα) with a high binding affinity (Equilibrium dissociation constant (KD) ~$10^{-11}$ M). The resulting complex is then trans-presented to the human IL-2/15 receptor β/common γ chain (hIL-15RβγC) complexes displayed on the surface of T cells and NK cells. This cytokine/receptor interaction results in expansion and activation of effector T cells and NK cells, which play an important role in eradicating virally infected and malignant cells. Normally, hIL-15 and hIL-15Rα are co-produced in dendritic cells to form complexes intracellularly that are subsequently secreted and displayed as heterodimeric molecules on cell surfaces. Thus, the characteristics of hIL-15 and hIL-15Rα interactions suggest that these inter chain binding domains could serve as a human-derived immunostimulatory complex and as a scaffold to make soluble dimeric molecules capable of target-specific binding.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: Induction of Lymphocyte Proliferation and Activation by ALT-803

Human blood buffy coats from normal individuals were used to isolate peripheral blood mononuclear cells (PBMCs) with Histopaque-1077. PBMCs were cultured at 37° C. with 5% CO$_2$ in RPMI-10 medium (RPMI-1640, 2-mercaptoethanol, penicillin-streptomycin-glutamine, non-essential amino acids, sodium pyruvate, and 10% fetal bovine serum) with the various amounts of ALT-803. By "ALT-803" is meant a complex comprising IL-15N72D noncovalently associated with a dimeric IL-15RαSu/Fc fusion protein, wherein said complex exhibits immune stimulating activity. Optionally, the IL-15N72D and/or IL-15RαSu/Fc fusion protein comprises one, two, three, four or more amino acid variations relative to a reference sequence. An exemplary IL-15N72D amino acid sequence is provided below. (See, e.g., U.S. Ser. No. 13/769,179 (now U.S. Pat. No. 9,255, 141), incorporated herein by reference).

An exemplary IL-15N72D nucleic acid sequence is provided below (with leader peptide) (SEQ ID NO: 1):

```
(Leader peptide)
atggagacagacacactcctgttatgggtactgctgctctgggttccagg ttccaccggt- (IL-15N72D)
aactgggtgaatgtaataagtgatttgaaaaaaattgaagatcttattca atctatgcatattgatgctactttatatacggaaagtgatgttcacccca gttgcaaagtaacagcaatgaagtgctttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaattttg
                                       (Stop codon)
cagagtttgtacatattgtccaaatgttcatcaacacttcttaa
```

An exemplary IL-15N72D amino acid sequence is provided below (with leader peptide) (SEQ ID NO: 2):

```
(Leader peptide)
METDTLLLWVLLLWVPGSTG- (IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS
```

In some cases, the leader peptide is cleaved from the mature IL-15N72D polypeptide (SEQ ID NO: 3):

```
(IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS
```

An exemplary IL-15RαSu/Fc nucleic acid sequence (with leader peptide) is provided below (SEQ ID NO: 4):

```
(Leader peptide)
atggacagacttacttcttcattcctgctcctgattgtccctgcgtacgt cttgtcc- (IL-15RaSu)
atcacgtgccctcccccatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgtattaga- (IgG1 CH2-CH3 (Fc domain))
gagcccaaatcttgtgacaaaactcacacatgcccaccgtgcccagcacc tgaactcctggggggaccgtcagtcttcctcttccccccaaaacccaagg acacctcatgatctcccggacccctgaggtcacatgcgtggtggtggac gtgagccacgaagaccctgaggtcaagttcaactggtacgtggacggcgt ggaggtgcataatgccaagacaaagccgcggaggagcagtacaacagca cgtaccgtgtggtcagcgtcctcaccgtcctgcaccaggactggctgaat ggcaaggagtacaagtgcaaggtctccaacaaagccctcccagccccat
```

```
-continued
cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc aggtggcagcagggaacgtcttctcatgctccgtgatgcatgaggctct gcacaaccactacacgcagaagagcctctccctgtctccgggtaaa- (Stop codon)
taa
```

An exemplary IL-15RαSu/Fc amino acid sequence (with leader peptide) is provided below (SEQ ID NO: 5):

```
(Leader peptide)
MDRLTSSFLLLIVPAYVLS- (IL-15RaSu)
ITCPPPMSVEHADIWVKSYSLYSRERYICNSGFKRKAGTSSLTECVLNKA

TNVAHWTTPSLKCIR- (IgG1 CH2-CH3 (Fc domain))
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

In some cases, the mature IL-15RαSu/Fc protein lacks the leader sequence (SEQ ID NO: 6):

```
(IL-15RaSu)
ITCPPPMSVEHADIWVKSYSLYSRERYICNSGFKRKAGTSSLTECVLNKA

TNVAHWTTPSLKCIR- (IgG1 CH2-CH3 (Fc domain))
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

To assess lymphocyte subset proliferation and activation, ALT-803-treated cells were stained with either a combination of Brilliant Violet 510-anti-CD4, PECY7-anti-CD8, and Brilliant Violet 421-anti-CD16 antibodies for surface markers, followed by intracellular staining with FITC-anti-granzyme B antibody or a combination of Brilliant Violet-anti-CD4, PE-anti-CD8, PECY7-anti-CD335, PerCP-CY5.5-anti-CD69 and APC-anti-CD25 antibodies for surface markers, followed by intracellular staining with FITC-anti-perforin antibody. For intracellular staining, the cells were fixed with fixation buffer (PBS with 2% paraformaldehyde) and incubated at room temperature for 20 minutes. The fixed cells were permeabilized in Permeabilization Buffer (PBS with 0.1% saponin and 0.05% sodium azide) and stained with FITC-labeled antibodies specific to human granzyme B or perforin. The percentage of $CD4^+$ T cells, $CD8^+$ T cells and $CD16^+$ NK cells in the ALT-803-activated PBMCs, and the expression of CD25 and CD69 activation markers on $CD4^+$ T cells, $CD8^+$ T cells and $CD335^+$ NK cells were analyzed on a FACSVerse flow cytometer using FACSuite software.

Figure 1A:
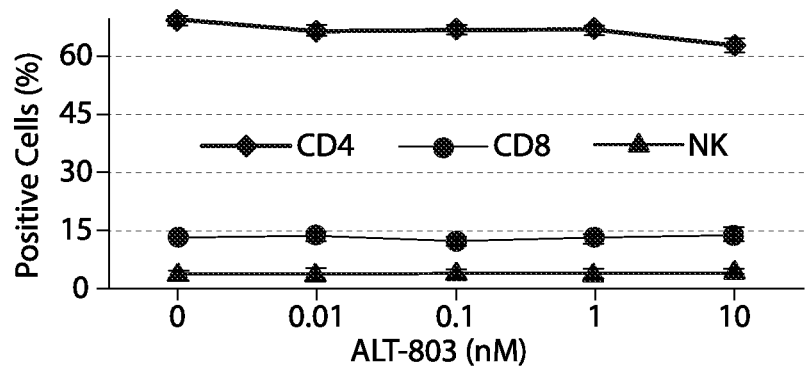
FIG. 1A-FIG. 1F are a series of line graphs demonstrating the effects of ALT-803 on in vitro proliferation of human immune cell subsets. Human PBMCs were separated from blood buffy coats of two healthy donors (Donor-A, FIG. 1A, FIG. 1C, and FIG. 1E; Donor-B, FIG. 1B, FIG. 1D and FIG. 1F) and cultured in RPMI-10 with or without ALT-803 for 5 days (FIG. 1A and FIG. 1B) or the indicated times (FIG. 1C, FIG. 1D, FIG. 1E and FIG. 1F). ALT-803 was added at the concentrations indicated in FIG. 1A and FIG. 1B, and at 10 nM with RPMI-10 serving as a medium control (Ctrl) for the studies shown in FIG. 1C-FIG. 1F. At the end of the incubation, PBMCs were stained with fluorochrome-labeled antibodies specific to CD4, CD8 (as markers for T cells) and CD16 (as a marker of NK cells). The percentages of the cell subsets were analyzed on a FACSverse with FACSuite software. Triplicate samples from individual donors were analyzed for FIG. 1A and FIG. 1B and single samples for each timepoint were analyzed for FIG. 1C and FIG. 1D.
Figure 1B:
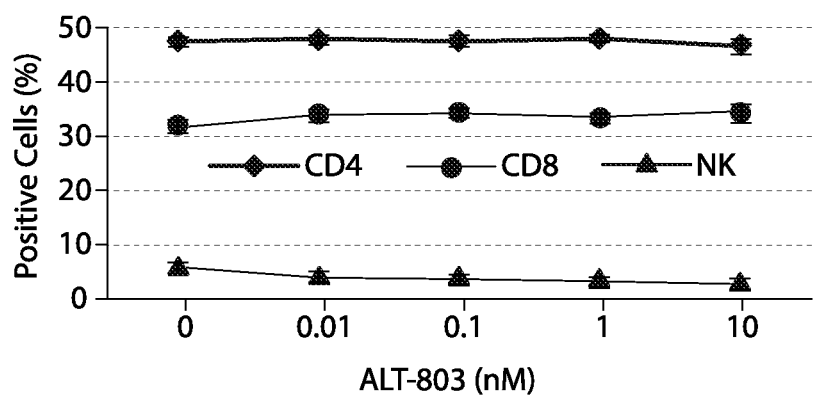
Figure 1C:
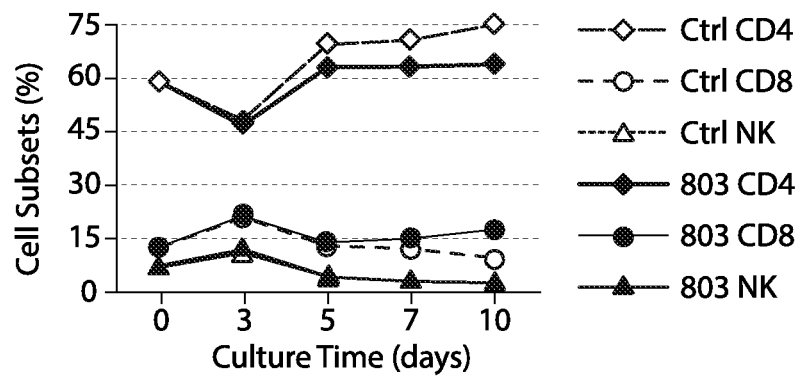
Figure 1D:
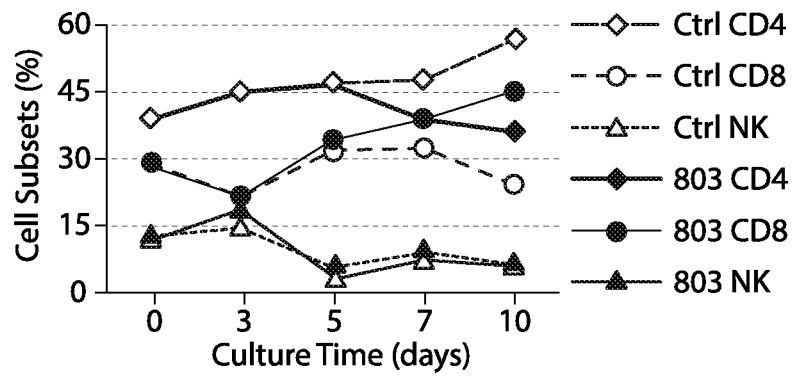
Figure 1E:
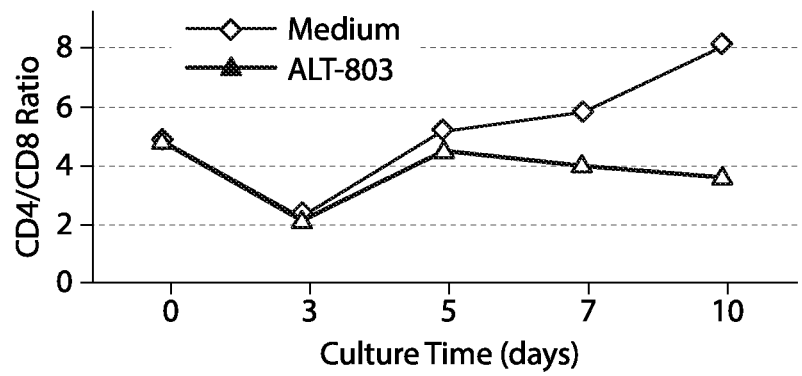
Figure 1F:
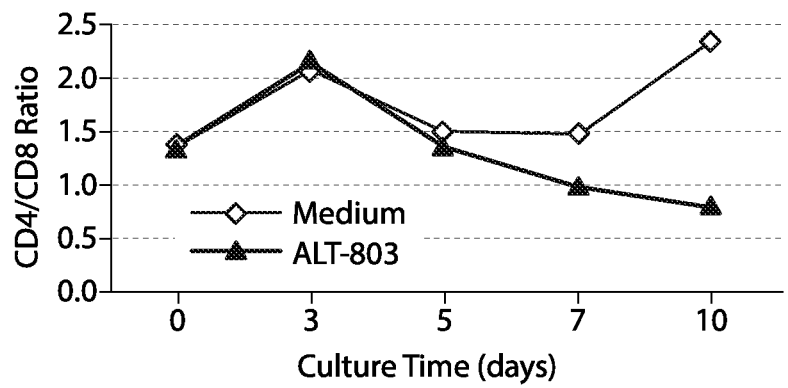

There was no significant change in the percentage of $CD4^+$ T cells, $CD8^+$ T cells or NK cells in the human PBMCs from different donors following 5 days of incubation in medium containing 0.01 to 10 nM ALT-803 compared with medium control (FIG. 1A and FIG. 1B). Since previous studies have shown that ALT-803 can stimulate proliferative responses of human PMBCs in vitro, the incubation time of the culture was extended to increase the sensitivity of this assay. As shown in FIG. 1C (Donor-A) and FIG. 1D (Donor-B), after 7 days of culture in the presence of 10 nM ALT-803, the percentage of $CD4^+$ T cells decreased and the percentage of $CD8^+$ T cells increased in PBMC cultures when compared with that observed in cells incubated in the absence of ALT-803. This finding was more apparent when the CD4/CD8 ratio was analyzed (FIG. 1E: Donor-A and FIG. 1F: Donor-B). There was no significant difference in the percentage of NK cells in PBMC cultures incubated up to 10 days in the presence or absence of ALT-803 (FIGS. 1C & D).

Figure 2A:
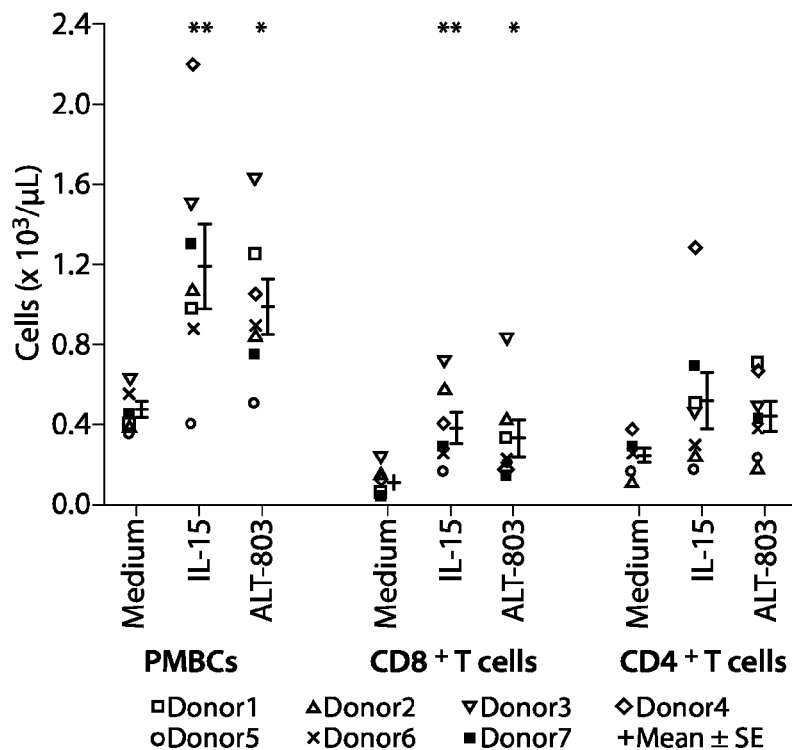
FIG. 2A and FIG. 2B show dot plots demonstrating the effects of ALT-803 on in vitro proliferation of human immune cell subsets from different donors. Human PBMCs were separated from blood buffy coats of 7 healthy donors and cultured in media alone or media containing 0.5 nM IL-15 or ALT-803 for 7 days. At the end of the incubation, PBMCs were counted and stained with fluorochrome-labeled antibodies specific to immune cell subsets. The percentages of the cell subsets were analyzed on a FACSverse with FACSuite software and the absolute cell counts were calculated, as shown in FIG. 2A and FIG. 2B.
Figure 2B:
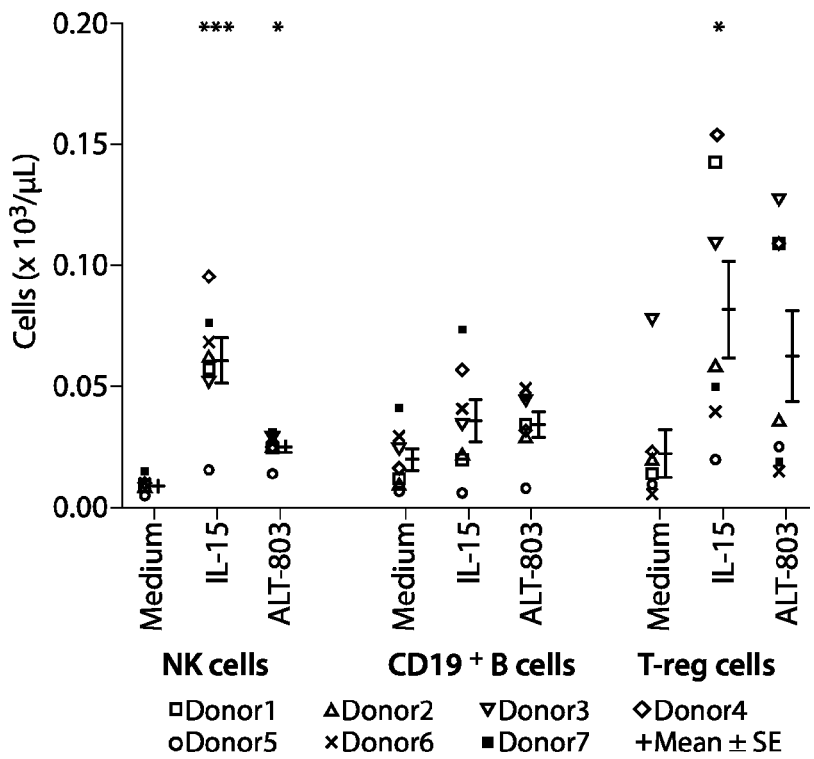
Figure 3A:
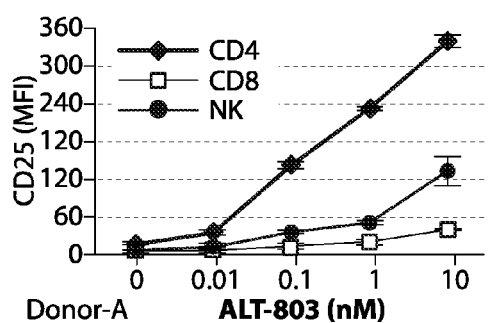
FIG. 3A, FIG. 3B, FIG. 3C, and FIG. 3D are line graphs that demonstrate upregulation of CD25 and CD69 molecules on immune cell subsets following incubation with ALT-803. Human PBMCs were separated from blood buffy coats of two healthy donors (left and right panels) and cultured in RPMI-10 with ALT-803 at the indicated concentration for 5 days. ALT-803 activated PBMCs were stained with fluorochrome-labeled antibodies specific to CD4, CD8 (as markers of T cells), CD335 (as markers of NK cells), CD25 and CD69 (as activation markers). The fluorescent intensity [Geometric mean (MFI)] of CD25 and CD69 expression on $CD4^+$ T cells, $CD8^+$ T cells and NK cells was analyzed on a FACSverse with FACSuite software.
Figure 3B:
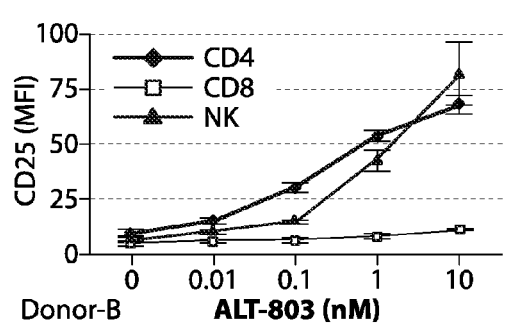
Figure 3C:
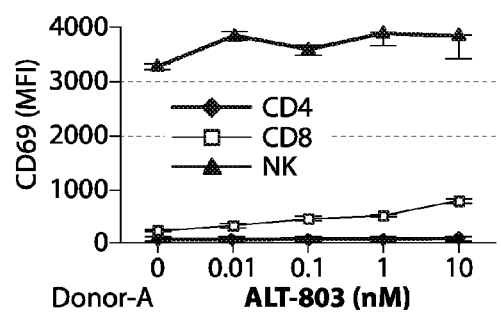
Figure 3D:
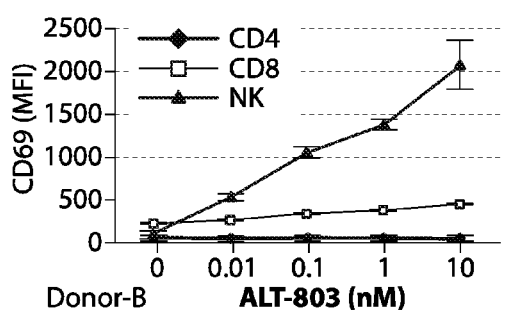
Figure 4A:
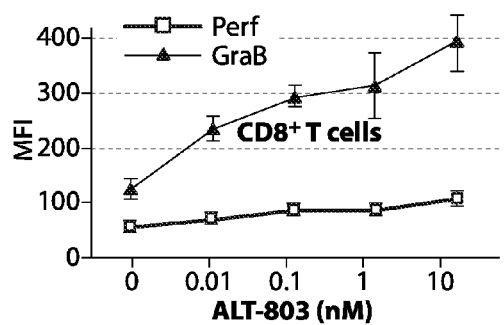
FIG. 4A-FIG. 4D are line graphs that demonstrate upregulation of granzyme B and perforin expression in human $CD8^+$ T cells and NK cells by ALT-803. Human PBMCs were separated from blood buffy coats and cultured in RPMI-10 with ALT-803 at the indicated concentrations for 5 days. ALT-803-activated PBMCs were stained with fluorochrome-labeled antibodies specific to CD8, CD16 and CD335 (as markers of NK cells) and then intracellularly stained with fluorochrome-labeled antibodies specific to granzyme B or perforin. The mean fluorescent intensity (MFI: Geometric mean) of granzyme B and perforin expression on $CD8^+$ T cells (FIG. 4A: donor-1 and FIG. 4C: donor-2) and NK cells (FIG. 4B: donor-1 and FIG. 4D: donor-2) was analyzed on a FACSverse with FACSuite software.
Figure 4B:
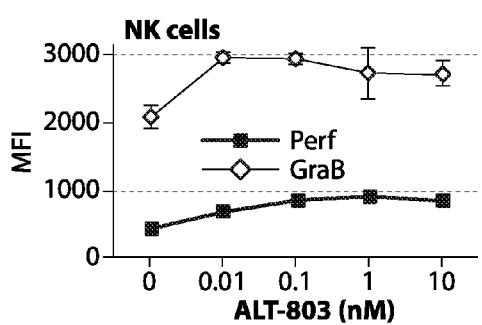
Figure 4C:
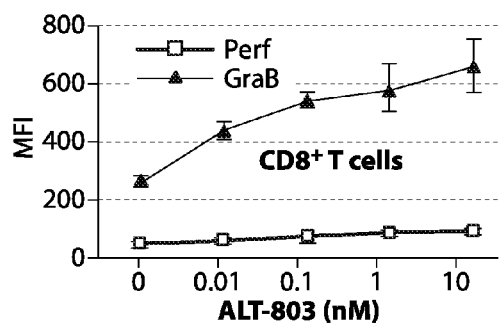
Figure 4D:
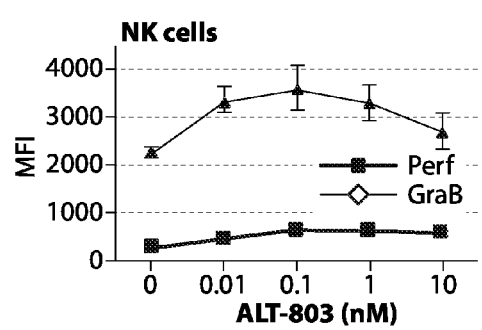

The in vitro effects of ALT-803 were compared to IL-15 on proliferative of human immune cell subsets from different donors. Addition of either 0.5 nM ALT-803 or 0.5 nM IL-15 to human PBMC cultures resulted in ~2-fold increase in lymphocyte counts after a 7-day incubation period. ALT-803 was as potent as IL-15 in increasing the absolute number of $CD8^+$ T-cell and NK cell subsets (FIG. 2A and FIG. 2B). ALT-803 also significantly increased the absolute counts of $CD4^+$ T cells whereas IL-15 increased the absolute counts of Treg cells. In addition, the expression of activation markers, CD25 and CD69, on the immune cell subsets was examined in order to understand immunostimulatory effects of ALT-803. As shown in FIG. 3A-FIG. 3D, in vitro treatment with ALT-803 was capable of increasing CD25 expression by $CD4^+$ T cells, $CD8^+$ T cells and NK cells in a concentration dependent manner. Notably, CD25 upregulation by ALT-803 was most significant on $CD4^+$ T cells compared to that seen on $CD8^+$ T or NK cells. CD25 expression by $CD8^+$ T cells was minimally induced by ALT-803. In contrast to CD25, CD69 expression was highly upregulated on NK cells by ALT-803 incubation, whereas little or no treatment effects were seen on CD69 expression by $CD4^+$ T cells.

The studies were also conducted to assess whether ALT-803 could induce NK cells and $CD8^+$ T cells to express higher levels of granzyme and perforin, which play a key role in cytolytic responses. Human PBMCs were activated in vitro with ALT-803 as described above and followed by Ab staining to differentiate $CD8^+$ T cell and NK cell subsets and then intracellularly stained with FITC-labeled antibodies specific to human granzyme B or perforin. As shown in FIG. 4A-FIG. 4D, ALT-803 was capable of upregulating the expression of granzyme B and perforin by $CD8^+$ T cells (FIG. 4A and FIG. 4C) and NK cells (FIG. 4B and FIG. 4D) in a concentration dependent manner. Moreover, ALT-803-mediated induction of granzyme B expression in both $CD8^+$ T cells and NK cells was more significant than ALT-803-mediated effects on perforin expression. These findings are consistent with the notion that ALT-803-induced expression of granzyme B and/or perforin may play a role to enhanced cytotoxicity of PBMCs following incubation with ALT-803.

Additional studies were conducted to compare the effects of ALT-803 on human and mouse immune cells. Previous studies have shown that the immunostimulatory effects of proteins on human PBMCs could vary significantly depending on whether the protein is present in an aqueous or immobilized form. Thus, cytokine release and proliferation assays were conducted on human and mouse cells using ALT-803 as soluble protein or as plastic-immobilized wet or air-dried protein prepared. ALT-803 was tested at 0.08, 0.8 and 44 nM, which correspond to maximal serum concentrations in human of a 0.3, 3.0 and 170 µg/kg i.v. dose, respectively. For proliferation assays, human PBMCs and mouse $CD3^+$ cells enriched from splenocytes (CD3+ T Cell Enrichment column, R&D System) were labeled with Celltrace™ Violet (Invitrogen) and cultured in wells containing PBS or ALT-803. As a positive control, 27 nM of anti-CD3 Ab (145-2C11 for mouse splenocytes and OKT3 for human PBMCs) was added to separate wells in the same assay formats. The cells were incubated for 4 days and then analyzed by flow cytometry to determine cell proliferation based on violet dye dilution. Additionally, human and mouse immune cells were cultured as described above for 24 and 48 h and cytokines released into the media were measured using Human and Mouse Th1/Th2/Th17 Cytometric Bead Array Cytokine kits according to manufacturer's instructions (BD Biosciences). For immune cell subset analysis, human PBMCs were cultured in various concentrations of ALT-803 or IL-15 and stained with antibodies specific to CD4, CD8, CD335, CD16 or CD19 or with a human Treg kit (BioLegend). In some experiments, cells were also stained with antibodies specific to CD69, granzyme B or perforin as described above.

Figure 5A:
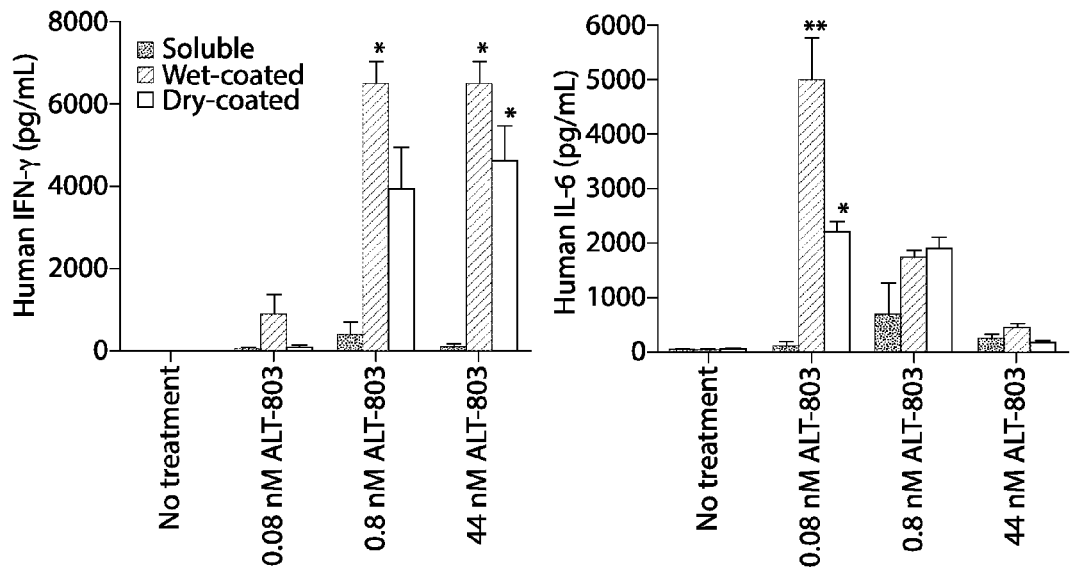
FIG. 5A, FIG. 5B, and FIG. 5C are a series of bar charts demonstrating the effects of ALT-803 on cytokine production and cell proliferation by human and mouse immune cells in culture. Human PBMCs (FIG. 5A) and mouse splenocytes (FIG. 5B) were incubated in media containing ALT-803 as indicated for 4 days. Changes in cytokines secreted in the cell culture media are shown in FIG. 5A and FIG. 5B. Changes in cell proliferative responses based on violet dye dilution are shown in FIG. 5C.
Figure 5B:
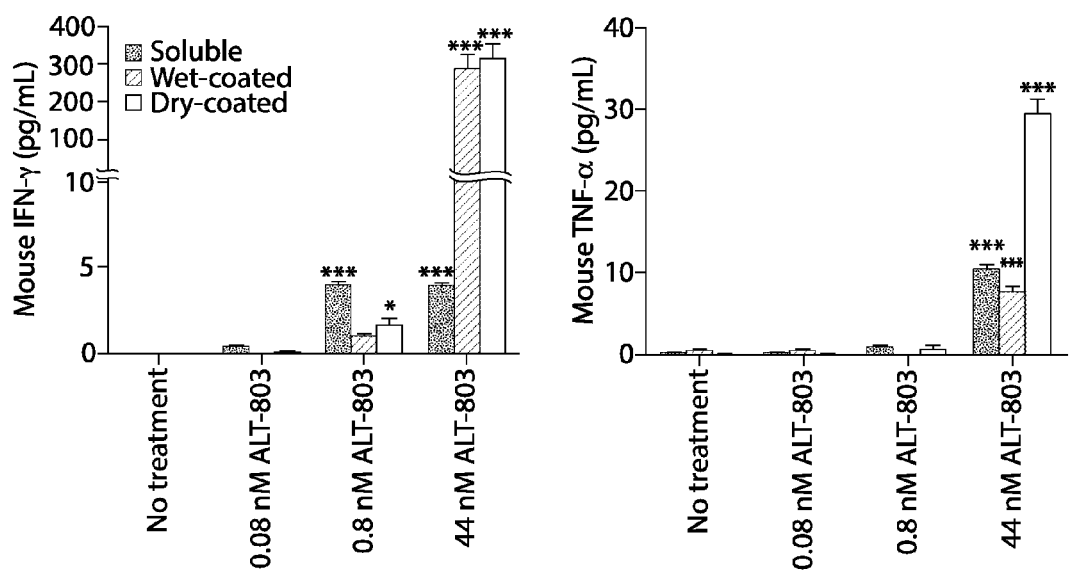

Incubation with immobilized ALT-803 for one day or four days (FIG. 5A) resulted in elevated IFN-γ release by human PBMCs. Soluble IL-6 was also increased in 4-day human PBMC cultures treated with ALT-803, though this effect was not dose dependent (FIG. 5A). In contrast, ALT-803 had no effect on TNF-α, IL-4, IL-10, or IL-17A release by 4-day human PBMC cultures. When tested in parallel cultures, a positive control anti-CD3 mAb induced release of IFN-γ, TNF-α, IL-10, IL-4 and IL-17A. Compared to human immune cells, mouse splenocytes exhibited a similar, but less intense response for IFN-γ release following incubation with ALT-803 (FIG. 5B). ALT-803 also induced TNF-α production from mouse splenocytes, but showed no significant effect on levels of IL-6, IL-2, IL-10, IL-4 and IL-17A. Conversely, murine lymphocytes incubated with immobilized anti-CD3 antibody showed significantly elevated release of all of the cytokines tested. Together, these findings indicate that ALT-803 primarily stimulates IFN-γ production by human and mouse immune cells, in contrast to the broad profile of cytokines induced by anti-CD3 antibodies.

Figure 5C:
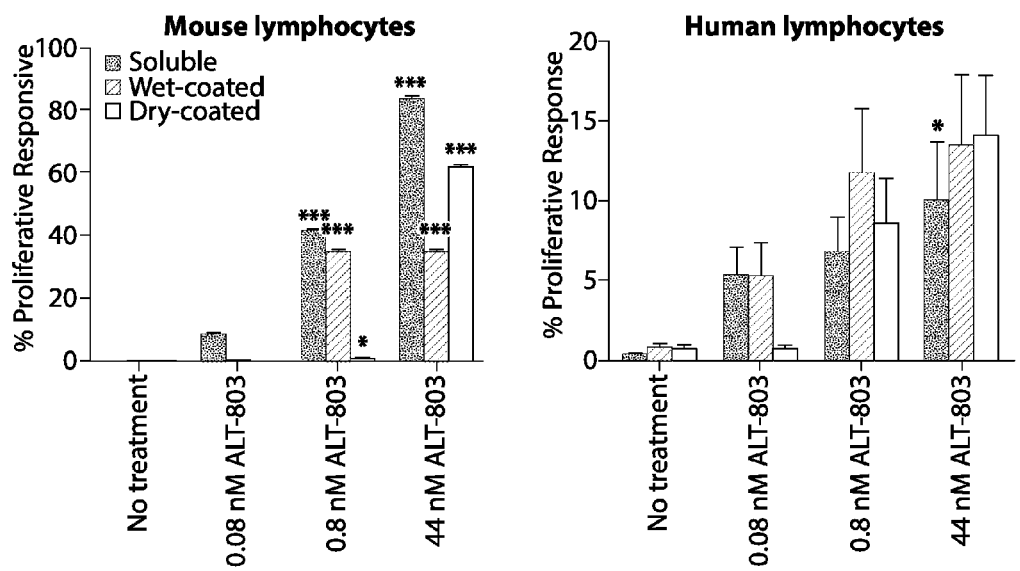

The ability of ALT-803 to induce in vitro proliferation of CellTrace™ Violet labeled human and mouse immune cells was also evaluated. Pronounced proliferation of mouse lymphocytes was evident following incubation with 0.7 nM to 44 nM soluble ALT-803 (FIG. 5C). Up to 83% of the cells in the high-dose soluble ALT-803 group underwent one to six rounds of cell division during the 4-day incubation period. Little or no proliferation was detected in untreated murine cells or those treated with 0.07 nM soluble ALT-803. As expected, murine lymphocytes incubated with immobilized anti-CD3 antibody exhibited strong proliferative responses. ALT-803 dose-dependent lymphocyte proliferation was also observed in human PBMC cultures, but this response was considerably less than that seen for mouse cells. Overall, less than 20% of all human lymphocytes proliferated in response to high-dose ALT-803 and these responses were less than those induced by the positive control anti-CD3 antibody. Additionally, individual variations in cell proliferative responses to both ALT-803 and anti-CD3 Ab were observed in the blood lymphocytes of different donors.

Example 2: Induction of Cell-Mediated Cytotoxicity by ALT-803 and ALT-803 in Combination with Antibodies To assess if ALT-803 affected cell-mediated cytotoxicity, isolated human PBMCs from blood buffy coats were used as effector cells. Daudi human B-cell lymphoma cells and K562 human myelogenous leukemia cells were used as target cells and labeled with Celltrace Violet at 5 µM in RPMI-10 at 37° C. for 20 minutes as described by the manufacturer. The effector cells were mixed with the violet-labeled target cells and incubated at 37° C. with 5% $CO_2$ in RPMI-10 with and without ALT-803 for the indicated times. In some experiments, anti-CD20 Ab (Rituximab, 10 nM) specific to CD20 expressed on the surface of Daudi cells was added to the effector:Daudi cell culture to determine the effects of ALT-803 on anti-CD20 Ab-mediated antibody-dependent cellular cytotoxicity (ADCC). The mixtures of effector cells and target cells were harvested by centrifugation and resuspended in RPMI-10 without phenol red with 2 µg/ml of propidium iodide. Cytotoxicity of the effector cells against the target cells was evaluated by flow cytometry by determining the percentage of dead violet-labeled target cells after propidium iodide positive staining.

As shown in FIG. 6A-FIG. 6D, fresh human PBMCs had weak cytotoxicity against Daudi and K562 cells in the absence of ALT-803. In contrast, PBMCs had very strong cytotoxicity against Daudi and K562 tumor target cells in the presence of ALT-803 at 10 nM. Daudi tumor cells express CD20 molecules, which can be recognized by the anti-CD20 Ab (Rituximab). As indicated herein, CD20 is an established target for therapeutic antibody treatment of hematologic tumors and autoimmune diseases. Human PBMCs are capable of lysing Daudi cells by means of ADCC mediated by Rituximab alone (FIG. 6C, Medium control). Interestingly, ALT-803 was also capable of significantly augmenting Rituximab-mediated ADCC activity of human PBMCs against Daudi cells. As shown in FIG. 6D, a time dependent increase in ALT-803-mediated effects on PBMC cytotoxicity and ADCC was observed, with little or no responses seen after one day of ALT-803 incubation and elevated target cell killing observed with each additional day of incubation.

Figure 7A:
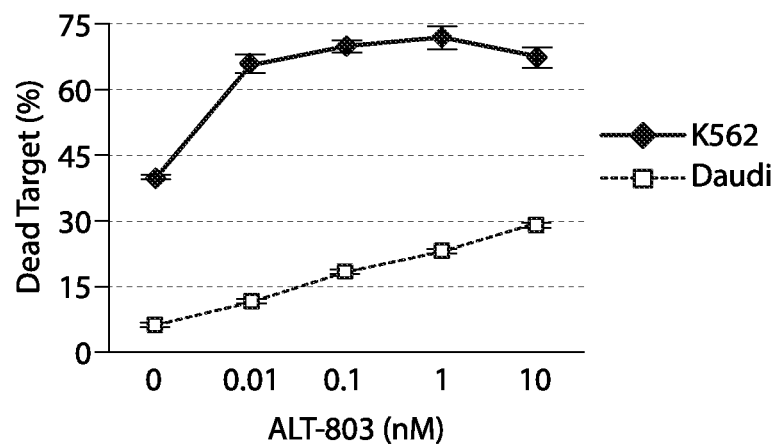
FIG. 7A and FIG. 7B are a series of line graphs demonstrating ALT-803 concentration dependent induction of human PBMC cytotoxicity against K562 and Daudi cells. Human PBMCs were used as effector cells and Celltrace Violet-labeled Daudi and K562 cells were used as target cells. Human PBMCs from two donors (A and B) were mixed with violet-labeled K562 cells or Daudi cells at E:T ratio of 20:1 in RPMI-10 with the indicated concentrations of ALT-803. Following a 3-day incubation at 37° C., the viability of Daudi and K562 target cells was assessed by analysis of propidium iodide staining of violet-labeled target cells on a FACSVerse flow cytometer.
Figure 7B:
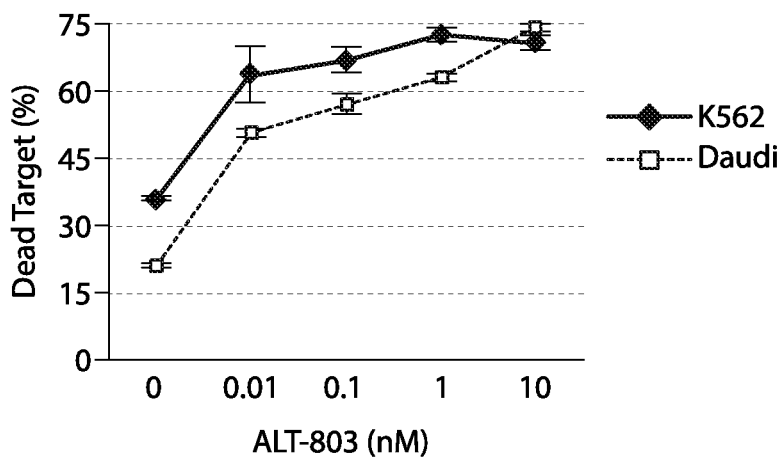

Additionally, ALT-803 concentration dependent induction of human PBMC cytotoxicity against K562 and Daudi cells was investigated. Fresh human PBMCs were mixed with Celltrace Violet labeled K562 cells or Daudi cells in RPMI-10 medium with various concentrations (from 0.01 nM to 10 nM) of ALT-803 followed by incubation for 3 days. The cytotoxicity of the human PBMCs against the target cells was evaluated by flow cytometry as described above. Consistent with the results in FIG. 6A-FIG. 6D, ALT-803 was capable of augmenting cytotoxicity of human PBMCs against Daudi and K562 cells at 10 nM (FIG. 7A and FIG. 7B: Donor-A & Donor-B). Moreover, ALT-803 at as low as 0.01 nM also demonstrated increased cytotoxicity of human PBMCs against the target cells. The PBMCs from two individuals exhibited significantly different cytotoxic activities against the different tumor target cells. PBMCs from Donor-A (FIG. 7A) exhibited much higher baseline and ALT-803-induced cytotoxicity against K562 than Daudi cells. In contrast, PBMCs from Donor-B (FIG. 7B) exhibited similar baseline and ALT-803-induced cytotoxicity against the two different target cells. This finding may be important in understanding the potential variability of ALT-803-mediated clinical responses in different patients. Similar cytotoxicity assays are incorporated as a corollary assessment of patients' immune responses to ALT-803 as part of the clinical use of this molecule.

Figure 8A:
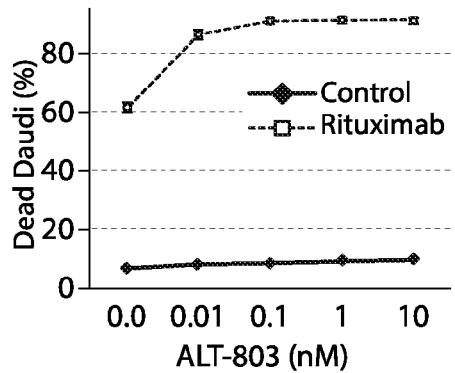
FIG. 8A-FIG. 8D are a series of line graphs showing that ALT-803 augments ADCC of tumor specific Ab against tumor cells. Fresh human PBMCs from donor-1 (FIG. 8A) or donor-2 (FIG. 8B) were mixed with violet-labeled CD20-positive Daudi human B-cell lymphoma cells at E:T=2:1 in RPMI-10 with ALT-803 at the indicated concentration (0.01-10 nM) alone or with Rituximab (anti-CD20 Ab) at 10 nM. After 2 days of incubation at 37° C., the Daudi cell viability was assessed by analysis of propidium iodide staining of violet-labeled Daudi cells on a BD FACSVerse. In a follow-up study, NK cells were isolated from normal human PBMCs by MACS and used as effector cells. NK cells (FIG. 8C) and NK-depleted PBMCs (FIG. 8D) were mixed with violet-labeled Daudi cells at E:T=1:1 in RPMI-10 containing ALT-803 at the indicated concentration (0.01 or 0.1 nM) with and without Rituximab or HOAT Ab at 10 nM. The cells were incubated at 37° C. for 2 days. Daudi cell viability was assessed by analysis of propidium iodide stained violet-labeled Daudi cells on a BD FACSVerse.
Figure 8B:
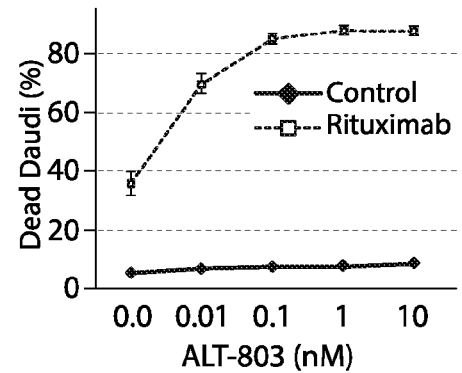
Figure 8C:
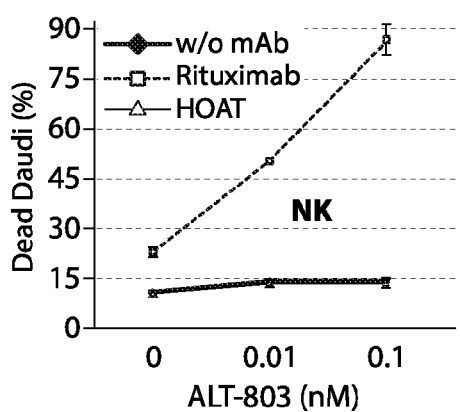
Figure 8D:
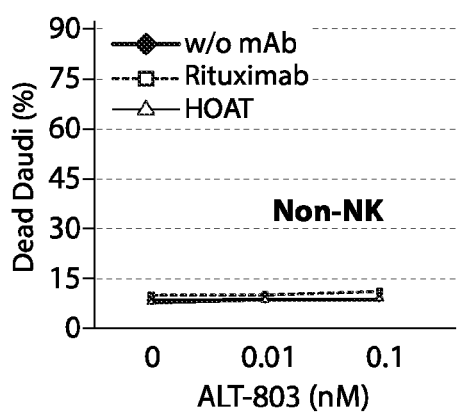

The concentration-dependent effects of ALT-803 on tumor specific ADCC were also further assessed. As shown in FIG. 8A-FIG. 8B, ALT-803 at concentrations at as low as 0.01 nM was capable of augmenting the ADCC activity of anti-CD20 mAb (10 nM) against human Daudi B lymphoma cells. This response was observed with human PMBC effector cells incubated with Daudi cells at a 2:1 E:T ratio, indicating the sensitivity of this activity. In order to identify the immune effector responsible for the observed target tumor cell killing, NK cells were isolated from human PBMCs by MACS and used as the effector cells in the above ADCC assay. Similarly to results with total human PBMC, NK cells were capable of killing Daudi cells via Rituximab-mediated ADCC activity that was enhanced by addition of ALT-803 (FIG. 8C). In contrast, NK cell-depleted PBMCs (non-NK cell) did not display Daudi cell killing detectable ADCC activity in this setting (FIG. 8D). Moreover, addition of a control antibody, HOAT (humanized anti-human tissue factor IgG1 Ab), to NK cells did not provide detectable ADCC activity against Daudi cells with or without addition of ALT-803.

Figure 9A:
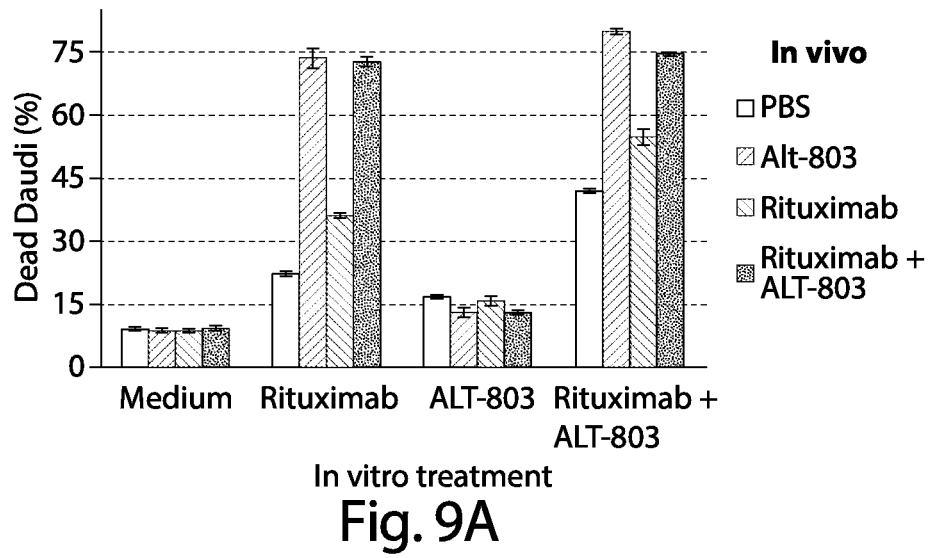
FIG. 9A and FIG. 9B are a bar chart and a line graph showing that ALT-803 augments ADCC of tumor specific Ab against tumor cells by mouse splenocytes. In the study shown in FIG. 9A, splenocytes were isolated from tumor-bearing SCID mice following treatment with PBS, ALT-803 (0.2 mg/kg), Rituximab (10 mg/kg) or ALT-803+Rituximab. The splenocytes and Celltrace Violet-labeled Daudi cells were mixed at E:T=20:1 in the presence of medium alone or medium containing ALT-803 (10 nM), Rituximab (10 nM) or ALT-803+Rituximab. After 2 days of incubation at 37° C. for 2 days, Daudi target cell viability was assessed. Splenocytes were also isolated from Balb/c mice following treatment with ALT-803 (0.2 mg/kg) (FIG. 9B). The splenocytes and Celltrace Violet-labeled HER2-positive SK-BR-3 human breast cancer cells were mixed at E:T=10:1 in the presence of medium alone or medium containing various concentrations of anti-HER2 antibody (clone 24D2), ALT-803 or both agents. After 24 hours of incubation at 37° C., SK-BR-3 target cell viability was assessed.

The ability of ALT-803 to augment ADCC activity of mouse immune cells against human Daudi cells was also examined. In this study, SCID mice were inoculated with Daudi cells ($10 \times 10^6$ per mouse) on study day 0 (SD0) and treated on SD15 and SD18 with ALT-803 (0.2 mg/kg), Rituximab (10 mg/kg), or ALT-803 (0.2 mg/kg)+Rituximab (10 mg/kg). The mice were sacrificed 4 days post the second treatment and splenocytes were prepared. Thus, the splenocytes may have different activation states as a result of the in vivo treatment. The splenocytes were then mixed with Daudi target cells at E:T ratio 20:1 in RPMI-10 medium alone or medium with Rituximab (10 nM), ALT-803 (10 nM) or Rituximab (10 nM)+ALT-803 (10 nM). After 2 days of incubation at 37° C., Daudi target cell viability was assessed by analysis of propidium iodide staining of violet-labeled Daudi cells on a BD FACSVerse. As shown in FIG. 9A, addition of ALT-803 to splenocytes derived from control treated mice was capable of augmenting the anti-CD20 mAb directed ADCC against human Daudi cells. Additionally, in vivo stimulation with ALT-803 resulted in splenocytes that were more active in anti-CD20 mAb directed ADCC against human Daudi cells. These results are consistent with the finding using human immune cells indicating that ALT-803 treatment can potentiate tumor-specific ADCC responses.

Figure 9B:
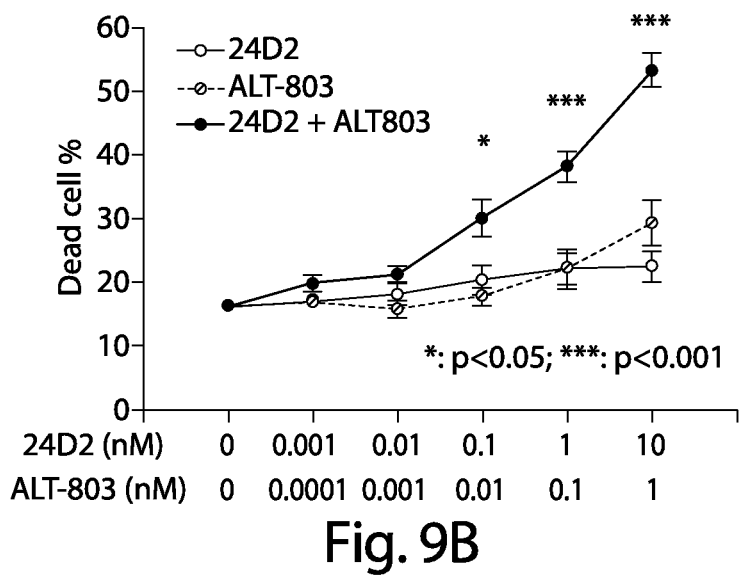

The capacity of ALT-803 to augment ADCC activity of immune cells against other human tumor cells was examined. HER-2 is an established target for therapeutic antibody treatment of solid tumors, including breast cancer and gastric or gastroesophageal junction adenocarcinoma. To assess the effects of ALT-803 on ADCC activity against HER-2-positive tumors, the SK-BR-3 human breast cancer cell line that over-expresses HER-2 was used as a target cell line and an anti-human HER-2 antibody (clone 24D2) was used as a tumor cell-targeted Ab. To generate activated effector cells, Balb/c mice were injected with 0.2 mg/kg ALT-803 intravenously on study day (SD) 0. On SD3, mice were sacrificed and spleens were harvested. Activated splenocytes were mixed with CellTrace Violet-labeled SK-BR-3 cells in 10:1 E:T ratio. Cells were co-cultured at 37° C. in R10 media containing various concentrations of anti-HER2 antibody (clone 24D2), ALT-803 or both agents. After 24 hrs, cell mixtures were collected and dead cells were stained with propidium iodide. The percentage of dead SK-BR-3 cells was examined using flow cytometry. As shown in FIG. 9B, incubation of SK-BR-3 cells with activated splenocytes in the presence of either anti-HER2 Ab or ALT-803 alone did not result in SK-BR-3 cell death compared to media controls. However, combined treatment of ALT-803 (at 0.01-1.0 nM) with anti-HER2 antibody (clone 24D2) (at 0.1 to 10 nM) significantly increased ADCC activity of the splenic immune cells against SK-BR-3 human breast cancer cells. These results verify that ALT-803 can augment ADCC responses to several different therapeutically established disease targets.

Figure 10:
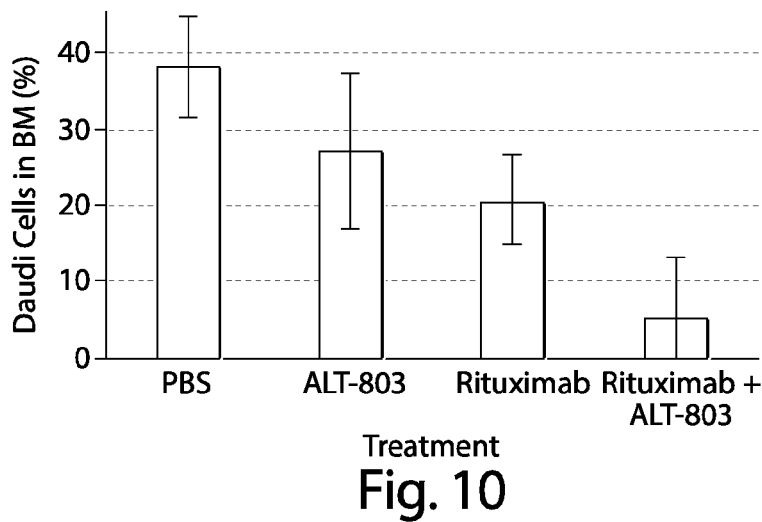
FIG. 10 is a bar chart showing the antitumor efficacy of ALT-803 plus anti-CD20 antibody against human B lymphoma in SCID mice. Fox Chase SCID female mice bearing Daudi cell tumors were treated with PBS, ALT-803 (0.2 mg/kg), Rituximab (10 mg/kg) or ALT-803+Rituximab. Daudi cells in bone marrow were determined 4 days after the last treatment.
Figure 11:
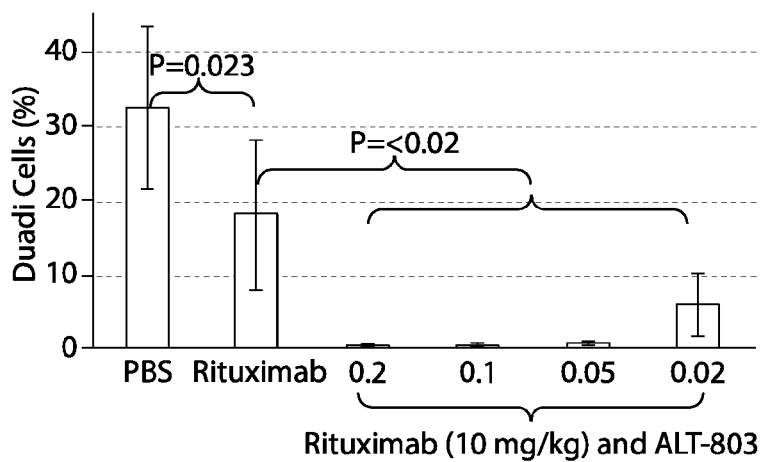
FIG. 11 is a bar graph showing the antitumor efficacy of ALT-803 plus anti-CD20 antibody against human B lymphoma in SCID mice. Fox Chase SCID female mice bearing Daudi cell tumors were treated with PBS, Rituximab or Rituximab plus various concentrations of ALT-803. Daudi cells in bone marrow were determined 4 days after the last treatment.

Example 3: Antitumor Activity of ALT-803+Tumor-Specific Antibody Treatment in Tumor-Bearing Mice The ability of ALT-803 to augment the antitumor activity of anti-CD20 mAb was further evaluated in SCID mice bearing Daudi tumors. These mice have functional NK cells which likely mediate ADCC responses against tumors. For this study, Fox Chase SCID female mice (Harlan, C.B-17/IcrHsd-Prkdc-scid: 6 weeks-old) were inoculated intravenously (i.v.) with Daudi cells ($10 \times 10^6$ per mouse) (3 mice/group). The tumor-bearing mice were treated i.v. with PBS, ALT-803 (0.2 mg/kg), Rituximab (10 mg/kg) or ALT-803 (0.2 mg/kg)+Rituximab (10 mg/kg) 15 days post tumor inoculation and three days later. Four days after second treatment the mice were sacrificed and the levels of the Daudi cells in bone marrow were determined. The percentage of Daudi cells of femur bone marrow cells was assessed following staining with PE-conjugated anti-human HLA-DR antibody (Biolegend) and flow cytometry analysis. The results shown in FIG. 10 indicate that ALT-803 and anti-CD20 mAb monotherapies are capable of reducing the percentage of Daudi cells in the bone marrow of tumor-bearing mice. However the combination of ALT-803 plus anti-CD20 mAb provided the greatest antitumor activity reducing bone marrow Daudi cells from 38% in control mice to 5% in ALT-803+Rituximab treated mice. Dose responses studies in this model confirmed that as little as 0.02 mg/kg ALT-803 was capable of augmenting the antitumor activity of anti-CD20 mAb (FIG. 11).

Figure 12:
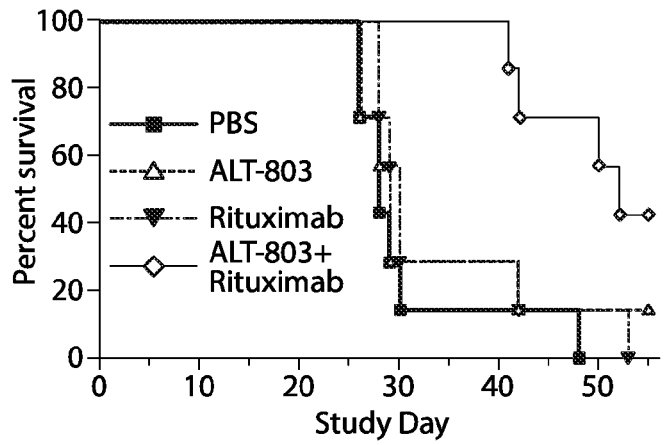
FIG. 12 is a line graph demonstrating prolonged survival of mice bearing Daudi cell tumors following ALT-803 plus anti-CD20 Ab therapy. Fox Chase SCID female mice bearing Daudi cell tumors were treated with PBS, Rituximab (10 mg/kg), ALT-803 (0.05 mg/kg) or Rituximab plus ALT-803. The survival of the mice was monitored and Kaplan-Meier survival curves were plotted.

The ability of ALT-803 plus anti-CD20 mAb to improve survival of mice bearing Daudi cell tumors was also evaluated. For this study, Fox Chase SCID female mice were inoculated intravenously (i.v.) with Daudi cells ($10 \times 10^6$ per mouse). The tumor-bearing mice were treated i.v. with PBS, ALT-803 (suboptimal 0.05 mg/kg), Rituximab (10 mg/kg) or ALT-803 (0.05 mg/kg)+Rituximab (10 mg/kg) 15 days post tumor inoculation and three days later. Survival (including morbidity based on hind leg paralysis) of the mice was monitored. As shown in FIG. 12, tumor bearing mice of the PBS, suboptimal ALT-803 and Rituximab monotherapy groups showed median survival of 26-30 days whereas the mice treated with suboptimal ALT-803 plus Rituximab had a mean survival of greater than 50 days, indicating combined therapy significantly prolongs survival of mice bearing B cell lymphomas. Together, these results confirm the synergistic antitumor effects of ALT-803 in combination with tumor-specific antibodies in vivo. It is also noteworthy that the combination of ALT-803 plus anti-CD20 mAb did not cause any significant signs of toxicity in the tumor-bearing animals for studies described above, which indicates that these combinations are well tolerated.

Example 4: Antitumor Activity of ALT-803 in Combination with Immune Checkpoint Blockers in Tumor-Bearing Mice Immune checkpoint blockers including antibodies against CTLA-4, PD-1, PD-L1, PD-L2, B7-H3, B7-H4, LAG-3, BTLA, TIM-3, VISTA, IDO, A2aR, HVEM, KIRs, NKG2A, NKG2D, CEACAM-1, 2B4, CD200R, and their ligands and other targets described herein may be capable of promoting immune responses by inhibiting immune suppressive signals. As indicated above, ALT-803 is an immunostimulatory molecule that promotes proliferation and activity of NK cells and T cells. However, its effectiveness may be limited by inhibitory checkpoints and pathways that can attenuate immune responses. Strategies that abrogate these negative regulators and enhance the activity of ALT-803 could provide therapeutic benefit.

To examine the antitumor activity of ALT-803 in combination with blockade of the CTLA-4-CD80/CD86 pathway, a lung metastasis model was developed using BALB/c mice injected i.v. with the CT26 murine colon carcinoma cell line. Groups of 4-6 mice were injected i.v. with $2\times10^5$ CT26 tumor cells on day 0 (SD0). In the ALT-803 groups, each mouse received 4 µg of i.v. ALT-803 twice a week for two weeks starting on SD1. Along with ALT-803, some mice received of either anti-PD-L1 antibody (Ab) (clone 9G2), anti-CTLA-4 (clone UC10-4F10-11) Ab or both at 100 µg per injection (per Ab) administered i.v. twice a week for 2 weeks starting on SD1. In the recombinant human IL-15 groups, each mouse received 5 µg of IL-15 intraperitoneally (i.p.) daily, 5 times a week for 2 weeks starting on SD1. Along with IL-15, animals also received i.v. treatment of both anti-PD-L1 Ab and anti-CTLA-4 Ab (100 µg per injection) on SD1, SD4, SD8 and SD11. Control mice received injections of PBS. Mice were assessed daily for survival as an efficacy endpoint.

Figure 13A:
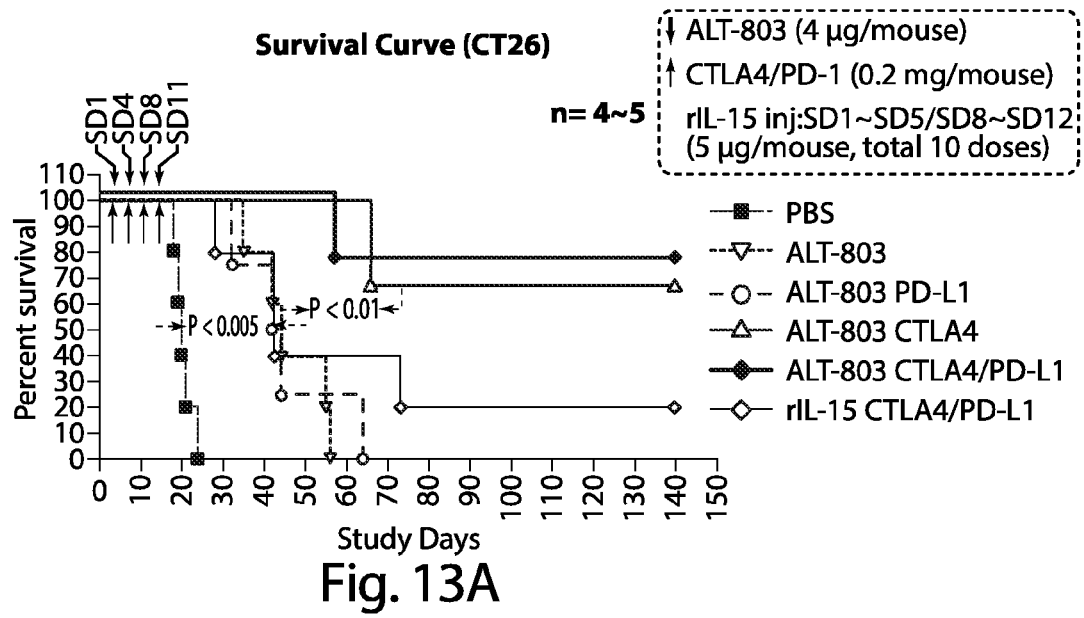
FIG. 13A and FIG. 13B are a series of line graphs showing the prolonged survival of mice bearing CT26 colon carcinoma lung metastases following ALT-803 and ALT-803 plus anti-CTLA-4 Ab therapy. BALB/c mice bearing CT26 colon carcinoma lung metastases were treated with PBS, ALT-803, IL-15 monotherapies and combination therapies with anti-CTLA4 Ab and anti-PD-L1 Ab as indicated in the figures. The survival of the mice was monitored and Kaplan-Meier survival curves were plotted.
Figure 13B:
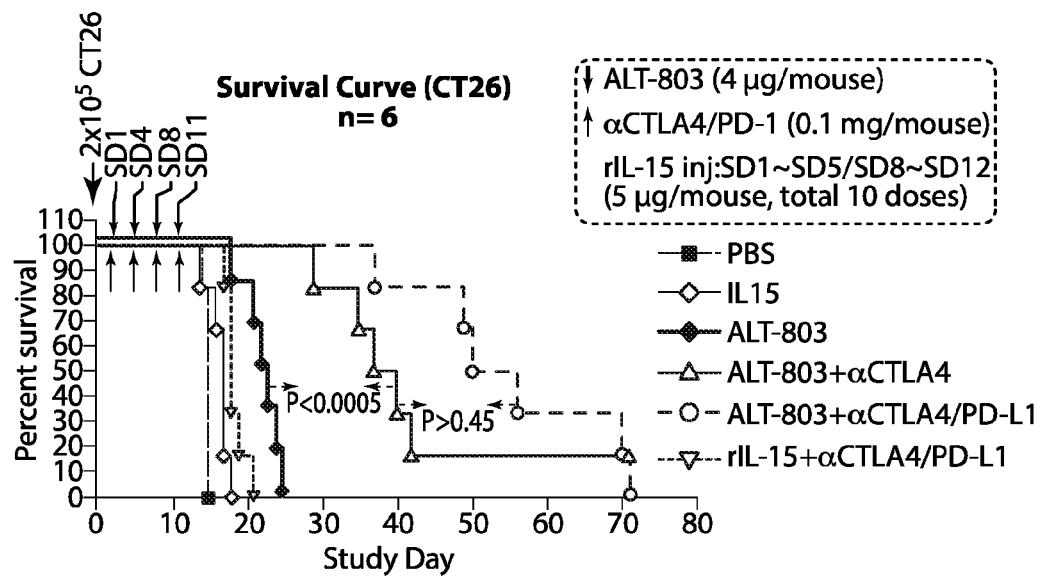

As shown in FIG. 13, the median survival of BALB/c mice bearing CT26 tumors was 15 to 20 days depending on the study. Treatment with ALT-803 alone significantly prolonged survival of tumor bearing mice when compared to the control group. Addition of anti-PD-L1 Ab treatment to ALT-803 did not appear to improve survival in these mice. In contrast, the combination of ALT-803 and anti-CTLA4 Ab (with or without anti-PD-L1 Ab) significantly increased the survival of CT26 tumor bearing mice compared to the PBS and ALT-803 groups. Previous studies in this tumor model showed that anti-CTLA4 Ab monotherapy did not improved survival. Thus, the combination of ALT-803 and anti-CTLA4 Ab (but not anti-PD-L1 Ab) acts synergistically in providing more efficacious antitumor responses as measured by prolonged survival on tumor-bearing mice.

The effects of PD-1-PD-L1 blockade in combination with ALT803 were further evaluated in the 5T33P myeloma model in immunocompetent C57BL/6 mice. Groups of 5 mice were injected i.v. with $1\times10^7$ 5 T33P tumor cells on SD0. Treatment began on SD4. In the IL-15 group, each mouse received 5 µg of IL-15 i.v. on SD4 and SD11. Along with IL-15, some animals also received anti-PD-L1 Ab (clone 9G2, 200 µg/mouse/injection i.p.) or anti-CTLA-4 Ab (clone UC10-4F10-11, 200 µg/mouse/injection i.p.) once a week on SD4 and SD11 respectively. In ALT-803 group, each mouse received two i.v. injections of suboptimal ALT-803 at 1 µg/mouse/injection on SD4 and SD11. Along with ALT-803, some mice received either anti-PD-L1 Ab, anti-CTLA-4 Ab or both antibodies as indicated above. Additionally, groups of mice received anti-PD-L1 Ab or anti-CTLA-4 Ab monotherapy and received injections of PBS. Mice were assessed daily for survival and/or full paralysis in both hind legs as the study endpoint. As shown in FIG. 14A, the median survival of C57BL/6 mice bearing 5T33P tumors was 24 days. Treatment with a suboptimal dose of ALT-803 did not significantly change animal survival, but administration of suboptimal ALT-803 plus anti-PD-L1 Ab resulted in survival of all animals in this study group for at least 50 days. In contrast, the combination of ALT-803 and anti-CTLA4 Ab did not significantly prolong mouse survival. Additionally, when suboptimal levels of both ALT-803 and anti-PD-L1 Ab were tested as monotherapies and in combination, significantly longer survival was observed in C57BL/6 mice bearing 5T33P tumors following treatment of ALT-803+anti-PD-L1 Ab compared to mice treated with either monotherapy (FIG. 14B). Thus, the combination of ALT-803 plus anti-PD-L1 Ab provides synergistic antitumor activity in mice bearing myeloma tumors.

To better understand the divergent activities of the ALT-803 combination therapies in these two models, the tumor cell lines were stained for ligands of the PD1 and CTLA4 receptors. As shown in FIG. 15, CT26 cells express ligands for CTLA4 but not PD1. In contrast, 5T33P tumor cells express PD-L1 but not ligands for CTLA4. These results are consistent with the antitumor activities of anti-CTLA4 and anti-PD-L1 Abs in combination ALT-803 in each of these tumor models, indicating that staining tumors with ligands for immune check point receptors may provide a predictive indicator for response to ALT-803 plus immune check point blockers.

Using an established model for glioblastoma described in Zeng et al. 2013 Int J Radiat Oncol Biol Phys., 86:343-9, studies of ALT-803 monotherapy and ALT-803 in combination with anti-PD-1 mAb were also carried out in C57BL/6 mice that had been intracranially implanted with the glioblastoma cell line, GL261-luc. Treatment with multiple doses of ALT-803 (3 or 4 doses) or anti-PD-1 mAb (3 doses) as monotherapy starting 7 to 10 day post-tumor implantation exhibited similar increases in antitumor activity and prolonged animal survival when compared to PBS-treated controls. The combination of ALT-803 and anti-PD1 mAb treatment further extended median survival times of tumor-bearing mice. Additionally, anti-PD-1 mAb in combination with 4 doses of ALT-803 increased the percentage of long-term tumor free survivors (>60 days post-implantation) to 40% from the 20% rate observed in mice treated with anti-PD-1 Ab and ALT-803 monotherapy. Interestingly, the "cured" mice were resistant to tumor rechallenge, suggesting treatment-induced immune memory response against the tumor. These results suggest that combining the immunostimulatory activity of ALT-803 with the checkpoint blocker, anti-PD-1 Ab, has a beneficial effect in prolonging survival of glioblastoma tumor bearing mice.

It is also noteworthy that the combination of ALT-803 plus checkpoint inhibitor blockade did not cause any significant signs of toxicity in the tumor-bearing animals for studies described above, which indicates that these combinations are well tolerated.

Example 5: Toxicity of ALT-803 in Mice

To evaluate the safety profile and therapeutic index of ALT-803 in animals and estimate the safe and efficacy human dose, toxicity studies of multidose ALT-803 treatment were conducted in mice and cynomolgus monkeys.

C57BL/6N mice (10 mice/sex/group) were administered 0.1, 1.0 or 4.0 mg/kg ALT-803 or PBS via the tail vein weekly for 4 consecutive weeks. Four days after the last injection (day 26), assessments including physical examination, blood chemistry, hematology, gross necropsy, body and organ weight measurements and histopathology were performed (5 mice/sex/group). Similar assessments were performed on the remaining mice fourteen days after the last treatment (day 36). In a second study, C57BL/6N mice (15 mice/sex/group) were treated with 4 weekly i.v. injections of 0.1 or 1.0 mg/kg ALT-803 or PBS. Toxicity assessments as described above were performed four days (day 26) (10 mice/sex/group) or 4 weeks after the last injection (day 50) (5 mice/sex/group).

The safety and pharmacodynamic profiles of ALT-803 was assessed in healthy C57BL/6N mice injected i.v. with 0.1, 1.0 or 4.0 mg/kg ALT-803 or PBS weekly for four consecutive weeks. Mice receiving 4.0 mg/kg ALT-803 exhibited signs of toxicity (i.e., weight loss, hair loss) and mortality between 4 to 20 days after treatment initiation. Post-mortem necropsy did not determine the cause of death but observations (i.e., pulmonary edema, enlarged spleens) were consistent with cytokine-induced lethal inflammatory responses. Mortality was not observed in mice treated with 1.0 or 0.1 mg/kg ALT-803. Dose dependent increases in spleen weights and white blood cell (WBC) counts were seen 4 days after the last dose of ALT-803 (Day 26) (FIG. 16). Of the WBCs, absolute counts for lymphocytes, neutrophils and monocytes each increased over 8 fold in 1.0 mg/kg ALT-803-treated mice compared to controls. Two weeks (Day 36) and four weeks (Day 50) after treatment (FIG. 16A-FIG. 16F), neutrophil counts remained elevated in 1.0 mg/kg ALT-803-treated mice, but lymphocyte counts returned to control levels. Histopathological analysis verified ALT-803 dose-dependent stimulation of immune cell proliferation and lymphocyte infiltration in the spleen, liver, *thymus*, kidney, lungs and lymph nodes on day 26 and to a lesser degree on day 36 and day 50. The results of these studies defined the tolerable dose of multidose ALT-803 treatment at up to 1 mg/kg in mice.

Example 6: Toxicity, Pharmacodynamics (PD), and Pharmacokinetics (PK) of ALT-803 in Cynomolgus Monkeys A study was performed under Good Laboratory Practice regulations to evaluate the effects of multidose i.v. administration of ALT-803 in cynomolgus monkeys. Animals (5 monkeys/sex/group) were treated weekly for 4 consecutive weeks (days 1, 8, 15 and 22) with 0.03 or 0.1 mg/kg ALT-803 or PBS administered as a ~3 min i.v. injection. Throughout the in-life phase of the study, animals were assessed for clinical and behavioral observations, food consumption, body weight, cardiac and ocular function. Blood was taken for hematology, chemistry and coagulation assessments (pre-dosing and days 5, 26 and 36 post-dosing) and for immune cell analysis. Serum was taken for immunogenicity testing and PK analyses conducted using qualified enzyme-linked immunosorbent assay (ELISA) methods. Urine was collected for urinalysis (pre-dosing and days 4, 25 and 35). Clinical pathology assessments including physical examination, gross necropsy, organ weight measurements and histopathology were performed four days (day 26) (3 animals/sex/group) and 2 weeks after the last injection (day 36) (2 animals/sex/group).

Based on allometric scaling to the tolerable murine dose, the activity and toxicity profiles of multidose i.v. treatment of ALT-803 at 0.1 and 0.03 mg/kg were assessed in healthy cynomolgus monkeys. PK analysis after the first dose estimated the 1 elimination half-life of ALT-803 at approximately 7.6 hrs, which did not appear to differ significantly between dose levels (FIG. 17). The $C_{max}$ value of 30 nM for 0.1 mg/kg ALT-803 is consistent with full recovery of the administered dose, whereas Cmax and $AUC_{INF}$ values indicate ~30% less recovery at the 0.03 mg/kg dose. However, even at the low dose level, the $C_{max}$ of 6 nM in the serum was over 50 higher than the 0.1 nM concentration found to stimulate immune cell proliferation, activation and cytotoxicity in vitro.

Monkeys receiving 4 consecutive weekly injections of ALT-803 showed a dose-dependent reduction in appetite during the first 2 weeks of the treatment period. However, there were no significant differences in mean body weights or any other dose-related clinical or behavior observations among the groups during the study. Additionally, organ weights were not significantly different in ALT-803 treated animals compared to controls.

The most biologically relevant changes observed following weekly ALT-803 treatment were dose-dependent increases in blood WBC and lymphocyte counts (FIG. 18A-FIG. 18H). At the end of the four week dosing period, absolute lymphocyte counts increased 1.5-fold in animals receiving 0.1 mg/kg ALT-803 and then returned to control levels after a 2-week recovery period. Of the lymphocyte subsets, transient dose-dependent increases in NK cell and $CD4^+$ and $CD8^+$ T cell counts were seen post treatment (FIG. 18A-FIG. 18F). Blood monocyte counts also increased in 0.1 mg/kg ALT-803 treated monkeys whereas blood neutrophil levels were not different among the treatment groups. These results contrast with previous studies of IL-15 administration to macaques and rhesus monkeys where the major toxicity reported was grade 3/4 transient neutropenia.

In addition to changes in blood immune cell levels, there was dose-dependent increase in mild multifocal lymphocytic infiltration in the livers, kidneys and lungs of ALT-803 treated monkeys based on histopathology conducted 4 days after the last dose of ALT-803. Scattered mild liver necrosis was also seen with increased frequency in ALT-803 treated animals. Clinical chemistry at this time point showed a decrease in serum albumin in the high-dose ALT-803 group compared to controls (0.1 mg/kg ALT-801, 3.85±0.12 g/dL; PBS, 4.46±0.13 g/dL; P<0.01), which may be a consequence of inflammatory responses in the liver. However, serum liver enzyme levels were not elevated in ALT-803 treated animals compared to controls. Bone marrow hyperplasia was observed in most animals but with increased severity in the high-dose ALT-803 group. Lesions in a majority of affected organs in the ALT-803 treated groups were reduced in incidence and severity by two weeks post-treatment and were consistent with findings in the control animals. Generally, the ALT-803-mediated effects on blood and tissue lymphocytes observed in this study are consistent with transient responses reported for non-human primates treated with IL-15 twice weekly at up to 0.1 mg/kg or daily at 10 to 50 µg/kg.

Example 7: Comparative Studies of Intravenous and Subcutaneous ALT-803

Emerging data from ongoing trials using recombinant human IL-15 (rhIL-15) product suggests that intrevenous dosing is likely not optimal for IL-15 because it induces a high Cmax and secondary cytokine release (IL-6 and IFN-γ)

that affects its tolerability and is therefore limiting. Preclinical and clinical studies with IL-2 indicate that subcutaneous dosing is safer and provides much better tolerability. For example, Waldmann and colleagues conducted the first solid tumor trial of rhIL-15 in human using daily intravenous bolus infusion for 12 consecutive days (Conlon et al., 2015. J. Clin. Oncol., 33: 74-82). Dose limiting toxicities observed in the 3.0 and 1.0 µg/kg per day cohort were grade 3 hypotension, thrombocytopenia, and elevations of alanine transaminase (ALT) and aspartate transaminase (AST). The maximum tolerated dose (MTD) was declared at 0.3 µg/kg per day. An increased tolerance of subcutaneous dosing is anticipated as a result of a decreased Cmax compared with the same dose level administered intravenously and more sustained levels of the rIL-15 product in circulation. Lowering the Cmax allows for more drug delivery overall.

To extend these findings to ALT-803, preclinical studies were conducted to evaluate i.v. (intravenous) and s.c. (subcutaneous) administration of ALT-803 in terms of the pharmacokinetics, immunostimulation and antitumor efficacy in C57BL/6 mice. Initial studies of C57BL/6 mice treated with 0.2 mg/kg ALT-801 showed an estimated half-life of 5.3 hours for i.v. administration and 3.8 hours for s.c. administration. The maximal serum concentration of ALT-803 was 650 ng/ml at 20 hour time point following s.c. administration and 1700 ng/ml at 2 hour time point following i.v. administration. In terms of immune stimulation, ALT-803 administered s.c. or i.v. could equally induce proliferation of CD8+ T cells and NK cells. Additionally, i.v. and s.c. administration of ALT-803 similarly activated immune cells to reduce tumor burden in the bone marrow of 5T33 myeloma-bearing mice. Both i.v. and s.c. administration of ALT-803 at up to 0.2 mg/kg was well tolerated in normal and tumor-bearing C57BL/6 mice.

A follow-up study for toxicological effects of 1 mg/kg ALT-803 injected s.c. weekly for 4 weeks in C57BL/6 mice revealed immune system-related changes that were similar to those seen in a previous toxicology study in which the C57BL/6 mice were treated with the same ALT-803 dosing regimen using an i.v. route. No mortalities were observed in mice following 4 weekly s.c. injections of 1 mg/kg ALT-803. With the exception of slight weight loss and the observance of hunched posture after the first s.c. injection of ALT-803, no clinical signs of test article related toxicities were observed during this study. Examination of the peripheral blood revealed that there were increased numbers of WBC and lymphocyte counts compared to PBS controls. Overall, there was a 9-fold increase for both WBCs and lymphocytes in animals treated with ALT-803 compared to PBS injected mice. An increase in neutrophils, monocytes, eosinophils and basophils was also observed in s.c. ALT-803 treated mice. Significant increases in the weight of spleen, lymph node, and liver (5.5, 3, and 1.3-fold respectively) of ALT-803 treated mice were observed. Comparable broad-based expansion of immune cells and increased weights of lymphoid organs was previously reported for mice receiving multidose i.v. treatment with ALT-803.

Overall, the results of the preclinical studies of ALT-803 indicated that s.c. dosing decreases the Cmax compared to i.v. dosing, but retains the immunostimulatory activity and antitumor efficacy without exaggerating toxicity.

Example 8: Antitumor Activity of ALT-803 in Combination with Immune Checkpoint Blockers in Mice Bearing Orthotopic Bladder Tumors In addition to the studies described in Example 4, the antitumor activity of ALT-803 in combination with immune checkpoint blockers was evaluated in mice bearing orthotopic MB49luc bladder tumors. C57BL/6 mice (n=6/group) were instilled intravesically with MB49luc cells ($3 \times 10^4$ cells/bladder) on study day 0, following polylysine pretreatment of the bladders. PBS, ALT-803 (0.2 mg/kg, i.v.) or ALT-803 (0.2 mg/kg) plus anti-PD-L1 and anti-CTLA4 Abs (each at 100 µg/injection, i.p.) was administered on 7, 10, 14, and 17 days post MB49luc tumor cell instillation. The mice were maintained to assess survival rate among the treatment groups as the efficacy endpoint. ALT-803 treatment significantly prolonged the survival of the MB49luc bearing mice compared with PBS (FIG. 19A). However, the combination of ALT-803 with anti-PD-L1 and anti-CTLA4 Abs further prolonged survival compared to control of monotherapy. This effect was also seen with combination therapy of ALT-803+anti-PD1 and ALT-803+anti-PD1/anti-CTLA4 mAbs (FIG. 19B).

Additionally, mice that were cured of tumors by ALT-803 plus anti-PD-L1/anti-CTLA4 Ab therapy were resistant from bladder tumor rechallenge without further drug treatment whereas age—matched treatment-naïve mice developed tumors and die following tumor cell instillation (FIG. 19A). These results indicate that ALT-803 monotherapy and combination therapy with anti-PD-L1, anti-PD-1 and anti-CTLA4 Abs was effective at treating bladder tumor bearing mice, including curative responses, and that the ALT-803/anti-PD-L1/anti-CTLA4 Ab combination therapy provided immune memory responses to subsequent tumor challenge. It is also noteworthy that the combination of ALT-803 plus checkpoint inhibitor blockade did not cause any significant signs of toxicity in the tumor-bearing animals for studies described above, which indicates that these combinations are well tolerated. As shown in FIG. 20, MB49luc cells express ligands for CTLA4 and PD-1. As such, these results are consistent with the antitumor activities of anti-CTLA4, anti-PD-1, and anti-PD-L1 Abs in combination ALT-803 in this tumor model.

Example 9: Combined Therapy of ALT-803 and Anti-Gp75 Antibody, TA99, in Murine Melanoma Model The subcutaneous B16F10 melanoma tumor model in syngeneic C57BL/6 mice was used to further evaluate the efficacy of ALT-803 plus a therapeutic tumor antigen specific antibody against solid tumors. This model also has the advantage of assessing the activity of T cells and other immune cells against established tumors and tumor rechallenge. One important melanoma-specific antigen for targeted therapy is gp75 (TYRP-1, tyrosinase-related protein-1), a 75 kDa protein involved in melanin synthesis in melanosomes (Kobayashi T, et al. 1994. EMBO J. 13:5818-25). TA99 (mouse IgG2a) is a monoclonal antibody (mAb) specific for human and murine gp75 (Thomson T M, et al. 1985. J Invest Dermatol. 85:169-74). Treatment with this antibody effectively abrogates subcutaneous murine B16F10 melanoma in syngeneic mice through the activation of antibody-dependent cellular toxicity (ADCC) (Hara I, et al. 1995. J Exp Med. 182:1609-14).

The experiments described herein were designed to determine whether this activity could be further augmented by combination with ALT-803 and assess immune responses responsible for anti-tumor efficacy. In general, C57BL/6NHsd mice (7-week-old females) were injected s.c. on the lower dorsal flank with $2 \times 10^5$ B16F10 tumor cells in 200 µL PBS on study day 0 (SD0). For all experiments in this study except tumor rechallenge, treatments were administered twice a week for two weeks (on study day 10, 14, 17, 21 and 24) starting from SD10, the time point when more than 75% of the animals had palpable B16F10 tumors. More specifically, mice were split into groups and injected with 200 μL PBS (i.v.) (vehicle control), 0.2 mg/kg ALT-803 (i.v.), 10 mg/kg TA99 (i.v.), 100 μg/mouse anti-PD-L1 mAb 10F.9G2 (i.p.), or combination therapy of ALT-803, TA99 and/or 10F.9G2. For depletion experiments, 200 μg/mouse depletion antibodies (anti-CD4 GK1.5, anti-CD8a 53.6.72 and anti-NK1.1 PK136) were injected i.p. once every week or 100 μL/mouse Clophosome (clodronate-loaded liposomes for macrophage depletion) were injected i.p. once every 4 days, starting from SD3 and SD9 respectively, until the endpoint of the experiment. For experiments involving tumor rechallenge, 10 mg/kg TA99 (i.v.) was administered three times a week, 0.2 mg/kg ALT-803 (i.v.) was administered once a week, for three weeks starting from SD0. After about three months, tumor-free mice rescued from the initial tumor challenge were injected s.c. contralaterally with 2×10$^5$ B16F10 tumor cells in 200 μL PBS. Tumor volumes were measured daily starting from the first day of treatment to the end, and calculated using formula ½(Length×Width$^2$). Mice bearing a tumor load with one dimension >20 mm were sacrificed and counted as dead. Mice with no palpable tumor or a stable s.c. mass <50 mm$^3$ were counted as tumor-free.

In the initial study, mice (n=8) bearing established tumor were treated with TA99, ALT-803, TA99+ALT-803, or PBS control twice a week for two weeks (FIG. 21A). Due to delayed therapeutic intervention, no tumor regression was observed in any of the treatment groups. However, tumor progression was significantly inhibited by TA99 (p<0.001) and ALT-803 (p<0.001) compared to PBS-treated group. Combined therapy resulted in a significantly enhanced inhibition of tumor growth compared to either monotherapy (p<0.001), suggesting ALT-803 offers additional protection to the antibody-dependent immunity against tumor. To determine which immune cell subsets are responsible for the ALT-803/TA99-mediated anti-melanoma immunity, T lymphocyte, NK cells and macrophages were depleted before and throughout the treatment course by intraperitoneal administration of cell type-specific antibodies or liposomes. Depletion of CD8$^+$ T cells, NK cells and macrophages significantly lowered inhibition of tumor growth by the combined therapy (p<0.001; FIG. 21B), suggesting all three cell subsets contribute to the efficacy of ALT-803 and TA99. Surprisingly, depletion of CD4$^+$ T cells not only caused significant enhancement of tumor inhibition (p<0.001; FIG. 21B), but also significant increase of animal survival (p<0.01; FIG. 21C) compared to ALT-803+TA99 treatment group without depletion. Considering CD4$^+$ T cells are heavily involved in immune regulatory functions, this finding suggest these cells (or a subset of CD4$^+$ T cells) are immunosuppressive rather than immunoreactive in the initial ALT-803/TA99-mediated immunity against B16F10 tumors.

Figure 22A:
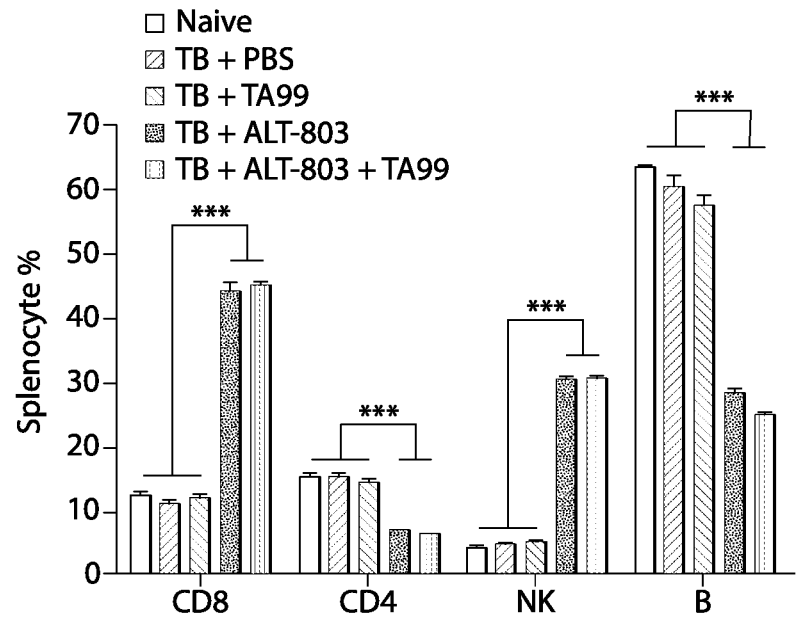
Figure 22B:
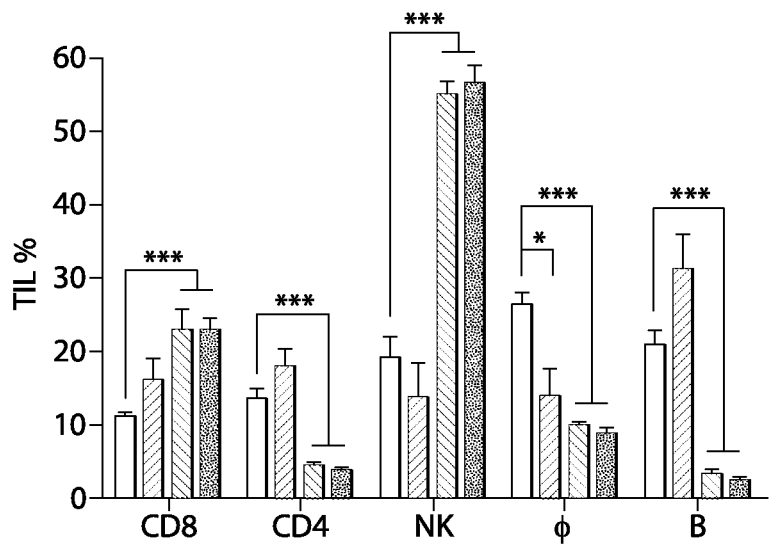
Figure 22C:
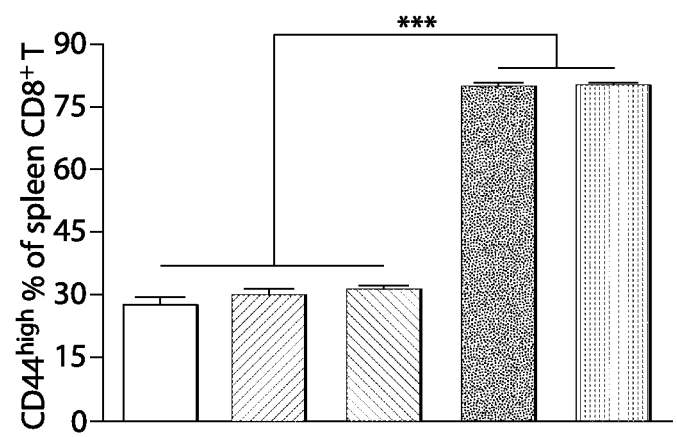
Figure 22D:
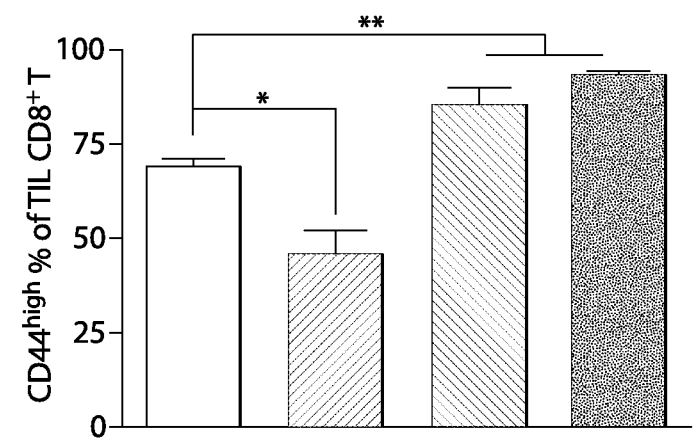

The effects of treatment on immune cells were examined in splenocytes and tumor-infiltrating leukocytes (TILs) harvested from mice bearing B16F10 melanoma tumors 3 days post-dosing therapy. Following ALT-803 administration, there was an increase in the CD8$^+$ T cell and NK cell populations, as well as a decrease in the CD4$^+$ T cell, B cell and macrophage populations, compared to the PBS control (FIG. 22A and FIG. 22B). As expected, TA99 did not alter the percentages of immune cell subsets in either splenocytes or TILs, except for causing a small reduction of tumor-associated macrophages. The ALT-803/TA99 combination showed similar changes in the immune cell populations as ALT-803 alone. ALT-803 alone or combined with TA99 led to significant increase in the memory phenotype (CD44$^{high}$) of CD8$^+$ T cells, supported by data from both splenocytes and TILs (FIG. 22C and FIG. 22D). Since the baseline CD8$^+$CD44$^{high}$ T cell population in TIL is two-fold greater than this cell population in spleen, ALT-803-mediated expansion of memory CD8$^+$ T cell was less prominent in TILs (1.2-fold, p<0.01 vs. 2.5-fold in spleen, p<0.001). TA99 slightly reduced the percentage of memory CD8$^+$ T cell (p<0.05) in TILs, probably because more effector CD8$^+$ T cells were driven to participate in the antibody-dependent immunity against melanoma.

To assess whether the ALT-803-enhanced immune memory could contributed to improved long-term immunity against tumor cells, ALT-803+TA99 treatment was started on study day 0 in an attempt to cure mice challenged with B16F10 tumor. In this treatment regimen, the addition of ALT-803 to TA99 therapy provided no improvement in animal survival except that a moderate increase in the percentage of tumor-free animals at SD60 was observed (FIG. 23A). However, when the surviving mice from the ALT-803+TA99 group were rechallenged with the B16F10 cells, a significant delay in tumor development was observed when compared to the age-match treatment naïve mice (FIG. 23B). These findings support the hypothesis that previous treatment with ALT-803 induced immune cell responses that are critical for the "vaccinal" protection of animals subjected to subsequent tumor rechallenge. To assess which cells were involved in this protective effect, depletion studies were conducted in ALT-803+TA99 "cured" mice prior to tumor cell rechallenge. The results showed that the ALT-803+TA99 "cured" mice administered PBS remained protected from B16F10 tumor rechallenge whereas those "cured" mice treated with antibodies depleting CD8, CD4 or NK cells showed no immune protection against mortality from subcutaneous B16F10 tumor rechallenge (FIG. 23C). These results indicate that all of these cell types are involved in the protective effects mediated by ALT-803+TA99 treatment following the initial tumor inoculation.

The role of immune cell activation and the PD-1/PD-L1 axis were also evaluated in this model. A single dose of ALT-803 upregulated CD25$^+$ cells in tumor-infiltrating CD4$^+$ T cells (p<0.05), while TA99 downregulated this activation marker (p<0.01; FIG. 24A). Moreover, ALT-803 treatment significantly increased PD-L1 expression on CD4$^+$ T cells both in periphery (p<0.001; FIG. 24B) and in the tumor (p<0.01; FIG. 24C). TA99 treatment resulted in a slight reduction of PD-L1 expression on CD4$^+$ T cells only in TIL (p<0.05), and TA99 with ALT-803 was not sufficient to change the impact from ALT-803 alone. Hence, the effectiveness of ALT-803 and its combination with therapeutic antibodies could possibly be limited by the strengthened immune checkpoint inhibitor pathway by CD4$^+$ T cells.

ALT-803 effects on PD-1 expression on CD8$^+$ T cells were also assessed in B16F10 tumor bearing mice. Single dose of ALT-803 led to moderate reduction of PD-1 expression on spleen CD8$^+$ T cells compared to PBS control, restoring it to a level close to naive mice (FIG. 24C). In addition, ALT-803, TA99 and ALT-803+TA99 combination therapy all reduced PD-1 expression on tumor-infiltrating CD8$^+$ T cells by about three fold (FIG. 24D).

Figure 25A:
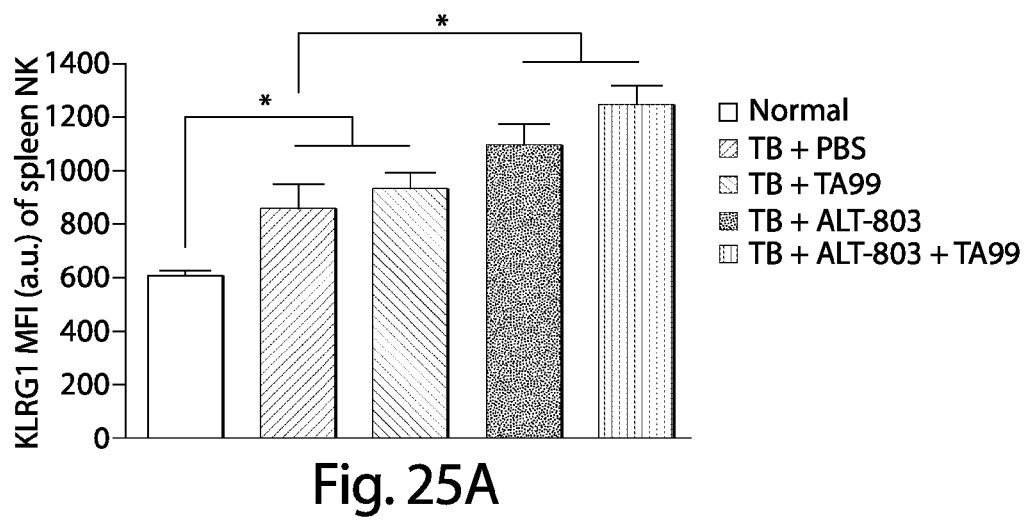
Figure 25B:
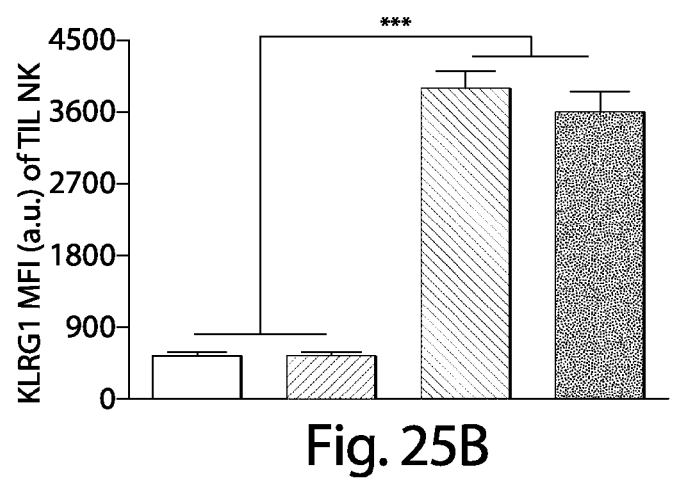
Figure 25C:
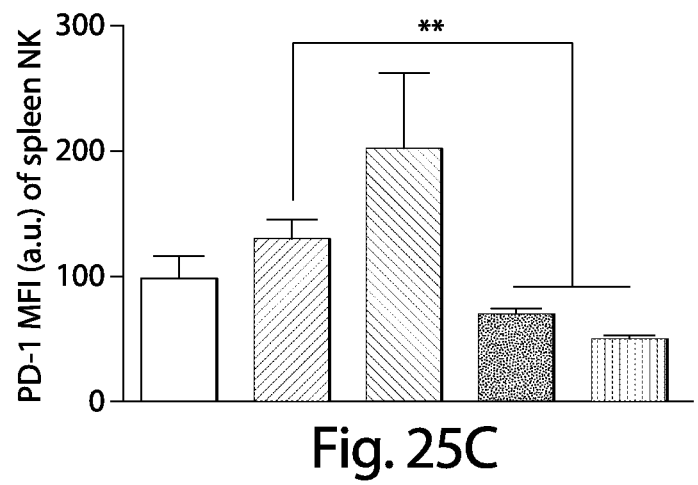
Figure 25D:
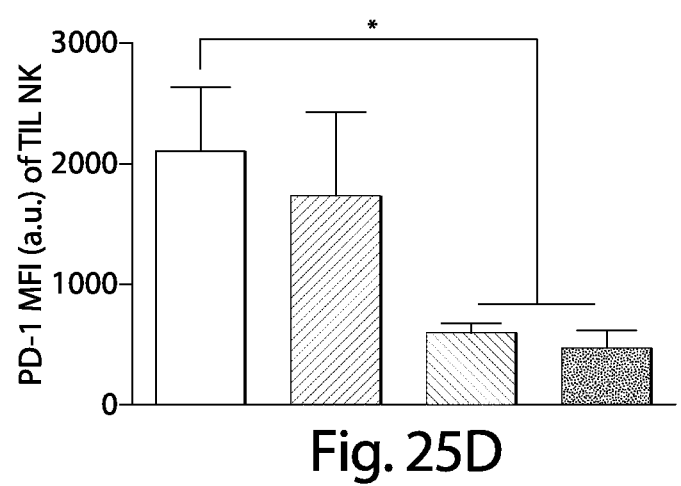

One important anti-tumor mechanism of action of IL-15 is through the activation of NK cells. When the activation marker KLRG1 was examined on NK cells, it was found that B16F10 melanoma, though poorly immunogenic, can induce a moderate increase of KLRG1 on spleen NK cells (p<0.05; FIG. 25A). ALT-803 treatment further increased the activation of NK cells in spleen (p<0.05; FIG. 25A) and more importantly, it caused a large increase of KLRG1 expression on tumor-infiltrating NK cells (4-fold, p<0.001; FIG. 25B). This might explain why ALT-803 can effectively boost TA99-mediated ADCC against B16F10 tumors where NK cells are a major immune cell involved in this response Like CD8$^+$ T cells, ALT-803 also downregulated PD-1 expression on NK cells in spleen (p<0.01; FIG. 25C) and tumor (p<0.05; FIG. 25D), implying that ALT-803 could intrinsically attenuate the inhibition from checkpoint pathway through the PD-1 arm of CD8$^+$ T cells and NK cells, independent of additional checkpoint blockade.

In order to explore whether checkpoint blockade would further enhance the combinatorial anti-tumor function of ALT-803 and TA99, mice (n=8) bearing established B16F10 tumors were treated with ALT-803+TA99 with and without anti-PD-L1 mAb 10F.9G2 in the delayed intervention model (FIG. 26A). Anti-PD-L1 mAb alone slowed tumor growth by a small factor (p<0.05). Thus, despite the observation that B16F10 cells constitutively express PD-L1 both in vitro and in vivo (FIG. 26B), anti-PD-L1 mAb failed to be a potent monotherapy for the inhibition of melanoma growth in this model. Judging from the tumor growth curve, ALT-803+TA99 combined with anti-PD-L1 mAb did exhibit greater anti-tumor activity when compared to ALT-803+TA99 therapy (p<0.05).

Overall, the results of these studies indicate that ALT-803 in combination with a tumor-specific antibody can provide antitumor activity and prolong survival of mice bearing established solid tumors. This treatment also provides immune protection against further tumor rechallenge. These effects are mediated by NK and T cells which are activated and proliferate in response to treatment. Additionally, therapeutic combinations with checkpoint inhibitors can further augment the antitumor efficacy of the ALT-803+tumor-specific antibody regimen. As a result, ALT-803 monotherapy and ALT-803 combination therapeutic strategies are applicable to various treatment approaches for neoplasia, including adjuvant, neo-adjuvant, induction, consolidation, maintenance, first line, ≥second line treatment and combinations with surgery, radiation or chemotherapy.

It is also noteworthy that ALT-803 alone or in combination with anti-tumor antibodies and/or checkpoint inhibitor blockade did not cause any significant signs of toxicity in the tumor-bearing animals for studies described above, which indicates that these combinations are well tolerated.

Example 10: Clinical Studies of ALT-803 in Patients with Malignancies

ALT-803 is being evaluated in patients with malignancies as follows.

A multi-center clinical study of ALT-803 is underway in patients with metastatic melanoma and other solid tumors. The study is being conducted as a dose escalation with one patient each to be enrolled in the first two cohorts and a minimum of three patients to be enrolled in the last three cohorts to determine the maximum tolerated dose (MTD) or Optimum Biological Dose (OBD) of ALT-803. Enrolled patients receive two 6-week cycles consisting of 4 weekly ALT-803 intravenous doses followed by a 2-week rest period. Patients with stable or benefiting disease will be eligible to receive up to two additional 6-week cycles. One patient enrolled to the 0.3 μg/kg ALT-803 dose level. The reported study drug-attributed adverse events were transient low-grade fever, rigors, nausea and vomiting. The next patient enrolled to the 0.5 μg/kg dose level. All reported adverse events were mild to moderate including nausea, fatigue and pruritus. Three patients enrolled and completed the study treatment at the 1 μg/kg ALT-803 dose level. All adverse events reported for these patients were mild to moderate, including chills, worsening constipation and hypertension. The study protocol for this trial was amended to include renal cell carcinoma, non-small cell lung carcinoma and squamous cell head and neck carcinoma. Three patients, including one patient with renal cell carcinoma, have enrolled to the 3 μg/kg dose level. Adverse events reported so far were mild to moderate including fever, fatigue, vomiting and myalgia. There have been no dose limiting toxicities, Grade 3/4 toxicities or severe adverse events in any of these ALT-803 treated patients, which indicates that this treatment was well tolerated. Disease stabilization has been reported in some patients and treatment-mediated clinical benefit (including decreased tumor burden, disease progression or relapse or toxicity, or increased progression free survival, time to progression, duration of response, survival, or quality of life) is expected.

A multi-center clinical study of ALT-803 is underway in patients with hematologic malignancy who have relapsed after autologous stem cell transplantation (ASCT). The first phase of this study is being conducted under a standard 3+3 design of dose escalation for toxicity. Enrolled patients receive ALT-803 intravenous doses given once weekly for 4 weeks. Six patients have enrolled and completed the study treatment at the 1 μg/kg ALT-803 dose level. For the first three patients, the reported study drug-attributed adverse events were fever, chills, rigors and edema. Grade 1 fever in two patients occurred approximately 4 to 5 hours after ALT-803 dosing and then subsided approximately 6 to 7 hours after ALT-803 dosing. Grade 2 rigors occurred in two patients, grade 2 chills occurred in two patients and grade 1 chills occurred in one patient. Grade 2 rigors in one patient required Demerol for 3 out of 4 ALT-803 doses. One patient experienced grade 2 edema and another patient experienced grade 1 edema. The first three patients experienced asymptomatic hypotension, but the patients were normotensive after fluid administration without the recurrence of hypotension episodes. None of the treated patients were pre-hydrated with fluids. Grade 2 skin rash was also observed in one patient after the second dose of ALT-803, which was consistent with graft-versus-host disease. The fourth, fifth and sixth patients received the study treatment with no reported AEs. Three patients completed the study treatment at the 3 μg/kg ALT-803 dose level. The patients received hydration prior to each dose, reported adverse events include grade 1 fever and chills 6 and 10 hours after ALT-803 dosing. Three patients enrolled and completed treatment at the 6 μg/kg ALT-803 dose level. Most common reported adverse events in this cohort include mild to moderate fever, rigors and flu-like symptoms. Two patients are being treated at the 10 μg/kg ALT-803 dose level. Reported adverse events for the first patient after the first dose of ALT-803 include transient fever, nausea and vomiting. The adverse events started around 3 hours after dosing and lasted approximately 4 hours. The patient also experienced low grade asymptomatic hypotension. IV fluids were administered and the blood pressure returned to baseline. The second patient experienced transient fever and chills after the first dose of ALT-803. The chills were controlled with Demoral. There have been no dose limiting toxicities, Grade 3/4 toxicities or severe adverse events in any of these ALT-803 treated patients, which indicates that this treatment was well tolerated. The protocol was amended to change the administration of ALT-803 from IV to subcutaneous injection starting at the 6 µg/kg dose level. Patient enrollment will continue at the 10 µg/kg dose level with i.v. administration until a total of three patients are enrolled in this cohort. Patient enrollment for subcutaneous injection at 6 µg/kg will then be initiated. Treatment-mediated clinical benefit (including decreased tumor burden, disease progression or relapse or toxicity, or increased progression free survival, time to progression, duration of response, survival, or quality of life) is expected.

Clinical biomarker assessment is being conducted. For the study of patients with hematologic malignancy after ASCT, preliminary data is available on the Ki-67 analysis of NK, $CD4^+$, $CD8^+$ and NKT cell subsets and serum cytokines of the patients' pre-dose and post-dose specimens. Serum levels of both IFN-γ and IL-6 were induced in a dose-dependent manner within the dose range from 1 µg/kg to 6 µg/kg ALT-803. $Ki67^+$ NK, $CD8^+$ and $CD4^+$ T cells increased after ALT-803 dosing at a dose level of ≥3 µg/kg in all patients. Thus, the preliminary data suggests that ALT-803 consistently promotes the activation and proliferation of NK, T and NKT cells for patients at a dose level of ≥3 µg/kg with this indication. Similarly, serum levels of IFN-γ and IL-6 were induced in patients with solid tumors following administration of ALT-803, indicating treatment-related immune stimulation in these patients.

A multi-center clinical study of ALT-803 is underway in patients with relapsed or refractory multiple myeloma. The first phase of this study includes a classic (3+3) dose escalation to determine the MTD or minimum efficacious dose (MED) and to designate a dose level for the phase II two-stage expansion. The dose levels are 1, 3, 6, 10 and 20 µg/kg of ALT-803. Enrolled patients will receive two 6-week cycles consisting of 4 weekly ALT-803 intravenous doses followed by a 2-week rest period. Patients with stable or benefiting disease will be eligible to receive up to two additional 6-week cycles. Three patients enrolled and completed the study treatment at the 1 µg/kg ALT-803 dose level. All adverse events reported for these patients were mild to moderate, including constipation, nausea, fatigue, ALC decreased and WBC count decreased. All patients are receiving pre-medications. Two patients are undergoing treatment at the 3 µg/kg ALT-803 dose level. Reported adverse events include mild to moderate fevers, rigors and neutropenia. There have been no dose limiting toxicities, Grade 3/4 toxicities or severe adverse events in any of these ALT-803 treated patients, which indicates that this treatment was well tolerated. Treatment-mediated clinical benefit (including decreased tumor burden, disease progression or relapse or toxicity, or increased progression free survival, time to progression, duration of response, survival, or quality of life) is expected. Serum levels of IFN-γ and IL-6 were induced in patients with multiple myeloma following administration of ALT-803, indicating treatment-related immune stimulation in these patients.

A multi-center clinical study of ALT-803 in combination with *Bacillus* Calmette-Guerin (BCG) is in patients with BCG-naïve non-muscle invasive bladder cancer. The first phase of this study includes a classic (3+3) dose escalation to determine the MTD of ALT-803 and to determine the recommended dose (RD) of ALT-803 combined with BCG for the expansion phase. The dose levels are 100, 200 and 400 µg/instillation of ALT-803 plus standard BCG (50 mg/instillation). The expansion phase consists of a noncomparative randomized design of patients receiving ALT-803 at the RD level in combination with BCG or BCG alone. Enrolled patients will receive BCG plus ALT-803 weekly via a urinary catheter in the bladder for 6 consecutive weeks. Three patients enrolled and completed treatment in the first cohort of 100 µg/instillation of ALT-803 plus BCG. Reported study drug-attributed adverse events included mild nausea, headache, hematuria and urinary tract pain and moderate cystitis noninfective. Three patients have enrolled and completed treatment in the 200 µg/instillation of ALT-803 plus BCG. Reported study drug-attributed adverse events included mild hematuria and urinary incontinence. Two patients enrolled are ongoing treatment in the 400 µg/instillation of ALT-803 cohort. There have been no dose limiting toxicities, Grade 3/4 toxicities or severe adverse events in any of these ALT-803 plus BCG treated patients, which indicates that this treatment was well tolerated. A number of these treated patients exhibited no disease recurrence (considered a complete response in this indication) for at least 9 months post therapy, suggesting treatment-related clinical activity. Treatment-related increases in urinary cytokines were also observed in some patients. Treatment-mediated clinical benefit (including decreased tumor burden, disease progression or relapse or toxicity, or increased progression free survival, time to progression, duration of response, survival, or quality of life) is expected.

A multi-center clinical study of ALT-803 plus rituximab is underway in patients with relapsed or refractory indolent B cell non-Hodgkin lymphoma. The first phase of this study includes a classic (3+3) dose escalation to determine the MTD or MED and to designate a dose level for the phase II two-stage expansion. The dose levels are 1, 3 and 6 µg/kg of ALT-803. Enrolled patients will receive a 4-week induction cycle consisting of 4 weekly doses of ALT-803 and standard rituximab (375 mg/m2) by intravenous injection. Patients with stable or benefiting disease will be eligible to receive up to four consolidation treatment cycles consisting of a single treatment of ALT-803 plus rituximab, repeated every 8 weeks for a total of 4 additional ALT-803 and rituximab doses. One patient enrolled and is currently undergoing treatment at the 1 µg/kg ALT-803 dose level. Adverse events reported thus far for this patient were mild to moderate including edema, ALC decreased and WBC count decreased. There have been no dose limiting toxicities, Grade 3/4 toxicities or severe adverse events in the ALT-803+rituximab treated patient, which indicates that this treatment was well tolerated. Treatment-mediated clinical benefit (including decreased tumor burden, disease progression or relapse or toxicity, or increased progression free survival, time to progression, duration of response, survival, or quality of life) is expected.

A multi-center clinical study of ALT-803 plus nivolumab (anti-PD-1 Ab) will be conducted in patients with advanced or metastatic non-small cell lung cancer. The first phase of this study includes a dose escalation to determine the MTD of ALT-803 and to designate a dose level for the phase II two-stage expansion. The dose levels are 6, 10, and 15 µg/kg of subcutaneous ALT-803. Enrolled patients will receive two 6-week cycles consisting of 5 weekly doses of ALT-803 and standard intravenously nivolumab every 2 weeks (3 mg/kg). Patients with stable or benefiting disease will be eligible to receive additional 6-week ALT-803 plus nivolumab cycles. Treatment-mediated clinical benefit (including decreased tumor burden, disease progression or relapse or toxicity, or increased progression free survival, time to progression, duration of response, survival, or quality of life) is expected.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a neoplasia or a human immunodeficiency virus (HIV) infection in a subject, the method comprising:

administering to said subject an effective amount of an antibody and an effective amount of a pharmaceutical composition comprising an IL-15N72D:IL-15RαSu/Fc complex (ALT-803), wherein said antibody is an immune checkpoint inhibitor antibody or a tumor-specific antibody, and wherein said ALT-803 comprises a dimeric IL-15RαSu/Fc and two IL-15N72D molecules, thereby treating the neoplasia or HIV infection.

2. The method of claim 1, wherein the IL-15N72D molecule comprises the amino acid sequence of SEQ ID NO: 3.

3. The method of claim 1, wherein the IL-15RαSu/Fc comprises the amino acid sequence of SEQ ID NO: 6.

4. The method of claim 1, wherein the subject is suffering from a neoplasia and the neoplasia is selected from the group consisting of a glioblastoma, prostate cancer, hematological cancer, B-cell neoplasms, multiple myeloma, B-cell lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, colorectal cancer, ovarian cancer, non-small cell lung carcinoma, B cell non-Hodgkin lymphoma, and squamous cell head and neck carcinoma.

5. The method of claim 1, wherein the effective amount of said ALT-803 is administered daily.

6. The method of claim 5, wherein the effective amount of said ALT-803 is between 0.1 μg/kg and 100 mg/kg.

7. The method of claim 1, wherein the effective amount of said ALT-803 is administered once or twice per week.

8. The method of claim 7, wherein the effective amount of said ALT-803 is between 0.1 μg/kg and 1 mg/kg.

9. The method of claim 1, wherein the pharmaceutical composition is administered systemically, intravenously, subcutaneous, intramuscularly, intravesically, or by instillation.

10. The method of claim 1, wherein said antibody comprises an anti-gp75 antibody, an anti-CD20 antibody, an anti-HER2 antibody, an anti-EGFR antibody, an anti-cytotoxic T-lymphocyte antigen 4 (CTLA-4) antibody, an anti-programmed cell death-1 (PD-1) antibody, an anti-programmed cell death-ligand 1 (PD-L1) antibody, or an anti-programmed cell death-ligand 2(PD-L2) antibody.

11. The method of claim 1, wherein antibody-dependent cell-mediated cytotoxicity (ADCC) or antibody dependent cellular phagocytosis (ADCP) mediated by said antibody against tumor or infected cells in said subject is augmented by at least 5% following said administration.

12. The method of claim 1, wherein said antibody and said ALT-803 increases levels of blood NK cell, T cell, neutrophil or monocyte counts or activity.

13. The method of claim 1, wherein said antibody and said ALT-803 stimulate CD4+ or CD8+ T cells to kill tumor or infected cells.

14. The method of claim 1, wherein said antibody and said ALT-803 stimulate NK cells to kill tumor or infected cells.

15. The method of claim 1, wherein said antibody and said ALT-803 stimulate neutrophils or monocytic cells to kill tumor or infected cells.

16. The method of claim 1, wherein said administration results in a decrease in the number of tumor or infected cells.

17. The method of claim 1, wherein said administration results in a decrease in disease progression of the neoplasia or infection.

18. The method of claim 1, wherein said administration results in prolonged survival of said subjects compared to untreated subjects.

19. The method of claim 1, wherein said subject is a human.

20. The method of claim 1, wherein said antibody and said ALT-803 are administered simultaneously or sequentially.

21. The method of claim 1, wherein said administration prevents future recurrence of said neoplasia or infection.

22. The method of claim 1, wherein said antibody and said ALT-803 increase blood cytokine levels.

23. The method of claim 22, wherein said cytokine comprises IFN-γ and/or IL-6.

24. The method of claim 1 wherein the subject is suffering from a neoplasia and the neoplasia is treated.

25. The method of claim 1 wherein the subject is suffering from an HIV infection and the HIV infection is treated.

* * * * *